United States Patent
Muñoz et al.

(10) Patent No.: US 10,202,330 B2
(45) Date of Patent: *Feb. 12, 2019

(54) LYSINE SPECIFIC DEMETHYLASE-1 INHIBITORS AND THEIR USE

(71) Applicant: ORYZON GENOMICS S.A., Cornellà de Llobregat, Barcelona (ES)

(72) Inventors: Alberto Ortega Muñoz, Barcelona (ES); Julio Castro-Palomino Laria, Barcelona (ES); Matthew Colin Thor Fyfe, Chipping Norton (GB)

(73) Assignee: ORYZON GENOMICS, SA, Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 14/843,095

(22) Filed: Sep. 2, 2015

(65) Prior Publication Data

US 2015/0368186 A1    Dec. 24, 2015

Related U.S. Application Data

(60) Continuation of application No. 14/228,083, filed on Mar. 27, 2014, now Pat. No. 9,149,447, which is a division of application No. 13/641,916, filed as application No. PCT/EP2011/056279 on Apr. 19, 2011, now Pat. No. 8,722,743.

(30) Foreign Application Priority Data

Apr. 19, 2010  (EP) .................................. 10160315

(51) Int. Cl.

| | |
|---|---|
| A61K 31/165 | (2006.01) |
| C07C 217/74 | (2006.01) |
| A61K 45/06 | (2006.01) |
| C07C 211/42 | (2006.01) |
| C07C 211/40 | (2006.01) |
| C07C 237/24 | (2006.01) |
| A61K 31/135 | (2006.01) |
| A61N 5/10 | (2006.01) |

(52) U.S. Cl.
CPC .......... *C07C 217/74* (2013.01); *A61K 31/135* (2013.01); *A61K 31/165* (2013.01); *A61K 45/06* (2013.01); *A61N 5/10* (2013.01); *C07C 211/40* (2013.01); *C07C 211/42* (2013.01); *C07C 237/24* (2013.01); *C07C 2101/02* (2013.01); *C07C 2101/14* (2013.01); *C07C 2101/18* (2013.01); *C07C 2102/08* (2013.01); *C07C 2102/10* (2013.01)

(58) Field of Classification Search
CPC .................................................... A61K 31/165
USPC .................... 514/255.01, 619, 647
See application file for complete search history.

(56) References Cited

U.S. PATENT DOCUMENTS

| | | |
|---|---|---|
| 3,106,578 A | 10/1963 | Kaiser et al. |
| 3,365,458 A | 1/1968 | Biel et al. |
| 3,471,522 A | 10/1969 | Biel et al. |
| 3,532,712 A | 10/1970 | Biel et al. |
| 3,532,749 A | 10/1970 | Biel et al. |
| 3,758,684 A | 9/1973 | Elion et al. |
| 4,409,243 A | 10/1983 | Lieb |
| 4,522,811 A | 6/1985 | Eppstein et al. |

(Continued)

FOREIGN PATENT DOCUMENTS

| | | |
|---|---|---|
| EP | 1193268 | 4/2002 |
| EP | 1704859 | 9/2006 |

(Continued)

OTHER PUBLICATIONS

Ahmed et al, "Ticagrelor: a new reversible oral antiplatelet agent" Int Research Journal of Pharmacy, 2010, 1(1), 62-69.

Arya et al, "Synthesis of 5H-dibenzo[a,d]cycloheptene derivatives with diverse biological activities", Indian J Chemistry B, 1978, 16B,220-225.

Bar-Am et al, "Regulation of Bcl-2 familey proteins, neurotrophic factors, and APP processing in the neurorescue activity of propargylamine". FASEB J, 2005, 19(13),1899-1901.

Barlesi et al, "Global histone modifications predict prognosis of resected non small-cell lung cancer",J Clin Oncol,2007,25, 4358-4364.

Benelkebir et al, "Enantioselective synthesis of tranylcypromine analogues as lysine demethylase (LSD1) inhibitors", Bioorg Med Chem, 2011,19(12),3709-3716.

(Continued)

*Primary Examiner* — Rei Tsang Shiao
(74) *Attorney, Agent, or Firm* — Finnegan, Henderson, Farabow, Garrett & Dunner, LLP

(57) ABSTRACT

The present invention relates to a compound of Formula 1, wherein: (A) is heteroaryl or aryl; each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl; X is 0, 1, 2, or 3; (B) is a cyclopropyl ring, wherein (A) and (Z) are covalently bonded to different carbon atoms of (B); (Z) is —NH—; (L) is chosen from a single bond, —CH$_2$—, —CH$_2$CH$_2$—, —CH$_2$CH$_2$CH$_2$—, and —CH$_2$CH$_2$CH$_2$CH$_2$—; and (D) is an aliphatic carbocyclic group or benzocycloalkyl, wherein said aliphatic carbocyclic group or said benzocycloalkyl has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy. (A')X-(A)-(B)—(Z)-(L)-(D) formula (I) The compounds of the invention show activity for inhibiting LSD1, which makes them useful in the treatment or prevention of diseases such as cancer.

2 Claims, No Drawings

(56) References Cited

U.S. PATENT DOCUMENTS

| | | | |
|---|---|---|---|
| 4,530,901 | A | 7/1985 | Weissmann |
| 6,043,393 | A | 3/2000 | de Meijere et al. |
| 6,211,244 | B1 | 4/2001 | Van Wagenen et al. |
| 6,337,074 | B1 | 1/2002 | Marsden et al. |
| 6,809,120 | B1 | 10/2004 | Warrington et al. |
| 7,399,825 | B2 | 7/2008 | Lipps et al. |
| 7,611,704 | B2 | 11/2009 | Thorpe et al. |
| 7,628,993 | B2 | 12/2009 | Vilalta et al. |
| 7,799,782 | B2 * | 9/2010 | Munson ............... C07D 231/56 514/234.5 |
| 8,524,717 | B2 * | 9/2013 | Guibourt ............... C07C 229/14 514/255.01 |
| 8,722,743 | B2 * | 5/2014 | Ortega Munoz ..... C07C 211/35 514/619 |
| 8,859,555 | B2 | 10/2014 | Ortega-Muñoz et al. |
| 8,946,296 | B2 | 2/2015 | Ortega Muñoz et al. |
| 8,993,808 | B2 | 3/2015 | Guibourt et al. |
| 9,006,449 | B2 | 4/2015 | Fyfe et al. |
| 9,061,966 | B2 | 6/2015 | Laria et al. |
| 9,149,447 | B2 * | 10/2015 | Munoz ................. A61K 31/135 |
| 9,181,198 | B2 | 11/2015 | Ortega-Muñoz et al. |
| 9,186,337 | B2 * | 11/2015 | Baker ................. A61K 31/131 |
| 9,616,058 | B2 * | 4/2017 | Cesar Castro Palomino Lana ..... A61K 31/495 |
| 2003/0008844 | A1 | 1/2003 | Spero et al. |
| 2003/0236225 | A1 | 12/2003 | Protopopova et al. |
| 2004/0019117 | A1 | 1/2004 | Protopopova et al. |
| 2004/0033986 | A1 | 2/2004 | Protopopova et al. |
| 2004/0048802 | A1 | 3/2004 | Ripka et al. |
| 2004/0132820 | A1 | 7/2004 | Gosselin et al. |
| 2004/0147741 | A1 | 7/2004 | Sundermann et al. |
| 2004/0162287 | A1 | 8/2004 | Sundermann et al. |
| 2004/0176469 | A1 | 9/2004 | Nadackal |
| 2004/0229872 | A1 | 11/2004 | Friderichs et al. |
| 2004/0254158 | A1 | 12/2004 | Qiao et al. |
| 2005/0009832 | A1 | 1/2005 | Sun et al. |
| 2005/0154056 | A1 | 7/2005 | Yang et al. |
| 2006/0116370 | A1 | 6/2006 | Dollinger et al. |
| 2006/0148904 | A1 | 7/2006 | Protopopova et al. |
| 2006/0211709 | A1 | 9/2006 | Buhr et al. |
| 2006/0270673 | A1 | 11/2006 | Duggan et al. |
| 2006/0275366 | A1 | 12/2006 | Malcolm et al. |
| 2006/0287287 | A1 | 12/2006 | Gerritz et al. |
| 2007/0213338 | A1 | 9/2007 | Lebsack et al. |
| 2008/0139665 | A1 | 6/2008 | Schuele et al. |
| 2008/0242698 | A1 | 10/2008 | Flor et al. |
| 2008/0269228 | A1 | 10/2008 | Moore et al. |
| 2009/0203750 | A1 | 8/2009 | Kozikowski et al. |
| 2009/0247530 | A1 | 10/2009 | Nolte et al. |
| 2010/0016262 | A1 | 1/2010 | Mehal et al. |
| 2010/0240649 | A1 | 9/2010 | Zhang |
| 2010/0292225 | A1 | 11/2010 | Chamoin et al. |
| 2010/0324147 | A1 | 12/2010 | McCafferty et al. |
| 2012/0202810 | A1 | 8/2012 | Nolte et al. |
| 2013/0197095 | A1 | 8/2013 | Nolte et al. |
| 2013/0274267 | A1 | 10/2013 | Cesar Castro Palomino Laria et al. |
| 2014/0163041 | A1 | 6/2014 | Fyfe et al. |
| 2014/0256742 | A1 | 9/2014 | Baker et al. |
| 2014/0296255 | A1 | 10/2014 | Maes et al. |
| 2014/0329833 | A1 | 11/2014 | Maes et al. |
| 2015/0025054 | A1 | 1/2015 | Ortega Muñoz et al. |
| 2015/0119396 | A9 | 4/2015 | Ortega Muñoz et al. |
| 2015/0232436 | A1 | 8/2015 | Baker et al. |
| 2015/0368186 | A1 | 12/2015 | Muñoz et al. |
| 2015/0376177 | A1 | 12/2015 | Ortega Muñoz et al. |
| 2016/0000768 | A1 | 1/2016 | Castro-Palomino Laria et al. |
| 2016/0045456 | A1 | 2/2016 | Guibourt et al. |
| 2016/0052865 | A1 | 2/2016 | Fyfe et al. |
| 2016/0081947 | A1 | 3/2016 | Maes et al. |

FOREIGN PATENT DOCUMENTS

| | | |
|---|---|---|
| EP | 1741708 | 1/2007 |
| EP | 2233495 | 9/2010 |
| GB | 1307341 | 2/1973 |
| JP | 2001354563 | 12/2001 |
| SU | 230169 | 10/1968 |
| WO | WO94/27947 | 12/1994 |
| WO | WO96/38141 | 12/1996 |
| WO | WO98/18459 | 5/1998 |
| WO | WO99/05142 | 2/1999 |
| WO | WO99/05143 | 2/1999 |
| WO | WO99/31072 | 6/1999 |
| WO | WO99/54440 | 10/1999 |
| WO | WO99/67203 | 12/1999 |
| WO | WO00/34283 | 6/2000 |
| WO | WO2001/092264 | 12/2001 |
| WO | WO2002/079152 | 10/2002 |
| WO | WO2003/087064 | 10/2003 |
| WO | WO2003/093297 | 11/2003 |
| WO | WO2003/096989 | 11/2003 |
| WO | WO2004/020415 | 3/2004 |
| WO | WO2004/055010 | 7/2004 |
| WO | WO2004/062601 | 7/2004 |
| WO | WO2004/065367 | 8/2004 |
| WO | WO2004/072086 | 8/2004 |
| WO | WO2005/009941 | 2/2005 |
| WO | WO2005/023761 | 3/2005 |
| WO | WO2005/025558 | 3/2005 |
| WO | WO2005/037843 | 4/2005 |
| WO | WO2005/058808 | 6/2005 |
| WO | WO2005/058883 | 6/2005 |
| WO | WO2005/058884 | 6/2005 |
| WO | WO2005/103003 | 11/2005 |
| WO | WO2006/071608 | 7/2006 |
| WO | WO2006/087206 | 8/2006 |
| WO | WO2007/000248 | 1/2007 |
| WO | WO2007/005896 | 1/2007 |
| WO | WO2007/015824 | 2/2007 |
| WO | WO2007/025144 | 3/2007 |
| WO | WO2007/025709 | 3/2007 |
| WO | WO2007/021839 | 7/2007 |
| WO | WO2007/106016 | 9/2007 |
| WO | WO2007/134799 | 11/2007 |
| WO | WO2008/033466 | 3/2008 |
| WO | WO2008/116156 | 9/2008 |
| WO | WO2008/127734 | 10/2008 |
| WO | WO2009/001132 | 12/2008 |
| WO | WO2009/023179 | 2/2009 |
| WO | WO2009/039134 | 3/2009 |
| WO | WO2009/097278 | 4/2009 |
| WO | WO2009/097278 | 8/2009 |
| WO | WO2009/109991 | 9/2009 |
| WO | WO2009/117515 | 9/2009 |
| WO | WO2009/145858 | 12/2009 |
| WO | WO2009/153197 | 12/2009 |
| WO | WO2010/011845 | 1/2010 |
| WO | WO2010/014921 | 2/2010 |
| WO | WO2010/030592 | 3/2010 |
| WO | WO2010/043721 | 4/2010 |
| WO | WO2010/084160 | 7/2010 |
| WO | WO2010/085749 | 7/2010 |
| WO | WO2010/099527 | 9/2010 |
| WO | WO2010/139784 | 12/2010 |
| WO | WO2010/143582 | 12/2010 |
| WO | WO2011/022489 | 2/2011 |
| WO | WO2011/031934 | 3/2011 |
| WO | WO2011/035941 | 3/2011 |
| WO | WO2011/042217 | 4/2011 |
| WO | WO2011/057262 | 5/2011 |
| WO | WO2011/106105 | 9/2011 |
| WO | WO2011/106106 | 9/2011 |
| WO | WO2011/113005 | 9/2011 |
| WO | WO2011/131576 | 10/2011 |
| WO | WO2011/132083 | 10/2011 |
| WO | WO2012/001531 | 1/2012 |
| WO | WO2012/013727 | 2/2012 |
| WO | WO2012/013728 | 2/2012 |
| WO | WO2012/034116 | 3/2012 |

(56) References Cited

FOREIGN PATENT DOCUMENTS

| WO | WO2012/042042 | 4/2012 |
| --- | --- | --- |
| WO | WO2012/045883 | 4/2012 |
| WO | WO2012/072713 | 6/2012 |
| WO | WO2012/107498 | 8/2012 |
| WO | WO2012/107499 | 8/2012 |
| WO | WO2012/135113 | 10/2012 |
| WO | WO2012/156531 | 11/2012 |
| WO | WO2012/156537 | 11/2012 |
| WO | WO2013/057320 | 4/2013 |
| WO | WO2013/057322 | 4/2013 |

OTHER PUBLICATIONS

Biljak et al,"Platelet count, mean platelet volume and smoking status in stable chronic obstructive pulmonary disease", Platelets, 2011,22(6), 466-70.

Binda et al, "Biochemical, structural, and biological evaluation of tranylcypromine derivatives as inhibitors of histone demethylases LSD1 and LSD2", J Am Chem Soc,2010,132(19),6827-6833.

Bisi et al, "Multidrug resistance reverting activity and antitumor profile of new phenothiazine derivatives", Bioorg Med Chem, 2008, 16(13), 6474-6482.

Boilard et al, "Platelets amplify inflammation in arthritis via collagen-dependent microparticle production", Science, 2010,327(5965), 580-583.

Bolesov et al, "Cyclopropanes and cyclobutanes LXIX", Zhurnal Organicheskoi Khimii (English Translation), 1974, 10(10), 2122-2128.

Bolesov et al, "Cyclopropanes and cyclobutanes LXVIII. N-mono and N,N-disubstituted 1-amino-2-phenylcyclopropanes",Zhurnal Organicheskoi Khimii (English Translation), 1974, 10(6), 1678-84.

Brand and Perrimon, "Targeted gene expression as a means of altering cell fates and generating dominant phenotypes", 1993, Development, 118, 401-415.

Brydon et al, "Platelets, coronary heart disease and stress", Brain, Behavior and Immunity,2006, 20(2), 113-119.

Burakova et al, "N- and O-alkylation of 3-indolylcyclopropylacetic acid derivatives", Russian Chemical Bulletin, 2002, 51(10) 1829-1840.

Burk et al, "Cognitive deficits in spinocerebellar ataxia 2", Brain, 1999, 122(4), 769-777.

Cakmak et al, "Platelets: indicator of inflammation in COPD", Int J Med Med Sci, 2009, 1(5), 227-229.

Calogero et al, "Inhibition of cell growth by EGR-1 in human primary cultures from malignant glioma",Cancer Cell International,2004,4, 1.

Casero et al, "Recent advances in the development of polyamine analogues as antitumor agents", J Med Chem, 2009, 52(15),4551-4573.

Chen et al, "Association of insulin resistance and hematologic parameters: study of a middle-aged and elderly chinese population in Taiwan", J Chen Med Assoc,2006, 69(6), 248-253.

Chimenti et al "Synthesis, Stereochemical Identification, and Selective Inhibitory Activity against Human Monoamine Oxidase-B of 2-Methylcyclohexylidene-(4-arylthiazol-2-yl)hydrazones". (2008) J. Med. Chem. 51 (16), 4874-4880.

Choi et al "Histone demethylase LSD1 is required to induce skeletal muscle differentiation by regulating myogenic factors" (2010) Biochemical and Biophysical Research Communications 401(3), 327-332.

Choo et al, "Genetic organization and diversity of the hepatitis C virus", Proc Natl Acad Sci,1991, 88,2451-2455.

Culhane et al, A mechanism-based inactivator for histone demethylase LSD1, J Am Chem Soc, 2006, 128(14), 4536-4537.

Culhane et al, "Comparative analysis of small molecules and histone substrate analogues as LSD1 lysine demethylase inhibitors", J Am Chem Soc, 2010,132(9),3164-3176.

Danese et al, "Platelets in inflammatory Bowel disease: clinical, pathogenic and therapeutic implications", Am J Gastroenterol, 2004,99(5), 938-45.

Di Stefano et al, Mutation of Drosophila Lsd1 disrupts H3-K4 methylation, resulting in tissue-specific defects during development, Curr Bio,2007, 17(9), 808-12.

East et al, "An orally bioavailable positive allosteric modulator of the mGlu4 receptor with efficacy in an animal model of motor dysfunction", Bioorg Med Chem Lett, 2010, 20(16), 4901-5.

Ellis et al, "Expression of Drosophila glass protein and evidence for negative regulation of its activity in non-neuronal cells by another DNA-binding protein",Development,1993, 119, 855-865.

Elsheikh et al "Global histone modifications in breast cancer correlate with tumor phenotypes, prognostic factors and patient outcome", Canc Res, 2009,69, 3802-3809.

Erazo et al, "Varicella-zoster virus open reading frame 66 protein kinase is required for efficient viral growth in primary human corneal stromal fibroblast cells", J Virol, 2008,82, 7653-7665.

Faler et al, "The Kulinkovich reaction in the synthesis of constrained N,N-dialkyl neurotransmitter analogues", Organic Letters 2007,9(10),1987-1990.

Ferlay et al, "Estimates of the cancer incidence and mortality in Europe in 2006", Annals of Oncology 2007,18(3), 581-92.

Ferraro et al, "EGR1 predicts PTEN and survival in patients with non-small-cell lung cancer", J Clin Oncol, 2005, 23(9), 1921-26.

Fischer et al, "Recovery of learning and memory is associated with chromatin remodelling", Nature, 2007,447, 178-182.

Forneris et al "LSD1: oxidative chemistry for multifaceted functions in chromatin Regulation." Trends in Biochemical Sciences 2008,33(4), 181-189.

Gawaz et al, "Platelets in inflammation and atherogenesis", J Clint Invest, 2005,115(12), 3378-3384.

Gooden et al, "Facile synthesis of substituted trans-2-arylcyclopropylamine inhibitors of the human histone demethylase LSD1 and monoamine oxidases A and B", Bioorg Med Chem Lett 2008, 18(10), 3047-51.

Han et al "Modulation of breast cancer resistance protein (BCRP/ABCG2) by non-basic chalcone analogues" Eur. J. Pharma. 2008, 35(1-2) 30-41.

Han et al, "Antidepressants reveal differential effect against 1-methyl-4-phenylpyridinium toxicity in differentiated PC12 cells", Eur J Pharmacol, 2009, 604 (1-3),36-44.

Hayami et al, "Overexpression of LSD1 contributes to human carcinogenesis through chromatin regulation in various cancers", Int J Cancer, 2011, 128(3), 574-86.

Hruschka et al, "Fluorinated phenylcyclopropylamines. Part 5:Effect of electron-withdrawing or—donating aryl substituents on the inhibition of monoamine oxidases A and B by 2-aryl-2-fluoro-cyclopropylamines", Bioorg Med Chem,2008, 16(15), 7148-7166.

Huang et al, "Novel oligoamine analogues inhibit lysine-specific demethylase 1 (LSD1) and induce re-expression of epigeneticall silenced genes",Clin Cancer Res,2009, 15(23), 7217-28.

Huang et al, "p53 is regulated by the lysine demethylase LSD1",Nature,2007,449, 105-108.

Huang et al,"Inhibition of lysine-specific demethylase 1 by polyamine analogues results in reexpression of aberrantly silenced genes", PNAS,2007, 104(19), 8023-8028.

Jackson et al, "Polyglutamine-expanded human Huntingtin transgenes induce degeneration of Drosophila photoreceptor neurons", Neuron, 1998, 21, 633-642.

Kahl et al,"Androgen receptor coactivators lysine-specific histone demethylase 1 and four and a half LIM domain protein 2 predict risk of prostate cancer recurrence", Cancer Res,2006,66 (23), 11341-11347.

Kaiser et al, "2-substituted cyclopropylamines. I. Derivatives and analogs of 2-phenylcyclopropylamine", J Med Pharm Chem (ACS), 1962, 5, 1243-1265.

Kiefmann et al, "Red blood cells induce hypoxic lung inflammation", Blood, 2008,111(10),5205-14.

Kim et al, "Flavin chemical models for monoamine oxidase inactivation by cyclopropylamines, α-silylamines, and hydrazines", J Am Chem Soc 1995, 117, 100-105.

(56) References Cited

OTHER PUBLICATIONS

Kinzel et al, "Identification of MK-5710 ((8aS)-8a-methyl-1,3-dioxo-2-[(1S,2R)-2-phenylcyclopropyl]-N-(1-phenyl-1H-pyrazol-5-yl)hexahydro-imidazo[1,5-a]pyrazine-7-(1H)-carboxamide), a potent smoothened antagonist for use in Hedgehog pathway dependent malignancies Part 2", Bioorg Med Chem Lett 2011, 21(15), 4429-4435.

Kornerup et al, "The role of platelets in the pathophysiology of asthma" Platelets, 2007,18(5), 319-28.

Krieger et al, "Enhancement of hepatitis C virus RNA replication by cell culture-adaptive mutations", J Virol, 2001,75, 4614-4624.

Lan et al "Mechanisms involved in the regulation of histone lysine demethylases". Current Opinion in Cell Biology, 2008,20, 316-325.

Lee et al, "Combinatorial lead optimization of [1,2]-diamines based on ethambutol as potential antiuberculosis preclinical candidates", J Comb Chem, 2003, 5(2), 172-187.

Lee et al, "Histone H3 lysine 4 demethylation is a target of nonselective antidepressive medicaitons",Chem Biol, 2006,13(6), 563-567.

Li et al, "Association between inflammatory mediators and angiographic orphologic features indicating thrombus formation in patients with acute myocardial infarction", Chin Med J, 2009,122(15), 1738-42.

Liang et al, "Inhibition of the histone demethylase LSD1 blocks alpha-herpesvirus lytic replication and reactivation from latency",Nat Med, 2009,15 (11), 1312-1317.

Lim et al, "Lysine-specific demethylase 1(LSD1) is highly expressed in ER-negative breast cancers and a biomarker predicting aggressive biology", Carcinogenesis,2010, 31(3), 512-20.

Lucerna et al, "Sustained expression of early growth response protein-1 blocks angiogenesis and tumor growth",Cancer Research,2006, 66,6708-6713.

Lupu Roxana, "Up-to-date in the hematological malignancies treatment", Maedica, 2006,1(1), 63-65.

Maclay et al, "Increased platelet activation in patients with stable and acute exacerbation of COPD", Thorax, 2011,66(9), 769-74.

Mannaioni et al, "Platelets and inflammation: role of platelet-derived growth factor, adhesion molecules and histamine", Inflamm Res, 1997,46(1), 4-18.

McNicol et al, "Beyong hemostatis: the role of platelets in inflammation, malignancy and infection",Cardiovascular & Haematological Disorders-Drug Targets, 2008,8, 99-117.

Meanwell, "Synopsis of some recent tatical application of bioisosteres in drug design", J Med Chem, 2011, 54(8),2529-91.

Metzger et al, "LSD1 demethylates repressive histone marks to promote androgen-receptor-dependent transcription",Nature,2005, 437(7057),436-9.

Mimasu et al "Crystal structure of histone demethylase LSD1 and tranylcypromine at 2.25 Å" Biochemical and Biophysical Research Communications ,2008,366, 15-22.

Mimasu et al, "Structurally designed trans-2-phenylcyclopropylamine derivatives potently inhibit histone demethylase LSD1/KDM1", Biochemistry,2010,49(30), 6494-6503.

Moritani et al, "Activation of platelets in bronchial asthma", Chest, 1998,113, 452-458.

Nabil Aboul-Enein et al, "Synthesis of some 4-substituted amino-1-methylpiperidines structurally related to antihistaminics", Pharmaceutica Acta Helvetiae, 1973, 48(3): 151-156.

Neelamegan et al, "Brain-penetrant LSD1 inhibitors can block memory consolidation", ACS Chem Neurosci, 2012, 3(2), 120-128.

Ogasawara et al, "Synthesis and biological activity of optically active NCL-1, a lysine-specific demethylase 1 selective inhibitor",Bioorg Med Chem, 2011, doi:10.1016/j.bmc.2010.12.024.

O'Sullivan et al, "The inflammatory role of platelets in cystic fibrosis", Am J Respir Crit Care Med, 2006,173, 483-90.

Pannala et al "Synthesis and structure-activity relationship of 4-(2-aryl-cyclopropylamino)-quinoline-3-carbonitriles as EGFR tyrosine kinase inhibitors". Bioorg & Med Chem Lett , 2007,17 (21), 5978-5082.

Pitchford et al, "Platelet P-selectin is required for pulmonary eosinophil and lymphocyte recruitment in a murine model of allergic inflammation", Blood, 2005,105, 2074-2081.

Pollock et al, Lysine-specific histone demethylase 1 inhibitors control breast cancer proliferation in ERalpha-dependent and -independent manners, ACS Chem Biol 2012,7,1221-1231.

Ravina et al, "The relationship between CAG repeat length and clinical progression in Huntington's disease", Movement Disorders,2008,23(9), 1223-7.

Reddy et al, "Role of lysine-specific demethylase 1 in the proinflammatory phenotype of vascular smooth muscle cells of diabetic mice", Circ Res,2008,103, 615-23.

Riley et al, "Absolute configuration of (+)- and (−)-trans-2-phenylcyclopropylamine hydrochloride",J Med Chem, 1972,15(11), 1187-1188.

Rinder et al, "Correlation of thrombosis with increased platelet turnover in thrombocytosis", Blood, 1998,91(4), 1288-1294.

Schmidt et al,"trans-2-phenylcyclopropylamine is a mechanism-based inactivator of the histone demethylase LSD1", Biochemistry, 2007,46(14),4408-4416.

Schulte et al, "Lysine-specific demethylase 1 is strongly expressed in poorly differentiated neuroblastoma: implications for therapy", Cancer Res,2009,69(5),2065-71.

Scoumanne et al "Protein methylation: a new mechanism of p53 tumor suppressor regulation" Histol Histopathol 2008,23, 1143-1149.

Scoumanne et al, "The lysine-specific demethylase 1 is required for cell proliferation in both p53-dependent and -independent manners", J Biol Chem, 2007,282(21), 15471-5.

Seligson et al, "Global histone modification patterns predict risk of prostate cancer recurrence",Nature, 2005,435, 1262-1266.

Seligson et al,"Global levels of histone modifications predict prognosis in different cancers",Am J Path, 2009,174,1619-28.

Sharma et al, "(Bis)urea and (bis)thiourea inhibitors of lysine-specific demethylase 1 as epigenetic modulators", J Med Chem, 2010,53(14), 5197-5212.

Shi et al,"Histone demethylation mediated by the nuclear amine oxidase homolog LSD1", Cell, 2004,119,941-953.

Shi, "Histone lysine demethylases: emerging roles in development, physiology and disease", Nature Reviews Genetics 2007, 8:829-833.

Stephens et al, "The determination of the absolute configurations of chiral molecules using vibrational circular dichroism (VCD) spectroscopy",Chirality, 2008,20(5), 643-663.

Stoffel et al, "Leukocyte count and risk of thrombosis in patients undergoing haematopoietic stem cell transplantation or intensive chemotherapy",Thromb Haemost, 2010,103(6), 1228-32.

Stratmann et al, "Pathobiology and cell interactions of platelets in diabetes", Diabetes & Vascular Disease Research,2005, 2(1), 16-23.

Szewczuk et al, "Mechanistic analysis of a suicide inactivator of histone demethylase LSD1", Biochemistry, 2007,46, 6892-6902.

Tamagawa-Mineoka et al, "Elevated platelet activation in patients with atopic dermatitis and psoriasis: increased plasma levels of beta-thromboglobulin and platelet factor 4", Allergology International,2008, 57, 391-396.

Taylor et al,"Roscovitine, a cyclin-dependent kinase inhibitor, prevents replication of varicella-zoster virus", J Virol, 2004,78, 2853-2862.

Thaulow et al, "Blood platelet count and function are related to total and cardiovascular death in apparently healtht men", Circulation, 1991,84, 613-617.

Ueda et al, "Identification of cell-active lysine specific demethylase 1-selective inhibitors",J Am Chem Soc, 2009,131(48), 17536-17537.

Vagner et al, "Peptidomimetics, a synthetic tool of drug discovery", Current Opinion on Chemical Biology, 2008, 12:292-296.

Wagner et al, "Platelets in inflammation and thrombosis", Arteriosclerosis, Thrombosis and Vascular Biology, 2003, 23, 2131-2137.

Wang et al, "Novel histone demethylase LSD1 inhibitors selectively target cancer cells with pluripotent stem cell properties," Cancer Research, 2011, 71(23):7238-49.

Wang et al "LSD1 Is a Subunit of the NuRD Complex and Targets the Metastasis Programs in Breast Cancer" Cell 2009, 138, 660-672.

(56) References Cited

OTHER PUBLICATIONS

Wang et al, "The lysine demethylase LSD1 (KDM1) is required for maintenance of global DNA methylation", Nature Genetics, 2009, 41(1), 125-129.
Weinreb et al, "Novel neuroprotective mechanism of action of rasagiline is associated with its propargyl moiety: interaction of Bcl-2 family members with PKC pathway", Ann NY Acad Sci, 2005,1053, 348-55.
Wermuth, "Molecular variations based on isosteric replacements", The Practice of Medicinal Chemistry (2nd edition), Academic Press, London, 2003, pp. 189-214.
Westland et al , "N-substituted derivatives of 2-aminoethanethiol and 2-hydraxinoethanethiol", JMedChem 1968, 11(4),824-829.
Whitlow et al,"Recruitment of the transcriptional coactivator HCF-1 to viral immediate-early promotoers during initiation of reactivation from latency of herpes simplex virus type 1", J Virol, 2009. 83(18):9591-5.
Willoughby et al, "Platelets and cardiovascular disease",Eur J Cardiovasc Nursing,2002,1, 273-288.
XP002568777 Database chemcats, database accession No. 2088922753, order No. kbsb-0063197, Aurora screening library, Aug. 20, 2009.
Yang et al "Structural Basis for the Inhibition of the LSD1 Histone Demethylase by the Antidepressant trans-2-Phenylcyclopropylamine" Biochemistry 2007,46 (27), 8058-8065.
Yang et al "Structural basis of histone demethylation by LSD1 revealed by suicide inactivation" Nature Structural & Molecular Biology 2007, 14(6), 535-539.
Yoshida et al, "Fluorinated phenylcyclopropylamines. Part 3: inhibition of monoamine oxidase A and B",Bioorg Med Chem,2004,12(10),2645-2652.
Youdim et al, "Bifunctional drug derivatives of MAO-B inhibitor rasagiline and iron chelator VK-28 as a more effective approach to treatment of brain ageing and ageing neurodegenerative diseases", Mechanisms of Ageing and Development, 2005, 126: 317-326.
F. Zaragoza Dörwald "Side reactions in Organic Synthesis: a guide to successful synthesis design" Wiley-VCH Verlag GmbH & Co, KGaA, Wilenheim, Chapter 1, 2005.
Zirkle et al, "2-substituted cyclopropylamines. II. Effect of structure upon monoamine oxidase-inhibitory activity as measured in vivo by potentiation of tryptamine convulsions", J Med Pharm Chem (ACS), 1962. 5, 1265-84.
"Definition of Cancer"—MedicineNetcom Medical references for patients, http://www.medterms.com, 2005.
Johnson et al, CAPLUS, Document No. 157:576967 "Preparation of cyclopropylamines as LSD1 inhibitors in the treatment of cancer", 2012.
Delorme et al, HCAPLUS, Document No. 132:49802, "Preparation of 1-(N-substituted aminomethyl)-4-guanidinomethylcyclohexanes useful in pain management", 1999.

CAS Registry No. RN220351-33-7, entered STN Mar. 11, 1999.
CAS Registry No. RN844655-03-4, entered STN Mar. 9, 2005.
CAS Registry No. RN846596-02-9, entered STN Mar. 22, 2005.
CAS Registry No. RN848204-13-7, entered STN Apr. 11, 2005.
CAS Registry No. RN848732-87-6, entered STN Apr. 19, 2005.
CAS Registry No. RN848742-47-2, entered STN Apr. 19, 2005.
CAS Registry No. RN848753-47-9, entered STN Apr. 19, 2005.
CAS Registry No. RN903487-42-3, entered STN Aug. 23, 2006.
CAS Registry No. RN918305-55-2, entered STN Jan. 24, 2007.
CAS Registry No. RN959071-98-8, entered STN Dec. 20, 2007.
CAS Registry No. RN1026299-47-7, entered STN Jun. 8, 2008.
CAS Registry No. RN1157140-28-7, entered STN Jun. 14, 2009.
CAS Registry No. RN1218057-33-0, entered STN Apr. 11, 2010.
CAS Registry No. RN1247584-27-7, entered STN Oct. 27, 2010.
CAS Registry No. RN1247717-42-5, entered STN Oct. 27, 2010.
CAS Registry No. RN1247999-77-4, entered STN Oct. 28, 2010.
CAS Registry No. RN1248611-33-7, entered STN Oct. 29, 2010.
CAS Registry No. RN1248913-30-5, entered STN Nov. 1, 2010.
CAS Registry No. RN1248971-98-3, entered STN Nov. 1, 2010.
CAS Registry No. RN1250045-89-6, entered STN Nov. 1, 2010.
CAS Registry No. RN1250199-20-2, entered STN Nov. 1, 2010.
CAS Registry No. RN1250332-49-0, entered STN Nov. 1, 2010.
CAS Registry No. RN1251130-23-0, entered STN Nov. 3, 2010.
CAS Registry No. RN1270634-53-1, entered STN Mar. 27, 2011.
CAS Registry No. RN1273738-91-2, entered STN Apr. 3, 2011.
CAS Registry No. RN1274124-27-4, entered STN Apr. 3, 2011.
CAS Registry No. RN1274681-54-7, entered STN Apr. 4, 2011.
CAS Registry No. RN1280568-04-8, entered STN Apr. 15, 2011.
CAS Registry No. RN1280602-35-8, entered STN Apr. 15, 2011.
CAS Registry No. RN1281516-77-5, entered STN Apr. 17, 2011.
CAS Registry No. RN1281556-75-9, entered STN Apr. 17, 2011.
CAS Registry No. RN1281596-19-7, entered STN Apr. 17, 2011.
CAS Registry No. RN1281615-78-8, entered STN Apr. 17, 2011.
CAS Registry No. RN1281856-83-4, entered STN Apr. 18, 2011.
CAS Registry No. RN1281886-96-1, entered STN Apr. 18, 2011.
CAS Registry No. RN1282014-65-6, entered STN Apr. 18, 2011.
Co-pending U.S. Appl. No. 13/580,553, filed Aug. 22, 2012.
Co-pending U.S. Appl. No. 13/983,844, filed Aug. 6, 2013.
Co-pending U.S. Appl. No. 14/118,323, filed Nov. 18, 2013.
Co-pending U.S. Appl. No. 14/118,330, filed Nov. 18, 2013.
Co-pending U.S. Appl. No. 14/096,557, filed Dec. 4, 2013.
Co-pending U.S. Appl. No. 14/184,745, filed Feb. 20, 2014.
Co-pending U.S. Appl. No. 14/352,711, filed Apr. 18, 2014.
Co-pending U.S. Appl. No. 14/352,719, filed Apr. 18, 2014.
Co-pending U.S. Appl. No. 14/627,333, filed Feb. 20, 2015.
Co-pending U.S. Appl. No. 14/640,395, filed Mar. 6, 2015.
Co-pending U.S. Appl. No. 14/675,990, filed Apr. 1, 2015.
Co-pending U.S. Appl. No. 14/711,156, filed May 13, 2015.
Co-pending U.S. Appl. No. 14/548,649, filed Sep. 9, 2015.
International Search Report and Written Opinion of the International Searching Authority for International Application No. PCT/EP2011/056279, dated Aug. 11, 2011.

* cited by examiner

LYSINE SPECIFIC DEMETHYLASE-1 INHIBITORS AND THEIR USE

This is a continuation of application Ser. No. 14/228,083, filed Mar. 27, 2014, which is a divisional application of application Ser. No. 13/641,916, filed Dec. 21, 2012, which is a national stage application of International Patent Application No. PCT/EP2011/056279, filed Apr. 19, 2011, which was published in English as WO 2011/131/697 A1 on Oct. 27, 2011, and claims the benefit of the Apr. 19, 2010, filing date of European Patent Application No. 10160315.7, all of which are incorporated herein by reference.

FIELD OF THE INVENTION

The invention relates to compounds and their use in therapy.

BACKGROUND OF THE INVENTION

Cancer is prevalent: there were about 3.2 million cancer cases diagnosed (53% men, 47% women) and 1.7 million deaths from cancer (56% men, 44% women) in Europe (Ferlay et al. (2007) *Ann. Oncol.* 18(3):581-92). In the United States, the probability of developing invasive cancer is 38% for females and 46% for males that live to be 70 years old and older. In the US about 1.4 million new cases of cancer are expected for 2006. Although the five year survival rate for cancer is now 65%, up from about 50% in the mid-nineteen seventies, cancer is deadly. It was estimated that 565,000 people in the United States would die from cancer in 2006 (American Cancer Society, Surveillance Research, 2006). Despite tremendous advances in cancer treatment and diagnosis, cancer remains a major public health concern. Accordingly, there is a need for new therapeutics with activity in cancer.

Another health crisis is facing industrialized nations. As the population in these countries age, neurodegenerative diseases are affecting more and more people, posing a tremendous economic burden to national health systems. Alzheimer's disease is the largest neurodegenerative disease; disease modifying drugs have long been sought, but to-date, none have been identified. Other neurodegenerative conditions include Parkinson's disease, Huntington's disease, Lewy Body dementia, and which are all characterized by disease progression which robs the patients of their ability to perform normal daily activities, eventually leading to death.

One similar characteristic amongst many cancers and neurodegenerative diseases is aberrant gene expression. A number of compounds have been shown to alter gene expression, including histone deacetylase inhibitors which alter the histone acetylation profile of chromatin. Histone deacetylase inhibitors like SAHA, TSA, and many others have been shown to alter gene expression in various in vitro and in vivo animal models. Another modification that is involved in regulating gene expression is histone methylation. Histones can be subject to numerous modifications including lysine and arginine methylation. The methylation status of histone lysines has recently been shown to be important in dynamically regulating gene expression.

A group of enzymes known as histone lysine methyl transferases and histone lysine demethylases are involved histone lysine modifications. One particular human histone lysine demethylase enzyme called Lysine Specific Demethylase-1 (LSD1) was recently discovered (Shi et al. (2004) *Cell* 119:941) to be involved in this crucial histone modification. Inactivation of LSD1 in *Drosophila* (dLSD1) strongly affects the global level of mono and dimethyl-H3-K4 methylation but not methyl-H3K9 while the levels of some other histone methylation and acetylation marks remained the same. LSD1 inactivation resulted in elevated expression of a subset of genes, including neuronal genes in non-neuronal cells analogous to the functions of LSD1 in human cells. In *Drosophila*, dLSD1 is not an essential gene, but animal viability is strongly reduced in mutant animals in a gender specific manner (Destefano et al. (2007) *Curr. Biol.* 17(9):808-12). Mouse homozygous LSD1 knock-outs were embryonic lethal.

LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen carbon bonds. Recent experiments with LSD1 have shown that it is involved in diverse process such as carcinogenesis (Kahl et al. (2006) *Cancer Res.* 66:1341-11347) and vascular inflammation (Reddy et al. (2008) *Circ. Res.* 103:615). It was found that a commercially available antidepressant, Parnate®, which targets monoamine oxidase (MAO), also inhibits LSD1 at clinically relevant concentrations (Lee et al. (2006) *Chem. Biol.* 13:563-567). Schmidt et al. found "$IC_{50}$ values for 2-PCPA of 20.7±2.1 µM for LSD1, 2.3±0.2 µM for MAO A, and 0.95±0.07 µM for MAO B." See Schmidt et al. (2007) *Biochemistry* 46(14)4408-4416. Thus, Parnate (2-PCPA) is a better inhibitor of MAO-A and MAO-B as compared to LSD1. Schmidt et al. note that the IC50 values for irreversible inhibitors of LSD1 like parnate can greatly depend on assay conditions. Additionally, derivatives of Parnate also can inhibit LSD1 (Gooden et al. (2008) *Bioorg. Med. Chem. Let.* 18:3047-3051). Another class of compounds was recently disclosed to inhibit LSD1 activity: polyamines (Huang et al. (2007) *PNAS* 104:8023-8028). These polyamines inhibit LSD1 modestly and were shown to cause the re-expression of genes aberrantly silenced in cancer cells.

LSD1 is also involved in regulating the methylation of lysines of some proteins which are not histones, like P53 and DNMT1 which both have critical roles in cancer.

Lee et al. ((2006) *Chem. Biol.* 13:563-567) reported that tranylcypromine inhibits histone H3K4 demethylation and can derepress Egr1 gene expression in some cancer lines. A body of evidence is accumulating that Egr-1 is a tumor suppressor gene in many contexts. Calogero et al. ((2004) *Cancer Cell International* 4:1) reported that Egr-1 is downregulated in brain cancers and exogenous expression of Egr-1 resulted in growth arrest and eventual cell death in primary cancer cell lines. Lucerna et al. ((2006) *Cancer Research* 66, 6708-6713) showed that sustained expression of Egr-1 causes antiangiogenic effects and inhibits tumor growth in some models. Ferraro et al. ((2005) *J. Clin. Oncol. March* 20; 23(9):1921-6) reported that Egr-1 is downregulated in lung cancer patients with a higher risk of recurrence and may be more resistant to therapy. Scoumanne et al. ((2007) *J Biol Chem. May* 25; 282(21):15471-5) observed that LSD1 is required for cell proliferation. They found that deficiency in LSD1 leads to a partial cell cycle arrest in G2/M and sensitizes cells to growth suppression induced by DNA damage. Kahl et al. ((2006) *Cancer Res.* 66(23): 11341-7) found that LSD1 expression is correlated with prostate cancer aggressiveness. Metzger et al. ((2005) *Nature* 15:437(7057):436-9) reported that LSD1 modulation by siRNA and pargyline regulates androgen receptor (AR) and may have therapeutic potential in cancers where AR plays a role, like prostate, testis, and brain cancers. Thus, a body of evidence has implicated LSD1 in a number of cancers, which suggests that LSD1 is a therapeutic target for cancer.

The phenylcyclopropylamines have been the subject of many studies designed to elucidate a SAR for MAO inhibition. Kaiser et al. ((1962) *J. Med. Chem.* 5:1243-1265); Zirkle et al. ((1962) *J. Med. Chem.* 1265-1284; U.S. Pat. Nos. 3,365,458; 3,471,522; 3,532,749) have disclosed the synthesis and activity of a number of phenylcyclopropylamine related compounds. Zirkle et al. ((1962) *J. Med. Chem.* 1265-1284) reported that mono- and disubstitution of the amino group of trans-2-phenylcyclopropylamine with methyl decreases the activity only slightly whereas monosubstitution with larger groups like alkyl and aralkyl groups results in considerable loss of activity in the tryptamine potentiation assay for MAO activity. Studies have also been conducted with phenylcyclopropylamine related compounds to determine selectivity for MAO-A versus MAO-B since MAO-A inhibitors can cause dangerous side-effects (see e.g., Yoshida et al. (2004) *Bioorg. Med Chem.* 12(10):2645-2652; Hruschka et al. (2008) *Biorg Med Chem.* (16):7148-7166; Folks et al. (1983) *J. Clin. Psychopharmacol.* (3)249; and Youdim et al. (1983) *Mod. Probl. Pharmacopsychiatry* (19):63). Other phenylcyclopropylamine type compounds are disclosed in Bolesov et al. ((1974) *Zhurnal Organicheskoi Khimii* 10:8 1661-1669) and Russian. Patent No. 230169 (19681030). Gooden et al. ((2008) *Bioorg. Med. Chem. Let.* 18:3047-3051) describe the synthesis of phenylcyclopropylamines derivatives and analogs as well as their activity against MAO-A, MAO-B, and LSD1. None of the compound made in Gooden et al. showed a lower Ki for LSD1 as compared to either MAO A or MAO B. Additionally, most of the Gooden et al. phenylcyclopropylamine derivatives were better inhibitors of MAO-A as compared to MAO-B.

In view of the lack of adequate treatments for conditions such as cancer, there is a desperate need for disease modifying drugs and drugs that work by inhibiting novel targets. There is a need for the development of LSD1 selective inhibitors particularly those which selectively inhibit LSD1.

BRIEF SUMMARY OF THE INVENTION

The present invention relates to the identification of compounds and their use in treating or preventing diseases. The present invention provides a compound of Formula 1 or a pharmaceutically acceptable salt or solvate thereof, a pharmaceutical composition comprising a compound of Formula 1 or a pharmaceutically acceptable salt or solvate thereof, and a pharmaceutically acceptable carrier, and their use for treating or preventing disease. One use of a compound of Formula 1 is for treating or preventing cancer. Another use of a compound of Formula 1 is to inhibit LSD1. The present invention thus relates to a compound of Formula 1 or an enantiomer, a diastereomer, or a mixture thereof, or a pharmaceutically acceptable salt or solvate thereof for use in treating or preventing cancer. The invention also relates to screening methods for identifying substituted heteroaryl and aryl cyclopropylamines that are selective LSD1 inhibitors and their use in treating or preventing disease.

In a first aspect, the invention provides a compound of Formula 1 or an enantiomer, a diastereomer, or a mixture thereof, or a pharmaceutically acceptable salt or solvate thereof:

$$(A')_X\text{-}(A)\text{-}(B)\text{---}(Z)\text{-}(L)\text{-}(D) \qquad 1$$

wherein:
(A) is a heteroaryl or aryl covalently bonded to (B) and to (A') if present;
each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, haloalkoxy, aryl, arylalkoxy, alkyl, alkoxy, amide, —CH$_2$C(=O)NH$_2$, heteroaryl, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to (L) or to (D) when (L) is a single bond, and to a hydrogen atom;
(L) is a linker which links (Z) and (D), wherein said linker is chosen from a single bond, —CH$_2$—, —CH$_2$CH$_2$—, —CH$_2$CH$_2$CH$_2$—, and —CH$_2$CH$_2$CH$_2$CH$_2$—;
(D) is an aliphatic carbocyclic group or benzocycloalkyl, wherein said aliphatic carbocyclic group or said benzocycloalkyl is covalently bonded to (L) or to (Z) when (L) is a single bond, and wherein (D) has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), amido, alkyl, halo, cyano, alkoxy, haloalkyl, and haloalkoxy;
with the proviso that the following compounds are excluded:
N-(2-phenylcyclopropyl)-cyclopentanamine;
10,11-dihydro-N-(2-phenylcyclopropyl)-5H-dibenzo[a,d]cyclohepten-5-amine; and trans-N-(2-phenylcyclopropyl)-cyclohexanamine.

In a related aspect, the invention provides a pharmaceutical composition comprising a compound of Formula 1 or an enantiomer, a diastereomer, or a mixture thereof, or a pharmaceutically acceptable salt or solvate thereof as defined above and a pharmaceutically acceptable carrier. Preferred embodiments of the compound of Formula 1 for use in the composition of this first aspect are defined herein below in this first aspect of the invention and as described in the Detailed Description of the Invention.

In one embodiment of this first aspect, the invention provides a compound of Formula 1 or an enantiomer, a diastereomer, or a mixture thereof, or a pharmaceutically acceptable salt or solvate thereof:

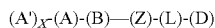

$$(A')_X\text{-}(A)\text{-}(B)\text{---}(Z)\text{-}(L)\text{-}(D) \qquad 1$$

wherein:
(A) is a heteroaryl or aryl group covalently bonded to (B) and to (A') if present;
each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, and cyano, wherein (A') is substituted with 0, 1, 2, or 3 substituents independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to (L) or to (D) when (L) is a single bond, and to a hydrogen atom;

(L) is a linker which links (Z) and (D), wherein said linker is chosen from a single bond, —CH$_2$—, —CH$_2$CH$_2$—, —CH$_2$CH$_2$CH$_2$—, and —CH$_2$CH$_2$CH$_2$CH$_2$—;

(D) is cycloalkyl covalently bonded to (L) or to (Z) when (L) is a single bond, and (D) has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy;

with the proviso that the following compounds are excluded:
  N-(2-phenylcyclopropyl)-cyclopentanamine;
  trans-N-(2-phenylcyclopropyl)-cyclohexanamine.

In another embodiment of this first aspect, the invention provides a compound of Formula 1 or an enantiomer, a diastereomer, or a mixture thereof, or a pharmaceutically acceptable salt or solvate thereof:

$$(A')_{X}\text{-}(A)\text{-}(B)\text{—}(Z)\text{-}(L)\text{-}(D) \qquad 1$$

wherein:
(A) is a heteroaryl or aryl group covalently bonded to (B) and to (A') if present;

each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, and cyano, wherein (A') is substituted with 0, 1, 2, or 3 substituents independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl;

X is 0, 1, 2, or 3;

(B) is a cyclopropyl ring which is covalently bonded to (A) and to (Z), wherein (A) and (Z) are covalently bonded to different carbon atoms of (B);

(Z) is —NH—; accordingly, (Z) is a nitrogen atom covalently bonded to (B), to (D), and to a hydrogen atom;

(L) is a linker which is a single covalent bond that links (Z) to (D);

(D) is benzocycloalkyl covalently bonded to (Z), and (D) has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy;

with the proviso that the following compound is excluded:
  10,11-dihydro-N-(2-phenylcyclopropyl)-5H-dibenzo[a,d]cyclohepten-5-amine.

In a related aspect, the invention provides a pharmaceutical composition comprising a compound of Formula 1 or an enantiomer, a diastereomer, or a mixture thereof, or a pharmaceutically acceptable salt or solvate thereof as defined above in the first aspect of the invention or an embodiment thereof and a pharmaceutically acceptable carrier.

In a second aspect, the invention provides a method of treating or preventing a disease or condition comprising administering, to a patient (preferably a human) in need of treatment or prevention, a therapeutically effective amount of a pharmaceutical composition comprising a compound of Formula 1 as defined above in the first aspect of the invention or an embodiment thereof as described above or an enantiomer, a diastereomer, or a mixture thereof, or a pharmaceutically acceptable salt or solvate thereof and a pharmaceutically acceptable carrier. This aspect of the invention also relates to a compound of Formula 1 for use as a medicament.

In a third aspect, the invention provides a method of inhibiting LSD1 activity comprising administering, to a patient (preferably a human) in need of treatment, a therapeutically effective amount of a composition comprising a compound of Formula 1 or an enantiomer, a diastereomer, or a mixture thereof, or a pharmaceutically acceptable salt or solvate thereof:

$$(A')_{X}\text{-}(A)\text{-}(B)\text{—}(Z)\text{-}(L)\text{-}(D) \qquad 1$$

wherein:
(A) is a heteroaryl or aryl covalently bonded to (B) and to (A') if present; each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl;

X is 0, 1, 2, or 3;

(B) is a cyclopropyl ring which is covalently bonded to (A) and to (Z), wherein (A) and (Z) are covalently bonded to different carbon atoms of (B);

(Z) is —NH—; accordingly, (Z) is a nitrogen atom covalently bonded to (B), to (L) or to (D) when (L) is a single bond, and to a hydrogen atom;

(L) is a linker which links (Z) and (D), wherein said linker is chosen from a single bond, —CH$_2$—, —CH$_2$CH$_2$—, —CH$_2$CH$_2$CH$_2$—, and —CH$_2$CH$_2$CH$_2$CH$_2$—;

(D) is an aliphatic carbocyclic group or benzocycloalkyl, wherein said aliphatic carbocyclic group or said benzocycloalkyl is covalently bonded to (L) or to (Z) when (L) is a single bond, and wherein (D) has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy, and a pharmaceutically acceptable carrier in an amount sufficient to inhibit LSD1 activity. This aspect can be reformulated as a compound of Formula 1 as herein defined for use as a LSD1 inhibitor. This aspect can also be reformulated as a compound of Formula 1 for use in the treatment of a disease associated to LSD1. In a related aspect, a method for treating an individual (preferably a human) is provided, said method comprising identifying an individual in need of treatment and administering to said individual a therapeutically effective amount of a compound of Formula 1. In a preferred aspect, the therapeutically effective amount of a compound of Formula 1 is an amount sufficient to inhibit LSD1. Preferred embodiments of the compounds of Formula 1 for use in the composition and method of this third aspect of the invention are as defined herein above in the first aspect of the invention.

In a fourth aspect, the invention provides a method of treating or preventing cancer comprising administering, to a patient (preferably a human) in need of treatment or prevention, a therapeutically effective amount of a pharmaceutical composition comprising a compound of Formula 1 as defined above in the first aspect of the invention or an enantiomer, a diastereomer, or a mixture thereof, or a pharmaceutically acceptable salt or solvate thereof, and a pharmaceutically acceptable carrier. This aspect of the invention also relates to a compound of Formula 1 as defined above in the first aspect of the invention or an enantiomer, a diastereomer, or a mixture thereof, or a pharmaceutically acceptable salt or solvate thereof for use in treating or preventing cancer. Preferably, the cancer is chosen from breast cancer, colorectal cancer, lung cancer, prostate cancer, testicular cancer, brain cancer, skin cancer, and blood cancer. In a preferred aspect, the therapeutically effective amount of a compound of Formula 1 is an amount sufficient to inhibit LSD1.

In a fifth aspect, the invention provides a method for identifying a compound which is a selective inhibitor of LSD1, the method comprising selecting or providing a compound which is a substituted heteroarylcyclopropylamine or a substituted arylcyclopropylamine, and determining the ability of the compound to inhibit LSD1 and MAO-A and/or MAO-B, wherein a compound that inhibits LSD1 to a greater extent than MAO-A and/or MAO-B is identified as a LSD1 selective inhibitor. Furthermore, the method of this aspect is useful for identifying dual inhibitors of LSD1 and MAO-B which are compounds that inhibit LSD1 and MAO-B to a greater extent than MAO-A.

According to this fifth aspect of the invention, a substituted heteroarylcyclopropylamine or a substituted arylcyclopropylamine is defined as follows in Formula 2:

(R3)-(W)-(cyclopropyl)-(NH)-(L')-(R4)    2 wherein:
(R3) is present or not present, when present (R3) is chosen from arylalkyl, arylalkoxy, heterocyclylalkyl, and heterocyclylalkoxy, wherein said (R3) group has 0, 1, 2, or 3 substituents independently chosen from halo, alkyl, alkoxy, carbocyclyl, cycloalkyl, cycloalkoxy, haloalkyl, haloalkoxy, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heterocyclyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, and said (R3) group is covalently bonded to (W);
(W) is an aryl or heteroaryl group covalently bonded to (R3) and to (cyclopropyl), wherein said (W) has 0, 1, or 2 substituents, not including (R3) and (cyclopropyl), wherein said substituents on (W) are independently chosen from halo, alkyl, alkoxy, carbocyclyl, cycloalkyl, cycloalkoxy, haloalkyl, haloalkoxy, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heterocyclyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
(cyclopropyl) is a cyclopropyl group covalently bonded to (W) and to the nitrogen atom of (NH);
(NH) is a —NH— group (nitrogen covalently bonded to a hydrogen atom) wherein the nitrogen is covalently bonded to (cyclopropyl) and to (L'), or if n=0 then (L') is a single bond and the nitrogen of —NH— is covalently bonded to (R4);
(L') is a linker of formula —(CH$_2$)$_n$— where n is chosen from 0, 1, 2, 3, 4, 5, or 6, wherein (L') is covalently bonded to the nitrogen of (NH) and to (R4) or (L') is a single bond which covalently links (NH) and (R4) when n is 0; and
(R4) is an aliphatic carbocyclic group or benzocycloalkyl, wherein said aliphatic carbocyclic group or said benzocycloalkyl is covalently bonded to (L') or to the nitrogen of (NH) when (L') is a single bond, wherein said (R4) group has 0, 1, 2, or 3 substituents independently chosen from halo, alkyl, alkoxy, carbocyclyl, cycloalkyl, cycloalkoxy, haloalkyl, haloalkoxy, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heterocyclyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

According to the fifth aspect of the invention, a compound of Formula 2 is provided which is a selective LSD1 inhibitor. The selective LSD1 inhibitor as identified by the method of this embodiment can be used to prepare a pharmaceutical composition comprising a therapeutically effective amount of said selective LSD1 inhibitor of Formula 2, or a pharmaceutically acceptable salt or solvate thereof, and a pharmaceutically acceptable carrier. The pharmaceutical composition can be administered to an individual in need of such treatment. Accordingly, the invention also relates to a method of treating or preventing a disease or condition, the method comprising administering, to a patient (preferably a human) in need of treatment or prevention, a therapeutically effective amount of a pharmaceutical composition comprising said selective LSD1 inhibitor of Formula 2 and a pharmaceutically acceptable carrier. According to this embodiment, the therapeutically effective amount is an amount sufficient to inhibit LSD1 selectively.

Thus, the invention provides a pharmaceutical composition comprising a pharmaceutically acceptable carrier and a compound of Formula 1 or 2 which is a selective inhibitor of LSD1. LSD1 selective inhibitors have Ki values for LSD1 which are at least 2-fold lower than the Ki value for MAO-A and/or MAO-B. In one aspect of this embodiment, the LSD1 Ki value is at least 5-fold lower than the Ki value for MAO-A and/or MAO-B. In one aspect of this embodiment, the LSD1 Ki value is at least 10-fold lower than the Ki value for MAO-A and/or MAO-B. In one embodiment of the invention, the pharmaceutical composition comprising a LSD1 selective inhibitor of Formula 1 or 2, or a pharmaceutically acceptable salt or solvate thereof is useful for treating and/or preventing a disease in an individual. In one aspect, a therapeutically effective amount of the composition is administered to individual in an amount sufficient to prevent or treat a disease. In a more specific aspect, the disease is cancer. In an even more specific aspect, the disease is a cancer chosen from prostate, testicular, brain, colorectal, lung, breast, skin, and blood cancer. In one specific aspect, the cancer is prostate cancer. In one specific aspect, the cancer is lung cancer. In one specific aspect, the cancer is brain cancer. In one specific aspect, the cancer is blood cancer (e.g., leukemia). In one specific aspect, the cancer is breast cancer. In one specific aspect, the cancer is colorectal cancer.

According to the fifth aspect of the invention, a compound of Formula 2 is provided which is a dual inhibitor of LSD1 and MAO-B. The dual LSD1/MAO-B inhibitor as identified by the method of this embodiment can be used to prepare a pharmaceutical composition comprising a therapeutically effective amount of said dual LSD1/MAO-B inhibitor of Formula 2, or a pharmaceutically acceptable salt or solvate thereof, and a pharmaceutically acceptable carrier. The pharmaceutical composition can be administered to an individual in need of such treatment. According to this embodiment, the therapeutically effective amount is an amount sufficient to inhibit MAO-B and LSD1.

Thus, the invention provides a pharmaceutical composition comprising a pharmaceutically acceptable carrier and a compound of Formula 1 or 2 that is a dual inhibitor of LSD1 and MAO-B. Preferably, LSD1/MAO-B dual inhibitors have Ki values for LSD1 and MAO-B that are at least 2-fold lower than the Ki value for MAO-A. In one aspect of this embodiment, the LSD1 and MAO-B Ki values are at least 5-fold lower than the Ki value for MAO-A. In one aspect of this embodiment, the LSD1 and MAO-B Ki values are at least 10-fold lower than the Ki value for MAO-A.

Compounds of Formula 1 or 2 that have MAO-B inhibitory activity are contemplated to be useful for diseases where MAO-B is therapeutically desirable like depression and neurodegenerative diseases including Alzheimer's disease, Parkinson's disease and Huntington's disease.

Recent studies have furthermore implicated LSD1 in viral infection and reactivation. In particular it was shown that pharmacological inhibitors of LSD1 like parnate and siRNA knock down of LSD1 caused reduced viral infectivity and reduced reactivation after latency (Liang et al. (2009) *Nat. Med.* 15:1312-1317). Therefore it is believed that the compounds of the invention, including the compounds of Formula 1 as defined and described herein, can be used for treating or preventing viral infection. Furthermore, it is believed that the compounds of the invention can be used for treating or preventing viral reactivation after latency.

Thus, in one embodiment, the invention provides a method for treating or preventing a viral infection, the method comprising administering, to a patient/individual (preferably a human) in need of treatment or prevention, a therapeutically effective amount of a compound of Formula 1 as defined above in any of the aspects and embodiments of the invention or a pharmaceutically acceptable salt or solvate thereof, or a pharmaceutical composition comprising any of the aforementioned compounds and a pharmaceutically acceptable carrier. Accordingly, the invention also provides a compound of Formula 1 as defined above in any of the aspects and embodiments of the invention or a pharmaceutically acceptable salt or solvate thereof, or a pharmaceutical composition comprising any of the aforementioned compounds and a pharmaceutically acceptable carrier, for use in treating or preventing a viral infection. In a preferred embodiment, the viral infection is a herpesvirus infection. In an even more preferred embodiment, the herpesvirus infection is caused by and/or associated with a herpesvirus chosen from HSV-1, HSV-2, and Epstein-Barr virus. In one aspect of this embodiment, the viral infection is caused by and/or associated with HIV.

In one embodiment, the invention provides a method for treating or preventing viral reactivation after latency, the method comprising administering, to a patient/individual (preferably a human) in need of treatment or prevention, a therapeutically effective amount of a compound of Formula 1 as defined above in any of the aspects and embodiments of the invention or a pharmaceutically acceptable salt or solvate thereof, or a pharmaceutical composition comprising any of the aforementioned compounds and a pharmaceutically acceptable carrier. Accordingly, the invention also provides a compound of Formula 1 as defined above in any of the aspects and embodiments of the invention or a pharmaceutically acceptable salt or solvate thereof, or a pharmaceutical composition comprising any of the aforementioned compounds and a pharmaceutically acceptable carrier, for use in treating or preventing viral reactivation after latency. In a preferred embodiment, the virus that is reactivating is a herpesvirus. In an even more preferred embodiment, the herpesvirus that is reactivating is chosen from HSV-1, HSV-2, and Epstein-Barr virus. In one aspect of this embodiment, the virus that is reactivating is HIV.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The present invention relates to the identification of compounds and their use in treating and preventing diseases. The present invention provides compounds of Formula 1, pharmaceutical compositions comprising a compound of Formula 1 or a pharmaceutically acceptable salt or solvate thereof and a pharmaceutically acceptable carrier, and their use for treating diseases. One use of the compounds of Formula 1 is for treating cancer. The compounds of Formula 1 can be used as LSD1 selective inhibitors that inhibit LSD1 to a greater extent than MAO-A and MAO-B. Some compounds of the invention inhibit LSD1 and MAO-B to a greater extent than MAO-A. In particular it was found that phenylcyclopropylamine derivatives of Formula 1 yield compounds with unexpectedly potent LSD1 inhibition. The Examples described herein show that all of the Example compounds of Formula 1 (e.g., Examples 1-16) have Ki (1050) values for LSD1 inhibition under 1000 nanomolar (see Table 1) and many have Ki (TC50) values under 500 nanomolar, which makes them about at least 40 to 50-fold or more potent than tranylcypromine for LSD1 inhibition. These compounds are LSD1 selective in that they inhibit LSD1 to an extent greater than they inhibit MAO-A and MAO-B.

In a first aspect, the invention provides a compound of Formula 1 or an enantiomer, a diastereomer, or a mixture thereof, or a pharmaceutically acceptable salt or solvate thereof:

$$(A')_{X}\text{-}(A)\text{-}(B)\text{---}(Z)\text{-}(L)\text{-}(D) \qquad 1$$

wherein:
(A) is a heteroaryl or aryl covalently bonded to (B) and to (A') if present; each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, and cyano, wherein (A') is substituted with 0, 1, 2, or 3 substituents independently chosen from halo, haloalkyl, haloalkoxy, aryl, arylalkoxy, alkyl, alkoxy, amido, —$CH_2C(=O)NH_2$, heteroaryl, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is a nitrogen atom covalently bonded to (B), to (L), and to a hydrogen atom;
(L) is a linker which links (Z) and (D), wherein said linker is chosen from a single bond, —$CH_2$—, —$CH_2CH_2$—, —$CH_2CH_2CH_2$—, and —$CH_2CH_2CH_2CH_2$—;
(D) is an aliphatic carbocyclic group or benzocycloalkyl, wherein said aliphatic carbocyclic group or said benzocycloalkyl is covalently bonded to (L) or to (Z) when (L) is a single bond, and wherein (D) has from 0, 1, 2, or 3 substituents independently chosen from —$NH_2$, —NH($C_1$-

$C_6$ alkyl), —N($C_1$-$C_6$ alkyl)($C_1$-$C_6$ alkyl), alkyl, halo, amido, cyano, alkoxy, haloalkyl, and haloalkoxy;

with the proviso that the following compounds are excluded:

N-(2-phenylcyclopropyl)-cyclopentanamine;

10,11-dihydro-N-(2-phenylcyclopropyl)-5H-dibenzo[a,d] cyclohepten-5-amine; and trans-N-(2-phenylcyclopropyl)-cyclohexanamine.

In a related aspect, the invention provides a pharmaceutical composition comprising a compound of Formula 1 or a pharmaceutically acceptable salt or solvate thereof as defined above and a pharmaceutically acceptable carrier. Preferred embodiments of the compound of Formula 1 for use in the composition of this first aspect are defined herein below in this first aspect of the invention.

In one embodiment of the first aspect, the invention provides a compound of Formula 1 or a pharmaceutically acceptable salt or solvate thereof, wherein (A) is an aryl group and the other variables are as defined above in the broadest definition of the first aspect of the invention. In a preferred embodiment, (A) is phenyl. In another preferred embodiment, (A) is naphthyl.

In one embodiment of the first aspect, the invention provides a compound of Formula 1 or a pharmaceutically acceptable salt or solvate thereof, wherein (A) is a phenyl group and the other variables are as defined above in the broadest definition of the first aspect of the invention or as defined in one of the other embodiments of the first aspect of the invention. In a preferred embodiment, (A) is a phenyl group having 0, 1, 2, or 3 substituents (A') independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, haloalkoxy, aryl, arylalkoxy, alkyl, alkoxy, amido, —$CH_2C$(=O)$NH_2$, heteroaryl, cyano, sulfonyl, and sulfinyl. In another preferred embodiment, (A) is a phenyl group having 1, 2, or 3 substituents (A') independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, haloalkoxy, aryl, arylalkoxy, alkyl, alkoxy, amido, —$CH_2C$(=O)$NH_2$, heteroaryl, cyano, sulfonyl, and sulfinyl.

In one embodiment of the first aspect, the invention provides a compound of Formula 1 or a pharmaceutically acceptable salt or solvate thereof, wherein X is 1 or 2 and the other variables are as defined above in the broadest definition of the first aspect of the invention or as defined in one of the other embodiments of the first aspect of the invention. In a preferred embodiment, the 1 or 2 (A') groups are independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, haloalkoxy, aryl, arylalkoxy, alkyl, alkoxy, amido, —$CH_2C$(=O)$NH_2$, heteroaryl, cyano, sulfonyl, and sulfinyl. In a more preferred embodiment, the 1 or 2 (A') groups are independently chosen from aryl and arylalkoxy wherein said (A') have 0, 1, or 2 substituents independently chosen from halo, haloalkyl, haloalkoxy, aryl, arylalkoxy, alkyl, alkoxy, amido, —$CH_2C$(=O)$NH_2$, heteroaryl, cyano, sulfonyl, and sulfinyl. In an even more preferred embodiment, the 1 or 2 (A') groups are independently chosen from phenyl, benzyloxy, and phenethyloxy, wherein said (A') has 0, 1, or 2 substituents independently chosen from halo, haloalkyl, alkyl, alkoxy, amido, —$CH_2C$(=O)$NH_2$, heteroaryl, cyano, sulfonyl, and sulfinyl.

In one embodiment of the first aspect, the invention provides a compound of Formula 1 or a pharmaceutically acceptable salt or solvate thereof, wherein X is 1; and (A') is chosen from aryl and arylalkoxy wherein said aryl or arylalkoxy group has 0 or 1 substituent chosen from halo and haloalkyl and the other variables are as defined above in the broadest definition of the first aspect of the invention or as defined in one of the other embodiments of the first aspect of the invention. In one preferred embodiment, said (A') group has 1 substituent chosen from halo and haloalkyl. In another preferred embodiment, said (A') group is not substituted.

In one embodiment of the first aspect, the invention provides a compound of Formula 1 or a pharmaceutically acceptable salt or solvate thereof, wherein (A) is a heteroaryl and the other variables are as defined above in the broadest definition of the first aspect of the invention or as defined in one of the other embodiments of the first aspect of the invention. In a preferred aspect, (A) is a heteroaryl chosen from pyridyl, pyrimidinyl, and thiophenyl.

In one embodiment of the first aspect, the invention provides a compound of Formula 1 or a pharmaceutically acceptable salt or solvate thereof, wherein (A) is a heteroaryl chosen from pyridyl, pyrimidinyl, and thiophenyl and the other variables are as defined above in the broadest definition of the first aspect of the invention chosen from pyridyl, pyrimidinyl, and thiophenyl. In a preferred aspect of this embodiment, X is 0 or 1. In another preferred aspect X is 0 or 1 and (A') is an aryl or arylalkoxy group wherein said (A') group if present has from 0, 1, 2, or 3 substituents independently chosen from halo, haloalkyl, alkyl, alkoxy, amido, —$CH_2C$(=O)$NH_2$, heteroaryl, cyano, sulfonyl, and sulfinyl.

In one embodiment of the first aspect, the invention provides a compound of Formula 1 or a pharmaceutically acceptable salt or solvate thereof, wherein (L) is a linker chosen from a single bond, —$CH_2$—, —$CH_2CH_2$— and —$CH_2CH_2CH_2$—. In a preferred embodiment, said compound of Formula 1 has X=1 and (A') is chosen from aryl and arylalkoxy wherein said aryl or arylalkoxy group has 0 or 1 substituent chosen from halo and haloalkyl.

In one embodiment of the first aspect, the invention provides a compound of Formula 1 or a pharmaceutically acceptable salt or solvate thereof, wherein (L) is a single bond or —$CH_2$—. In a preferred embodiment, said compound of Formula 1 has X=1 and (A') is chosen from aryl and arylalkoxy wherein said aryl or arylalkoxy group has 0 or 1 substituent chosen from halo and haloalkyl.

In one embodiment of the first aspect, the invention provides a compound of Formula 1 or a pharmaceutically acceptable salt or solvate thereof, wherein (L) is —$CH_2CH_2$—. In a preferred embodiment, said compound of Formula 1 has X=1 and (A') is chosen from aryl and arylalkoxy wherein said aryl or arylalkoxy group has 0 or 1 substituent chosen from halo and haloalkyl.

In one embodiment of the first aspect, the invention provides a compound of Formula 1 or a pharmaceutically acceptable salt or solvate thereof, wherein (L) is a single bond. In a preferred embodiment, said compound of Formula 1 has X=1 and (A') is chosen from aryl and arylalkoxy wherein said aryl or arylalkoxy group has 0 or 1 substituent chosen from halo and haloalkyl.

In one embodiment of the first aspect, the invention provides a compound of Formula 1 or a pharmaceutically acceptable salt or solvate thereof, wherein (D) is an aliphatic carbocyclic group or benzocycloalkyl. In a preferred embodiment, said compound of Formula 1 has X=1 and (A')

is chosen from aryl and arylalkoxy wherein said aryl or arylalkoxy group has 0 or 1 substituent chosen from halo and haloalkyl.

In one embodiment of the first aspect, the invention provides a compound of Formula 1 or a pharmaceutically acceptable salt thereof, wherein (D) is an aliphatic carbocyclic group or benzocycloalkyl, wherein said aliphatic carbocyclic group or said benzocycloalkyl has 1, 2, or 3 substituents independently chosen from —$NH_2$, —$NH(C_1$-$C_6$ alkyl), —$N(C_1$-$C_6$ alkyl)($C_1$-$C_6$ alkyl), alkyl, halo, amido, cyano, alkoxy, haloalkyl, and haloalkoxy. In a preferred embodiment, said compound of Formula 1 has X=1 and (A') is chosen from aryl and arylalkoxy, wherein said aryl or arylalkoxy group has 0 or 1 substituent chosen from halo and haloalkyl.

In one embodiment of this first aspect, the invention provides a compound of Formula 1 or a pharmaceutically acceptable salt or solvate thereof, wherein (D) is a cycloalkyl group substituted with an amido group. Preferably the cycloalkyl group is cyclopropyl, cyclobutyl, cyclopentyl, or cyclohexyl. Even more preferably, the cycloalkyl is a cyclopropyl group. In one preferred embodiment the amido group is attached to the carbon of the cycloalkyl group that is bonded to (L). In a preferred aspect of this embodiment, (A) is an aryl covalently bonded to (B) and to (A'); each (A') is covalently bonded to (A) and is independently chosen from aryl, arylalkoxy, arylalkyl, heterocyclyl, and aryloxy, wherein each (A') is substituted with 0, 1, 2, or 3 substituents independently chosen from halo, haloalkyl, haloalkoxy, amido, and —$CH_2C(=O)NH_2$.
X is 1 or 2;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to (L), and to a hydrogen atom;
(L) is a linker which links (Z) and (D), wherein said linker is chosen from a single bond, —$CH_2$—, —$CH_2CH_2$—, —$CH_2CH_2CH_2$—, and —$CH_2CH_2CH_2CH_2$—. In a preferred aspect of this embodiment, the amido group covalently bonded to the cycloalkyl group (D) is bonded through the same carbon atom of the cycloalkyl group as the (L) group.

In one embodiment of the first aspect, the invention provides a compound of Formula 1 or a pharmaceutically acceptable salt or solvate thereof, wherein (B) is a cyclopropyl ring which is covalently bonded to (A) and to (Z), wherein (A) and (Z) are covalently bonded to different carbon atoms of (B), and wherein (A) and (Z) are in the trans orientation with respect to the cyclopropyl ring (B).

In one embodiment of the first aspect, the invention provides a compound of Formula 1 or a pharmaceutically acceptable salt or solvate thereof, wherein (B) is a cyclopropyl ring which is covalently bonded to (A) and to (Z), wherein (A) and (Z) are covalently bonded to different carbon atoms of (B), wherein (A) and (Z) are in the trans orientation with respect to the cyclopropyl ring (B), and 1 (A') group is present (X=1) and said (A') group is in the meta or para position with respect to the cyclopropyl ring, wherein (A) is a phenyl group. Preferably, the one (A') group is in the para position with respect to the cyclopropyl ring, wherein said (A') group is chosen from aryl and arylalkoxy, wherein said aryl or arylalkoxy group can have 0, 1, or 2 substituents independently chosen from halo, haloalkyl, haloalkoxy, aryl, arylalkoxy, alkyl, alkoxy, amido, —$CH_2C(=O)NH_2$, heteroaryl, cyano, sulfonyl, and sulfinyl. Preferably, the 0, 1, or 2 substituents on (A') are independently chosen from halo and haloalkyl.

Compounds of Formula 1, when (D) is an aliphatic carbocyclic group or benzocycloalkyl (denoted as "(carbocyclic)" below) have a general structure of:

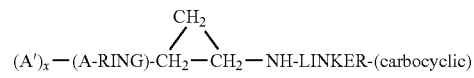

In one embodiment of this first aspect, the invention provides a compound of Formula 1 or an enantiomer, a diastereomer, or a mixture thereof, or a pharmaceutically acceptable salt or solvate thereof:

$(A')_X$-(A)-(B)—(Z)-(L)-(D)     1 wherein:
(A) is a heteroaryl or aryl group covalently bonded to (B) and to (A') if present;
each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, and cyano, wherein (A') is substituted with 0, 1, 2 or 3 substituents (e.g., 0, 1, or 2 substituents) independently chosen from halo, haloalkyl, haloalkoxy, aryl, arylalkoxy, alkyl, alkoxy, amido, —$CH_2C(=O)NH_2$, heteroaryl, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B); (Z) is —NH—; accordingly, (Z) is a nitrogen atom covalently bonded to (B), to (L), and to a hydrogen atom;
(L) is a linker which links (Z) and (D), wherein said linker is chosen from a single bond, —$CH_2$—, —$CH_2CH_2$—, —$CH_2CH_2CH_2$—, and —$CH_2CH_2CH_2CH_2$—;
(D) is a cycloalkyl covalently bonded to (L) or to (Z) when (L) is a single bond, and (D) has 0, 1, 2, or 3 substituents independently chosen from —$NH_2$, —$NH(C_1$-$C_6$ alkyl), —$N(C_1$-$C_6$ alkyl)($C_1$-$C_6$ alkyl), alkyl, halo, amido, cyano, alkoxy, haloalkyl, and haloalkoxy;
with the proviso that the following compounds are excluded:
N-(2-phenylcyclopropyl)-cyclopentanamine; and trans-N-(2-phenylcyclopropyl)-cyclohexanamine.

In another embodiment of this first aspect, the invention provides a compound of Formula 1 or an enantiomer, a diastereomer, or a mixture thereof, or a pharmaceutically acceptable salt or solvate thereof:

$(A')_X$-(A)-(B)—(Z)-(L)-(D)     1 wherein:
(A) is a heteroaryl or aryl group covalently bonded to (B) and to (A') if present;
each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, and cyano, wherein (A') is substituted with 0, 1, 2 or 3 substituents (e.g., 0, 1, or 2 substituents) independently chosen from halo, haloalkyl, haloalkoxy, aryl, arylalkoxy, alkyl, alkoxy, amido, —$CH_2C(=O)NH_2$, heteroaryl, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B); (Z) is a nitrogen atom covalently bonded to (B), to (D), and to a hydrogen atom;

(L) is a linker which links (Z) and (D), wherein said linker is a single bond;
(D) is benzocycloalkyl covalently bonded to (Z), and (D) has 0, 1, 2, or 3 substituents independently chosen from —NH₂, —NH(C₁-C₆ alkyl), —N(C₁-C₆ alkyl)(C₁-C₆ alkyl), alkyl, halo, amido, cyano, alkoxy, haloalkyl, and haloalkoxy;
with the proviso that the following compound is excluded:
10,11-dihydro-N-(2-phenylcyclopropyl)-5H-dibenzo[a,d]cyclohepten-5-amine.

In a related aspect, the invention provides a pharmaceutical composition comprising a pharmaceutically acceptable carrier and a compound of Formula 1 or a pharmaceutically acceptable salt or solvate thereof as defined above in the first aspect and related embodiments. Preferred embodiments of the compound of Formula 1 for use in the composition of this second aspect are defined herein below in this second aspect of the invention.

In one embodiment of the first aspect, the invention provides a compound of Formula 1 or a pharmaceutically acceptable salt or solvate thereof, wherein (A) is an aryl group. In a preferred embodiment, said compound of Formula 1 has X=1 and (A') is chosen from aryl and arylalkoxy wherein said aryl or arylalkoxy group has 0 or 1 substituent chosen from halo and haloalkyl.

In one embodiment of the first aspect, the invention provides a compound of Formula 1 or a pharmaceutically acceptable salt or solvate thereof, wherein (A) is a phenyl group. In a preferred embodiment, said compound of Formula 1 has X=1 and (A') is chosen from aryl and arylalkoxy wherein said aryl or arylalkoxy group has 0 or 1 substituent chosen from halo and haloalkyl.

In one embodiment of the first aspect, the invention provides a compound of Formula 1 or a pharmaceutically acceptable salt or solvate thereof, wherein X is 1 or 2.

In one embodiment of the first aspect, the invention provides a compound of Formula 1 or a pharmaceutically acceptable salt or solvate thereof, wherein X is 1; and (A') is chosen from aryl and arylalkoxy wherein said aryl or arylalkoxy group has 0 or 1 substituent chosen from halo and haloalkyl.

In one embodiment of the first aspect, the invention provides a compound of Formula 1 or a pharmaceutically acceptable salt or solvate thereof, wherein (A) is a heteroaryl.

In one embodiment of the first aspect embodiment, the invention provides a compound of Formula 1 or a pharmaceutically acceptable salt or solvate thereof, wherein (A) is a heteroaryl chosen from pyridyl, pyrimidinyl, and thiophenyl.

In one embodiment of the first aspect, the invention provides a compound of Formula 1 or a pharmaceutically acceptable salt or solvate thereof, wherein (L) is a linker chosen from —CH₂CH₂— and —CH₂CH₂CH₂—. In a preferred embodiment, said compound of Formula 1 has X=1 and (A') is chosen from aryl and arylalkoxy wherein said aryl or arylalkoxy group has 0 or 1 substituent chosen from halo and haloalkyl.

In one embodiment of the first aspect, the invention provides a compound of Formula 1 or a pharmaceutically acceptable salt or solvate thereof, wherein (L) is —CH₂CH₂—. In a preferred embodiment, said compound of Formula 1 has X=1 and (A') is chosen from aryl and arylalkoxy wherein said aryl or arylalkoxy group has 0 or 1 substituent chosen from halo and haloalkyl.

In one embodiment of the first aspect, the invention provides a compound of Formula 1 or a pharmaceutically acceptable salt or solvate thereof, wherein (B) is a cyclopropyl ring which is covalently bonded to (A) and to (Z), wherein (A) and (Z) are covalently bonded to different carbon atoms of (B), and wherein (A) and (Z) are in the trans orientation with respect to the cyclopropyl ring (B).

In one embodiment of the first aspect, the invention provides a compound of Formula 1 or a pharmaceutically acceptable salt or solvate thereof, wherein (B) is a cyclopropyl ring which is covalently bonded to (A) and to (Z), wherein (A) and (Z) are covalently bonded to different carbon atoms of (B), and wherein (A) and (Z) are in the trans orientation with respect to the cyclopropyl ring (B), and wherein 1 (A') group is present (X=1) and said (A') group is in the meta or para position with respect to the cyclopropyl ring, wherein (A) is a phenyl group. Preferably, the one (A') group is in the para position with respect to the cyclopropyl ring, wherein said (A') group is chosen from aryl (e.g., phenyl) and arylalkoxy (e.g., benzyloxy) wherein said aryl or arylalkoxy group can have 0, 1, or 2 substituents chosen from halo, haloalkyl, haloalkoxy, aryl, arylalkoxy, alkyl, alkoxy, amido, —CH₂C(=O)NH₂, heteroaryl, cyano, sulfonyl, and sulfinyl. Preferably, the 0, 1, or 2 substituents on (A') are chosen from halo and haloalkyl.

In one embodiment of the first aspect, the invention provides a compound of Formula 1 chosen from:
N-((trans)-2-(4-(benzyloxy)phenyl)cyclopropyl)-6-methoxy-2,3-dihydro-1H-inden-1-amine;
N-((trans)-2-(4-(benzyloxy)phenyl)cyclopropyl)-5,6-dimethoxy-2,3-dihydro-1H-inden-1-amine;
N-((trans)-2-(4-(benzyloxy)phenyl)cyclopropyl)-4,5-dimethoxy-2,3-dihydro-1H-inden-1-amine;
N-((trans)-2-phenylcyclopropyl)-2,3-dihydro-1H-inden-1-amine;
6-methoxy-N-((trans)-2-phenylcyclopropyl)-2,3-dihydro-1H-inden-1-amine;
6-chloro-N-((trans)-2-phenylcyclopropyl)-2,3-dihydro-1H-inden-1-amine;
N-((trans)-2-phenylcyclopropyl)-6-(trifluoromethyl)-2,3-dihydro-1H-inden-1-amine;
7-methoxy-N-((trans)-2-phenylcyclopropyl)-1,2,3,4-tetrahydronaphthalen-1-amine;
N-((trans)-2-(3'-chlorobiphenyl-4-yl)cyclopropyl)-6-methoxy-2,3-dihydro-1H-inden-1-amine;
N-((trans)-2-(4'-chlorobiphenyl-4-yl)cyclopropyl)-6-methoxy-2,3-dihydro-1H-inden-1-amine;
6-methoxy-N-((trans)-2-(3'-methoxybiphenyl-4-yl)cyclopropyl)-2,3-dihydro-1H-inden-1-amine;
N-trans-(2-cyclohexylethyl)-2-phenylcyclopropanamine;
(Trans)-N-(3-cyclohexylpropyl)-2-phenylcyclopropanamine; (Trans)-N-(2-cycloheptylethyl)-2-phenylcyclopropanamine;
(Trans)-2-(4-(3-bromobenzyloxyl)phenyl)-N-(2-cyclohexylethyl)cyclopropanamine;
N-((trans)-2-(4-(3-bromobenzyloxyl)phenyl)cyclopropyl)-6-methoxy-2,3-dihydro-1H-inden-1-amine;
(Trans)-2-(3'-chlorobiphenyl-4-yl)-N-(2-cyclohexylethyl)cyclopropanamine;
(Trans)-2-(4'-chlorobiphenyl-4-yl)-N-(2-cyclohexylethyl)cyclopropanamine;
(Trans)-N-(2-cyclohexylethyl)-2-(3'-methoxybiphenyl-4-yl)cyclopropanamine;
N-((trans)-2-(4-(benzyloxy)phenyl)cyclopropyl)-7-methoxy-1,2,3,4-tetrahydronaphthalen-1-amine; and
1-((trans)-2-(4-(benzyloxy)phenyl)cyclopropylamino)cyclopropanecarboxamide; or a pharmaceutically acceptable salt or solvate thereof.

In one specific embodiment of the first aspect, the invention provides a compound of Formula 1 or an enantiomer, a diastereomer, or a mixture thereof, or a pharmaceutically acceptable salt or solvate thereof:

$$(A')_{X}\text{-}(A)\text{-}(B)\text{—}(Z)\text{-}(L)\text{-}(D) \quad 1$$

wherein:
(A) is a heteroaryl or aryl group covalently bonded to (B) and to (A') if present;
each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, cyano, wherein (A') is substituted with 0, 1, 2, or 3 substituents independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl;
K is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to (L), and to a hydrogen atom;
(L) is a linker which links (Z) and (D), wherein said linker is chosen from —CH$_2$CH$_2$—, —CH$_2$CH$_2$CH$_2$—, and —CH$_2$CH$_2$CH$_2$CH$_2$—;
(D) is a cycloalkyl group covalently bonded to (L), and (D) has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy. In a related aspect, the invention provides a pharmaceutical composition comprising a compound of Formula 1 as defined above and a pharmaceutically acceptable carrier.

In one specific embodiment of the first aspect, the invention provides a compound of Formula 1 or an enantiomer, a diastereomer, or a mixture thereof, or a pharmaceutically acceptable salt or solvate thereof:

$$(A')_{X}\text{-}(A)\text{-}(B)\text{—}(Z)\text{-}(L)\text{-}(D) \quad 1$$

wherein:
(A) is a heteroaryl or aryl group covalently bonded to (B) and to (A') if present;
(A'), if present, is chosen from aryl, arylalkoxy, arylalkyl, heterocyclyl, aryloxy, halo, alkoxy, haloalkyl, cycloalkyl, haloalkoxy, cyano, wherein (A') is substituted with 0, 1, 2, or 3 substituents chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to (L), and to a hydrogen atom;
(L) is a linker which links (Z) and (D), wherein said linker is chosen from —CH$_2$CH$_2$—, —CH$_2$CH$_2$CH$_2$—, and —CH$_2$CH$_2$CH$_2$CH$_2$—;
(D) is covalently bonded to (L), wherein (D) is a cycloalkyl group chosen from cyclopentyl, cyclohexyl, and cycloheptyl and (D) has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy. Preferably, the substituents on (D) are independently chosen from —NH$_2$, —NH(C$_1$-C$_6$ alkyl), and —N(C$_1$-C$_6$ alkyl)(C$_1$-C$_6$ alkyl). In a related aspect, the invention provides a pharmaceutical composition comprising a compound of Formula 1 or a pharmaceutically acceptable salt or solvate thereof as defined above and a pharmaceutically acceptable carrier.

In yet another specific embodiment of the first aspect, the invention provides a compound of Formula 1 or an enantiomer, a diastereomer, or a mixture thereof, or a pharmaceutically acceptable salt or solvate thereof:

$$(A')_{X}\text{-}(A)\text{-}(B)\text{—}(Z)\text{-}(L)\text{-}(D) \quad 1$$

wherein:
(A) is a heteroaryl or aryl group covalently bonded to (B) and to (A');
(A') is chosen from an aryl or arylalkoxy group, wherein (A') is substituted with 0, 1, or 2 substituents independently chosen from halo and haloalkyl;
X is 1;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to (L) or to (D) when (L) is a single bond, and to a hydrogen atom;
(L) is a linker which links (Z) and (D), wherein said linker is chosen from a single bond, —CH$_2$—, —CH$_2$CH$_2$—, —CH$_2$CH$_2$CH$_2$—, and —CH$_2$CH$_2$CH$_2$CH$_2$—; (D) is an aliphatic carbocyclic group or benzocycloalkyl, wherein said aliphatic carbocyclic group or said benzocycloalkyl is covalently bonded to (L) or to (Z) when (L) is a single bond, and wherein (D) has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy. In a related aspect, the invention provides a pharmaceutical composition comprising a compound of Formula 1 as defined above and a pharmaceutically acceptable carrier.

In another specific embodiment of the first aspect, the invention provides a compound of Formula 1 or an enantiomer, a diastereomer, or a mixture thereof, or a pharmaceutically salt or solvate thereof:

$$(A')_{X}\text{-}(A)\text{-}(B)\text{—}(Z)\text{-}(L)\text{-}(D) \quad 1$$

wherein:
(A) is a phenyl group covalently bonded to (B) and to (A');
(A') is chosen from aryl and arylalkoxy, wherein said aryl or arylalkoxy is substituted with 0, 1, 2, or 3 substituents chosen from halo and haloalkyl;
X is 1;
(B) is a cyclopropyl ring which is covalently bonded to (A) and to (Z), wherein (A) and (Z) are covalently bonded to different carbon atoms of (B), wherein the groups (A) and (Z) are in trans orientation in respect of the cyclopropyl ring (B);
(Z) is —NH—; accordingly, (Z) is a nitrogen atom covalently bonded to (B), to (D) and to a hydrogen atom;
(L) is a linker which is a single covalent bond linking (Z) and (D);
(D) is benzocycloalkyl covalently bonded to (Z), and (D) has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy. In a related aspect, the invention provides a pharmaceutical composition comprising a compound of Formula 1 or a pharmaceutically acceptable salt or solvate thereof as defined above and a pharmaceutically acceptable carrier.

In one embodiment of the first aspect, the invention provides a compound of Formula 1 or an enantiomer, a diastereomer, or a mixture thereof, or a pharmaceutically acceptable salt or solvate thereof:

$$(A')_{X}\text{-}(A)\text{-}(B)\text{—}(Z)\text{-}(L)\text{-}(D) \quad 1$$

wherein:
(A) is a heteroaryl covalently bonded to (B) and to (A') if present; each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to (L) or to (D) when (L) is a single bond, and to a hydrogen atom;
(L) is a linker which links (Z) and (D), wherein said linker is chosen from a single bond, —CH$_2$—, —CH$_2$CH$_2$—, —CH$_2$CH$_2$CH$_2$—, and —CH$_2$CH$_2$CH$_2$CH$_2$—;
(D) is an aliphatic carbocyclic group or benzocycloalkyl, wherein said aliphatic carbocyclic group or said benzocycloalkyl is covalently bonded to (L) or to (Z) when (L) is a single bond, and wherein (D) has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy. In a related aspect, the invention provides a pharmaceutical composition comprising a compound of Formula 1 or a pharmaceutically acceptable salt or solvate thereof as defined above and a pharmaceutically acceptable carrier.

In a second aspect, the invention provides a method of treating and/or preventing a disease or condition, the method comprising administering, to a patient (preferably a human) in need of treatment or prevention, a therapeutically effective amount of a composition comprising a compound of Formula 1 as defined above or an enantiomer, a diastereomer, or a mixture thereof, or a pharmaceutically acceptable salt or solvate thereof and a pharmaceutically acceptable carrier. This aspect also relates to a compound of Formula 1 as defined above or an enantiomer, a diastereomer, or a mixture thereof, or a pharmaceutically acceptable salt or solvate thereof for use as a medicament.

In a third aspect, the invention provides a method of inhibiting LSD1 activity comprising administering, to a patient (preferably a human) in need of treatment, a therapeutically effective amount of a composition comprising a compound of Formula 1 or an enantiomer, a diastereomer, or a mixture thereof, or a pharmaceutically acceptable salt or solvate thereof:

$$(A')_X\text{-}(A)\text{-}(B)\text{—}(Z)\text{-}(L)\text{-}(D) \qquad 1$$

wherein:
(A) is a heteroaryl or aryl covalently bonded to (B) and to (A') if present; each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to (L) or to (D) when (L) is a single bond, and to a hydrogen atom;
(L) is a linker covalently linking (Z) and (D), wherein said linker is chosen from a single bond, —CH$_2$—, —CH$_2$CH$_2$—, —CH$_2$CH$_2$CH$_2$—, and —CH$_2$CH$_2$CH$_2$CH$_2$—;
(D) is an aliphatic carbocyclic group or benzocycloalkyl, wherein said aliphatic carbocyclic group or said benzocycloalkyl is covalently bonded to (L) or to (Z) when (L) is a single bond, and wherein (D) has 0, 1, 2, or 3 substituents chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy;
and a pharmaceutically acceptable carrier in an amount sufficient to inhibit LSD1 activity. This aspect can be reformulated as a compound of Formula 1 as herein defined for use as a LSD1 inhibitor. This aspect can also be reformulated as a compound of Formula 1 for use in the treatment of a disease associated to LSD1. In a related aspect, a method for treating an individual (preferably a human) is provided, said method comprising identifying an individual in need of treatment and administering to said individual a therapeutically effective amount of a compound of Formula 1. In a preferred aspect, the therapeutically effective amount of a compound of Formula 1 is an amount sufficient to inhibit LSD1. Preferred embodiments of the compounds of Formula 1 for use in the composition and method of this fourth aspect of the invention are as defined herein above in the first aspect of the invention.

In a fourth aspect, the invention provides a method of treating or preventing cancer, the method comprising administering, to a patient (preferably a human) in need of treatment or prevention, a therapeutically effective amount of a composition comprising a compound of Formula 1 as defined above in the first or second aspect of the invention or an enantiomer, a diastereomer, or a mixture thereof, or a pharmaceutically acceptable salt or solvate thereof, and a pharmaceutically acceptable carrier. This aspect can be reformulated as a compound of Formula 1 as defined above in the first or second aspect of the invention or an enantiomer, a diastereomer, or a mixture thereof, or a pharmaceutically acceptable salt or solvate thereof for use in treating and/or preventing cancer. Preferably, the cancer is chosen from breast cancer, colorectal cancer, lung cancer, prostate cancer, testicular cancer, and brain cancer, skin cancer, and blood cancer. In a preferred aspect, the therapeutically effective amount of a compound of Formula 1 is an amount sufficient to inhibit LSD1.

In one embodiment of the fourth aspect, the invention provides a compound of Formula 1 or an enantiomer, a diastereomer, or a mixture thereof, or a pharmaceutically acceptable salt or solvate thereof for use in treating or preventing cancer:

$$(A')_X\text{-}(A)\text{-}(B)\text{—}(Z)\text{-}(L)\text{-}(D) \qquad 1$$

wherein:
(A) is a phenyl group covalently bonded to (B) and to (A');
(A') is chosen from aryl and arylalkoxy, wherein said aryl or arylalkoxy has 0, 1, 2, or 3 substituents independently chosen from halo and haloalkyl;
X is 1;
(B) is a cyclopropyl ring which is covalently bonded to (A) and to (Z), wherein (A) and (Z) are covalently bonded to different carbon atoms of (B) and wherein the groups (A) and (Z) are in trans orientation in respect of the cyclopropyl ring (B);

(Z) is —NH—; accordingly, (Z) is a nitrogen atom covalently bonded to (B), to (L) and to a hydrogen atom;
(L) is a linker which links (Z) and (D), wherein said linker is chosen from —CH$_2$CH$_2$— and —CH$_2$CH$_2$CH$_2$—;
(D) is a cycloalkyl group covalently bonded to (L), and (D) has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy. In a related aspect, the invention provides a pharmaceutical composition for use in treating or preventing cancer comprising a compound of Formula 1 or a pharmaceutically acceptable salt or solvate thereof as defined above and a pharmaceutically acceptable carrier. In an even more specific aspect, the cancer is chosen from prostate, testicular, brain, colorectal, lung, breast, skin, and blood. In one specific aspect, the cancer is prostate cancer. In one specific aspect, the cancer is lung cancer. In one specific aspect, the cancer is brain cancer. In one specific aspect, the cancer is blood cancer (e.g., leukemia). In one specific aspect, the cancer is breast cancer. In one specific aspect, the cancer is colorectal cancer.

In a fifth aspect, the invention provides a method for identifying a compound which is a selective inhibitor of LSD1, the method comprising selecting or providing a compound which is a substituted heteroarylcyclopropylamine or a substituted arylcyclopropylamine, and determining the ability of the compound to inhibit LSD1 and MAO-A and/or MAO-B, wherein a compound that inhibits LSD1 to a greater extent than MAO-A and/or MAO-B is identified as a LSD1 selective inhibitor.

According to this fifth aspect of the invention, a substituted heteroarylcyclopropylamine or a substituted arylcyclopropylamine is defined as follows in Formula 2:

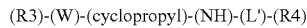

(R3)-(W)-(cyclopropyl)-(NH)-(L')-(R4)

wherein:
(R3) is present or not present, when present (R3) is chosen from arylalkyl, arylalkoxy, arylalkyl, heterocyclylalkyl, and heterocycylalkoxy, wherein said (R3) group has 0, 1, 2, or 3 substituents independently chosen from halo, alkyl, alkoxy, carbocyclyl, cycloalkyl, cycloalkoxy, haloalkyl, haloalkoxy, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heterocyclyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amino, and said (R3) group is covalently bonded to (W);
(W) is an aryl or heteroaryl group covalently bonded to (R3) and to (cyclopropyl), wherein said (W) has 0, 1, or 2 substituents, not including (R3) and (cyclopropyl), which substituents are independently chosen from halo, alkyl, alkoxy, carbocyclyl, cycloalkyl, cycloalkoxy, haloalkyl, haloalkoxy, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heterocyclyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, carbamyl, N-carbamyl, O-thiocarbamyl, N-thiocarbamyl, and C-amido;
(cyclopropyl) is a cyclopropyl group covalently bonded to (W) and to the nitrogen of (NH);
(NH) is a —NH— group (i.e., nitrogen covalently bonded to a hydrogen atom), wherein the nitrogen is covalently bonded to (cyclopropyl) and to (L') or to (R4) when (L') is a single bond;
(L') is a linker of formula —(CH$_2$)$_n$— where n is 0, 1, 2, 3, 4, 5, or 6, and further wherein (L') is covalently bonded to the nitrogen of (NH) and to (R4); and
(R4) is an aliphatic carbocyclic group or benzocycloalkyl, wherein said aliphatic carbocyclic group or said benzocycloalkyl is covalently bonded to (L') or to (Z) when (L') is a single bond, wherein said (R4) group has 0, 1, 2, or 3 substituents independently chosen from halo, alkyl, alkoxy, carbocyclyl, cycloalkyl, cycloalkoxy, haloalkyl, haloalkoxy, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heterocyclyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, 0-thiocarbamyl, N-thiocarbamyl, and C-amido.

According to the fifth aspect of the invention, a compound of Formula 2 is provided which is a selective LSD1 inhibitor. The selective LSD1 inhibitor as identified by the method of this embodiment is used to prepare a pharmaceutical composition comprising a therapeutically effective amount of said selective LSD1 inhibitor of Formula 2, or a pharmaceutically acceptable salt or solvate thereof, and a pharmaceutically acceptable carrier. The pharmaceutical composition can be administered to an individual in need of such treatment. According to this embodiment, the therapeutically effective amount is an amount sufficient to inhibit LSD1 selectively.

Thus, the invention provides a pharmaceutical composition comprising a pharmaceutically acceptable carrier and a compound of Formula 1 or 2 which is a selective inhibitor of LSD1. LSD1 selective inhibitors have Ki values for LSD1 which are at least 2-fold lower than the Ki value for MAO-A and/or MAO-B. In one aspect of this embodiment, the LSD1 Ki value is at least 5-fold lower than the Ki value for MAO-A and/or MAO-B. In one aspect of this embodiment, the LSD1 Ki value is at least 10-fold lower than the Ki value for MAO-A and/or MAO-B. In one embodiment of the invention, the pharmaceutical composition comprising a LSD1 selective inhibitor of Formula 1 or 2, or a pharmaceutically acceptable salt or solvate thereof is useful for treating and/or preventing a disease in an individual. In one aspect, a therapeutically effective amount of the composition is administered to an individual in an amount sufficient to prevent or treat a disease. In a more specific aspect, the disease is cancer. In an even more specific aspect, the disease is a cancer chosen from prostate, testicular, brain, colorectal, lung, breast, skin, and blood cancer. In one specific aspect, the cancer is prostate cancer. In one specific aspect, the cancer is lung cancer. In one specific aspect, the cancer is brain cancer. In one specific aspect, the cancer is blood cancer (e.g., leukemia). In one specific aspect, the cancer is breast cancer. In one specific aspect, the cancer is colorectal cancer.

According to the fifth aspect of the invention, a compound of Formula 2 is provided which is a dual inhibitor of LSD1 and MAO-B. The dual LSD1 MAO-B inhibitor as identified by the method of this embodiment can be used to prepare a pharmaceutical composition comprising a therapeutically effective amount of said dual LSD1 MAO-B inhibitor of Formula 2, or a pharmaceutically acceptable salt or solvate thereof, and a pharmaceutically acceptable carrier. The pharmaceutical composition can be administered to an individual in need of such treatment. According to this embodiment, the therapeutically effective amount is an amount sufficient to inhibit MAO-B and LSD1.

Thus, the invention provides a pharmaceutical composition comprising a pharmaceutically acceptable carrier and a compound of Formula 1 or 2 that is a dual inhibitor of LSD1 and MAO-B. Preferably, LSD1 MAO-B dual inhibitors have Ki values for LSD1 and MAO-B that are at least 2-fold lower than the Ki value for MAO-A. In one aspect of this embodiment, the LSD1 and MAO-B Ki values are at least 5-fold lower than the Ki value for MAO-A. In one aspect of this embodiment, the LSD1 and MAO-B Ki values are least 10-fold lower than the Ki value for MAO-A.

Recent studies have implicated LSD1 in viral infection and reactivation. In particular it was shown that pharmacological inhibitors of LSD1 like parnate and siRNA knock down of LSD1 caused reduced viral infectivity and reduced reactivation after latency (Liang et al. (2009) *Nat. Med.* 15:1312-1317). Therefore it is believed that the compounds of the invention can be used for treating or preventing viral infection. Furthermore, it is believed that the compounds of the invention can treat or prevent viral reactivation after latency.

Thus, in one embodiment, the invention provides a method for treating or preventing a viral infection, the method comprising administering to an individual (preferably a human) a compound of Formula 1 as defined above in any of the aspects and embodiments of the invention or a pharmaceutically acceptable salt or solvate thereof. Accordingly, the invention also provides a compound of Formula 1 as defined above in any of the aspects and embodiments of the invention or a pharmaceutically acceptable salt or solvate thereof for use in treating or preventing a viral infection. In a preferred embodiment, the viral infection is a herpesvirus infection. In an even more preferred embodiment, the herpesvirus infection is caused by and/or associated with a herpesvirus chosen from HSV-1, HSV-2, and Epstein-Barr virus. In one aspect of this embodiment, the viral infection is caused by and/or associated with HIV.

In one embodiment, the invention provides a method for treating or preventing viral reactivation after latency, the method comprising administering to an individual (preferably a human) a compound of Formula 1 as defined above in any of the aspects and embodiments of the invention or a pharmaceutically acceptable salt or solvate thereof. Accordingly, the invention also provides a compound of Formula 1 as defined above in any of the aspects and embodiments of the invention or a pharmaceutically acceptable salt or solvate thereof for use in treating or preventing viral reactivation after latency. In a preferred embodiment, the virus that is reactivating is a herpesvirus. In an even more preferred embodiment, the herpesvirus that is reactivating is chosen from HSV-1, HSV-2, and Epstein-Barr virus. In one aspect of this embodiment, the virus that is reactivating is HIV.

The compounds of the invention of Formula 1 or 2 do not include any of:
N-(2-phenylcyclopropyl)-cyclopentanamine (corresponding to CAS Reg. No. 802594-05-4);
10,11-dihydro-N-(2-phenylcyclopropyl)-5H-dibenzo[a,d] cyclohepten-5-amine (corresponding to CAS Reg No. 749796-68-7); and
trans-N-(2-phenylcyclopropyl)-cyclohexanamine (corresponding to CAS Reg. no. 32751-99-8).

In a further specific embodiment, the present invention provides a compound of Formula 1:

$$(A')_X-(A)-(B)-(Z)-(L)-(D) \quad 1$$

or an enantiomer, a diastereomer, or a mixture thereof, or a pharmaceutically acceptable salt or solvate thereof.

Also provided is a pharmaceutical composition comprising any of the aforementioned entities and a pharmaceutically acceptable carrier. The invention further relates to the compound of Formula 1 or a pharmaceutically acceptable salt or solvate thereof for use in treating or preventing cancer. Moreover, the invention relates to a method of treating or preventing cancer, the method comprising administering, to a patient (preferably a human) in need of such treatment or prevention, a therapeutically effective amount of the compound of Formula 1 or a pharmaceutically acceptable salt or solvate thereof, or a pharmaceutical composition comprising any of the aforementioned entities and a pharmaceutically acceptable carrier. The cancer may be, for example, prostate cancer, testicular cancer, brain cancer, colorectal cancer, lung cancer, breast cancer, skin cancer, or blood cancer.

For this specific embodiment, the definitions and preferred definitions of the groups comprised in Formula 1 will be explained in the following.

(A) is heteroaryl or aryl.

It is to be understood that the terms "heteroaryl" and "aryl" do not necessarily refer to monovalent groups. Accordingly, if X is different from 0, then moiety (A) is covalently bonded to moiety (B) and to X moieties (A'), as indicated in Formula 1.

In a preferred aspect of this specific embodiment, (A) is aryl (such as, e.g., phenyl, naphthyl, or anthracenyl) or, more preferably, (A) is phenyl or naphthyl or, even more preferably, (A) is phenyl.

In a further preferred aspect of this specific embodiment, (A) is heteroaryl (such as, e.g., thiophenyl (i.e., thienyl), benzo[b]thienyl, naphtho[2,3-b]thienyl, thianthrenyl, furyl, isobenzofuranyl, chromenyl, xanthenyl, phenoxathiinyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, isoxazolyl, furazanyl, phenoxazinyl, isocoumarin, pyrido[1,2-a]pyrimidin-4-one, pyrazolo[1,5-a] pyrimidinyl, 1,2-benzisoxazol-3-yl, benzimidazolyl, 2-oxindolyl, or 2 oxobenzimidazolyl) or, more preferably, (A) is chosen from pyridyl, pyrimidinyl, and thiophenyl.

Each (A'), if present, is independently chosen from aryl, arylalkoxy, arylalkyl, heterocyclyl, aryloxy, halo, alkoxy, haloalkyl, cycloalkyl, haloalkoxy, and cyano, wherein each of the aforementioned groups (A') is substituted with 0, 1, 2, or 3 substituents independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl. It is to be understood that, if (A') is substituted with 0 substituents, the respective group (A') is unsubstituted (i.e., substituted with hydrogen).

Preferably, each (A'), if present, is independently chosen from aryl, arylalkyl, aryloxy and arylalkoxy, more preferably from aryl and arylalkoxy, wherein said aryl, said arylalkyl, said aryloxy or said arylalkoxy is substituted with 0, 1, 2 or 3 (preferably, 0, 1, or 2; more preferably, 0 or 1) substituents. Said substituents are each independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl. Preferably, said substituents are each independently chosen from halo, haloalkyl, alkyl, alkoxy, cyano, sulfonyl, and sulfinyl. More preferably, said substituents are each independently chosen from halo and haloalkyl.

More preferably, each (A'), if present, is independently chosen from phenyl, benzyloxy, and phenethyloxy, wherein said phenyl, said benzyloxy or said phenethyloxy is substituted with 0, 1, 2 or 3 (preferably, 0, 1, or 2; more preferably, 0 or 1) substituents. Said substituents are each independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl. Preferably, said substituents are each independently chosen from halo, haloalkyl, alkyl, alkoxy, cyano, sulfonyl, and sulfinyl. More preferably, said substituents are each independently chosen from halo and haloalkyl.

X is 0, 1, 2, or 3. It is to be understood that, if X is 0, the group (A) is not bonded to any group (A') but instead to hydrogen.

In a preferred aspect of this specific embodiment, X is 1, 2, or 3 or, more preferably, X is 1 or 2 or, even more preferably, X is 1.

In a further preferred aspect of this specific embodiment, X is 0 or 1 or, more preferably, X is 0.

If X is 1 and (A) is phenyl, then (A') is preferably in the meta position or in the para position (more preferably, in the para position) with respect to the cyclopropyl ring (B).

(B) is a cyclopropyl ring. The moieties (A) and (Z) are covalently bonded to different carbon atoms of the cyclopropyl ring (B). Preferably, (A) and (Z) are in the trans orientation with respect to the cyclopropyl ring (B).

(Z) is —NH—, i.e. a group —N(—H)—.

(L) is chosen from a single bond, —CH$_2$—, —CH$_2$CH$_2$—, —CH$_2$CH$_2$CH$_2$—, and —CH$_2$CH$_2$CH$_2$CH$_2$—.

Preferably, (L) is chosen from a single bond, —CH$_2$—, —CH$_2$CH$_2$—, and —CH$_2$CH$_2$CH$_2$—. More preferably, (L) is a single bond or —CH$_2$—. Even more preferably, (L) is a single bond. In a further preferred embodiment, (L) is —CH$_2$CH$_2$—.

(D) is an aliphatic carbocyclic group or benzocycloalkyl; preferably, (D) is cycloalkyl (which is preferably chosen from cyclopentyl, cyclohexyl, and cycloheptyl) or benzocycloalkyl (which is preferably chosen from indyl, 1,2,3,4-tetrahydronaphthyl, and benzocycloheptyl, and more preferably chosen from indyl and 1,2,3,4-tetrahydronaphthyl). Said aliphatic carbocyclic group or said benzocycloalkyl (or, accordingly, said cycloalkyl) has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy, preferably from —NH$_2$, —NH(C$_1$-C$_6$ alkyl), and —N(C$_1$-C$_6$ alkyl)(C$_1$-C$_6$ alkyl).

It is to be understood that, if said aliphatic carbocyclic group or said benzocycloalkyl (or, accordingly, said cycloalkyl) has 0 substituents, then the respective group is unsubstituted (i.e., substituted with hydrogen).

In a preferred aspect of this specific embodiment, said aliphatic carbocyclic group or said benzocycloalkyl (or, accordingly, said cycloalkyl) is unsubstituted.

In a further preferred aspect of this specific embodiment, said aliphatic carbocyclic group or said benzocycloalkyl (or, accordingly, said cycloalkyl) has 1, 2, or 3 substituents, more preferably 1 or 2 substituents, and even more preferably 1 substituent, wherein said substituents are independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy, preferably from —NH$_2$, —NH(C$_1$-C$_6$ alkyl), and —N(C$_1$-C$_6$ alkyl)(C$_1$-C$_6$ alkyl).

The present invention also encompasses all combinations of the above alternative preferred aspects. Accordingly, in one aspect: (A) is aryl or, more preferably, (A) is phenyl or naphthyl or, even more preferably, (A) is phenyl; X is 1, 2, or 3 or, more preferably, X is 1 or 2 or, even more preferably, X is 1; and (D) is an aliphatic carbocyclic group or benzocycloalkyl, wherein said aliphatic carbocyclic group or said benzocycloalkyl is unsubstituted. In another aspect: (A) is aryl or, more preferably, (A) is phenyl or naphthyl or, even more preferably, (A) is phenyl; X is 1, 2, or 3 or, more preferably, X is 1 or 2 or, even more preferably, X is 1; and (D) is an aliphatic carbocyclic group or benzocycloalkyl, wherein said aliphatic carbocyclic group or said benzocycloalkyl has 1, 2, or 3 substituents, more preferably 1 or 2 substituents, and even more preferably 1 substituent, wherein said substituents are independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy, preferably from —NH$_2$, —NH(C$_1$-C$_6$ alkyl), and —N(C$_1$-C$_6$ alkyl)(C$_1$-C$_6$ alkyl). In another aspect: (A) is aryl or, more preferably, (A) is phenyl or naphthyl or, even more preferably, (A) is phenyl; X is 0 or 1 or, more preferably, X is 0; and (D) is an aliphatic carbocyclic group or benzocycloalkyl, wherein said aliphatic carbocyclic group or said benzocycloalkyl is unsubstituted. In another aspect: (A) is aryl or, more preferably, (A) is phenyl or naphthyl or, even more preferably, (A) is phenyl; X is 0 or 1 or, more preferably, X is 0; and (D) is an aliphatic carbocyclic group or benzocycloalkyl, wherein said aliphatic carbocyclic group or said benzocycloalkyl has 1, 2, or 3 substituents, more preferably 1 or 2 substituents, and even more preferably 1 substituent, wherein said substituents are independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy, preferably from —NH$_2$, —NH(C$_1$-C$_6$ alkyl), and —N(C$_1$-C$_6$ alkyl)(C$_1$-C$_6$ alkyl). In another aspect: (A) is heteroaryl or, more preferably, (A) is chosen from pyridyl, pyrimidinyl, and thiophenyl; X is 1, 2, or 3 or, more preferably, X is 1 or 2 or, even more preferably, X is 1; and (D) is an aliphatic carbocyclic group or benzocycloalkyl, wherein said aliphatic carbocyclic group or said benzocycloalkyl is unsubstituted. In another aspect: (A) is heteroaryl or, more preferably, (A) is chosen from pyridyl, pyrimidinyl, and thiophenyl; X is 1, 2, or 3 or, more preferably, X is 1 or 2 or, even more preferably, X is 1; and (D) is an aliphatic carbocyclic group or benzocycloalkyl, wherein said aliphatic carbocyclic group or said benzocycloalkyl has 1, 2, or 3 substituents, more preferably 1 or 2 substituents, and even more preferably 1 substituent, wherein said substituents are independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy, preferably from —NH$_2$, —NH(C$_1$-C$_6$ alkyl), and —N(C$_1$-C$_6$ alkyl)(C$_1$-C$_6$ alkyl). In another aspect: (A) is heteroaryl or, more preferably, (A) is chosen from pyridyl, pyrimidinyl, and thiophenyl; X is 0 or 1 or, more preferably, X is 0; and (D) is an aliphatic carbocyclic group or benzocycloalkyl, wherein said aliphatic carbocyclic group or said benzocycloalkyl is unsubstituted. In another aspect: (A) is heteroaryl or, more preferably, (A) is chosen from pyridyl, pyrimidinyl, and thiophenyl; X is 0 or 1 or, more preferably, X is 0; and (D) is an aliphatic carbocyclic group or benzocycloalkyl, wherein said aliphatic carbocyclic group or said benzocycloalkyl has 1, 2, or 3 substituents, more preferably 1 substituent, wherein said substituents are independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy, preferably from —NH$_2$, —NH(C$_1$-C$_6$ alkyl), and —N(C$_1$-C$_6$ alkyl)(C$_1$-C$_6$ alkyl).

The following compounds are excluded in this specific embodiment: N-(2-phenylcyclopropyl)-cyclopentanamine; 10,11-dihydro-N-(2-phenylcyclopropyl)-5H-dibenzo[a,d]cyclohepten-5-amine; and trans-N-(2-phenylcyclopropyl)-cyclohexanamine.

Definitions

As used herein, the term "alkyl" refers to a saturated aliphatic (i.e., non-aromatic) acyclic hydrocarbon (i.e., a group consisting of carbon atoms and hydrogen atoms), including straight chain and/or branched chain groups, having from 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc. up to and including 20 carbon atoms), and comprising neither carbon-to-carbon double bonds nor carbon-to-carbon triple bonds. Preferably, the "alkyl" has from 1 to 10 carbon atoms. More preferably, the "alkyl" has from 1 to 6 carbon atoms, and even more preferably 1 to 4 carbon atoms.

As used herein, the term "alkenyl" refers to an unsaturated aliphatic acyclic hydrocarbon including straight chain and/or branched chain groups, comprising at least one carbon-to-carbon double bond, and comprising no carbon-to-carbon triple bonds. In a more specific definition, the alkenyl group is further defined as having 2 to 20 carbon atoms. In another more specific definition, it is an alkenyl having 2 to 10 carbon atoms. In yet another more specific definition, it is an alkenyl having 2 to 6 carbon atoms, and in yet another more specific definition, it is an alkenyl having 2 to 4 carbon atoms.

As used herein, the term "alkynyl" refers to an unsaturated aliphatic acyclic hydrocarbon including straight chain and/or branched chain groups, comprising at least one carbon-to-carbon triple bond and optionally comprising one or more carbon-to-carbon double bonds. In a more specific definition, the alkynyl group is further defined as having 2 to 20 carbon atoms. In another more specific definition, it is an alkynyl having 2 to 10 carbon atoms. In yet another more specific definition, it is an alkynyl having 2 to 6 carbon atoms, and in yet another more specific definition, it is an alkynyl having 2 to 4 carbon atoms.

As used herein, the term "halo" refers to chloro, fluoro, bromo, and iodo.

As used herein, the term "hydro" refers to a hydrogen atom (—H group).

As used herein, the term "alkoxy" refers to an —O-alkyl group, wherein "alkyl" has the meaning provided above.

As used herein, the term "haloalkyl" refers to an alkyl group substituted with 1 to 6 halo groups. In a specific embodiment, haloalkyl is a —CX$_3$ group wherein X is a halo group. The halo groups can be independently selected. In a more specific embodiment, haloalkyl is a —CF$_3$ group.

As used herein, the term "haloalkoxy" refers to an alkoxy group substituted with 1 to 6 halo groups. In a specific embodiment, haloalkyl is a —OCX$_3$ group wherein X is a halo group. The halo groups can be independently selected. Preferably the halo is fluoro.

As used herein, the term "cycloalkoxy" refers to an —O-cycloalkyl group, wherein the cycloalkyl group is as defined herein below.

As used herein, the term "aryloxy" refers to an —O-aryl group, wherein the aryl group is as defined herein below.

As used herein, the term "heteroaryloxy" refers to an —O-heteroaryl group, wherein the heteroaryl group is as defined herein below.

As used herein, the term "mercapto" refers to a —SH group.

As used herein, the term "alkylthio" refers to a —S-alkyl group, wherein the alkyl group is as defined herein above.

As used herein, the term "cycloalkylthio" refers to a —S-cycloalkyl group, wherein the cycloalkyl group is as defined herein below.

As used herein, the term "arylthio" refers to a —S-aryl group, wherein the aryl group is as defined herein below.

As used herein, the term "heteroarylthio" refers to a —S-heteroaryl group, wherein the heteroaryl group is as defined herein below.

As used herein, the term "carbonyl" refers to a —C(=O)R" group, wherein R" is as defined herein below.

Unless specified otherwise, R" is selected from the group consisting of hydro, alkyl, cycloalkyl, aryl, heteroaryl (bonded through a ring carbon atom) and heterocyclyl (bonded through a ring carbon atom), wherein said hydro, alkyl, cycloalkyl, aryl, heteroaryl and heterocyclyl are as defined herein.

As used herein, the term "aldehyde" group refers to a carbonyl group as defined herein above, wherein R" is hydro.

As used herein, the term "amide" refers to a —C(=O)NH$_2$ group.

As used herein, the term "cycloketone" group refers to a cycloalkyl group as defined herein below, wherein one of the carbon atoms which form the ring has an "=O" bonded to it, i.e., one of the ring carbon atoms of the cycloalkyl group is a —C(=O)— group.

As used herein, the term "thiocarbonyl" refers to a —C(=S)R" group, wherein R" is as defined herein above.

As used herein, the term "O-carboxy" refers to an —OC(=O)R" group, wherein R" is as defined herein above.

As used herein, the term "C-carboxy" refers to a —C(=O)OR" group, wherein R" is as defined herein above.

As used herein, the term "ester" refers to a C-carboxy group as defined herein above or a molecule comprising such group, wherein R" is as defined herein above and R" is not hydro.

As used herein, the term "C-carboxy salt" refers to a —C(=O)O$^-$M$^+$ group or a molecule comprising such group, wherein M$^+$ is selected from the group consisting of lithium, sodium, magnesium, calcium, potassium, barium, iron, zinc and quaternary ammonium, and further wherein the "+" in M$^+$ does not reflect the actual number of positive charges which depends on the respective ion.

As used herein, the term "acetyl" refers to a —C(=O)CH$_3$ group.

As used herein, the term "carboxyalkyl" refers to a —(CH$_2$)$_r$C(=O)OR" group, wherein r is 1 to 6 and R" is as defined herein above.

As used herein, the term "carboxyalkyl salt" refers to a —(CH$_2$)$_r$C(=O)O$^-$M$^+$ group or a molecule comprising such group, wherein r is 1 to 6 and M$^+$ is selected from the group consisting of lithium, sodium, potassium, calcium, magnesium, barium, iron, zinc and quaternary ammonium, and further wherein the "+" in M$^+$ does not reflect the actual number of positive charges which depends on the respective ion.

As used herein, the term "carboxylic acid" refers to a C-carboxy group as defined herein above, wherein R" is hydro.

As used herein, the term "cyano" refers to a —C≡N group.

As used herein, the term "cyanato" refers to an —OCN group.

As used herein, the term "isocyanato" refers to an —NCO group.

As used herein, the term "thiocyanato" refers to an —SCN group.

As used herein, the term "isothiocyanato" refers to an —NCS group.

As used herein, the term "sulfinyl" refers to a —S(=O)R" group, R" is a $C_1$-$C_6$ alkyl.

As used herein, the term "sulfonyl" refers to a —S(=O)$_2$R" group, R" is a $C_1$-$C_6$ alkyl.

As used herein, the term "sulfonamido" refers to an —S(=O)$_2$NR$_{17}$R$_{18}$ group, wherein R$_{17}$ and R$_{18}$ are as defined herein below.

Unless specified otherwise, R$_{17}$ and R$_{18}$ are independently chosen from hydro, alkyl, aryl, carbocyclyl, heterocyclyl, —(CH$_2$)aryl, —(CH$_2$)carbocyclyl, and —(CH$_2$)heterocyclyl, wherein hydro, alkyl, aryl, carbocyclyl and heterocyclyl are as defined herein, and further wherein said alkyl, aryl, carbocyclyl, heterocyclyl, —(CH$_2$)aryl, —(CH$_2$)carbocyclyl, and —(CH$_2$)heterocyclyl can be optionally substituted. In one aspect of the embodiments provided herein, said groups that R$_{17}$ and R$_{18}$ are chosen from are unsubstituted.

As used herein, the term "trihalomethanesulfonamido" refers to an —N(R$_{17}$)S(=O)$_2$CX$_3$ group, wherein X is a halo group as defined herein above and R$_{17}$ is as defined as herein above.

As used herein, the term "O-carbamyl" refers to an —OC(=O)NR$_{17}$R$_{18}$ group, wherein R$_{17}$ and R$_{18}$ are as defined herein above.

As used herein, the term "N-carbamyl" refers to a —N(R$_{17}$)C(=O)OR$_{18}$ group, wherein R$_{17}$ and R$_{18}$ are as defined herein above.

As used herein, the term "O-thiocarbamyl" refers to an —OC(=S)NR$_{17}$R$_{18}$ group, wherein R$_{17}$ and R$_{18}$ are as defined herein above.

As used herein, the term "N-thiocarbamyl" refers to a —N(R$_{17}$)C(=S)OR$_{18}$ group, wherein R$_{17}$ and R$_{18}$ are as defined herein above.

As used herein, the term "amino" refers to a —NH$_2$ group.

As used herein, the term "alkylamino" refers to a —NR$_{23}$R$_{24}$ group, wherein R$_{23}$ and R$_{24}$ are independently chosen from —H, $C_{1-8}$ alkyl (i.e., an alkyl having 1 to 8 carbon atoms), and phenyl.

As used herein, the term "C-amido" refers to a —C(=O)NR$_{17}$R$_{18}$ group, wherein R$_{17}$ and R$_{18}$ are as defined herein above.

As used herein, the term "N-amido" refers to a —N(R$_{17}$)C(=O)R$_{18}$ group, wherein R$_{17}$ and R$_{18}$ are as defined herein above.

As used herein, the term "nitro" refers to a —NO$_2$ group.

As used herein, the term "quaternary ammonium" refers to a —NR$_{20}$R$_{21}$R$_{22}$ group, wherein R$_{20}$, R$_{21}$, and R$_{22}$ are independently selected from the group consisting of hydro and $C_{1-6}$ alkyl.

As used herein, the term "methylenedioxy" refers to an —OCH$_2$O— group, wherein the two oxygen atoms are bonded to adjacent ring carbon atoms.

As used herein, the term "ethylenedioxy" refers to an —OCH$_2$CH$_2$O— group, wherein the two oxygen atoms are bonded to adjacent ring carbon atoms.

As used herein, the term "aliphatic carbocyclic group" (or, likewise, "aliphatic carbocycle group", "aliphatic carbocyclic", "aliphatic carbocyclic" or "aliphatic carbocyclyl") refers to a radical of an aliphatic (i.e., non-aromatic) hydrocarbon ring (i.e., a monocyclic hydrocarbon ring) or of an aliphatic (i.e., non-aromatic) hydrocarbon ring system having from 2 to 4 fused rings (i.e., rings which share an adjacent pair of ring carbon atoms), wherein said monocyclic hydrocarbon ring has 3 to 8 carbon atoms and preferably is saturated, and further wherein each one of the rings forming said hydrocarbon ring system independently has 3 to 8 carbon atoms and preferably is saturated. Accordingly, aliphatic carbocyclic groups do not encompass aryls as defined herein below. Examples, without limitation, of aliphatic carbocyclic groups are cycloalkyls (such as cyclopropyl, cyclobutyl, cyclopentyl, cyclohexyl, or cycloheptyl) and cycloalkenyls (such as cycloheptatrienyl, cyclopentenyl, or cyclohexadienyl) as well as groups like indane.

As used herein, the term "cycloalkyl" refers to a cyclic saturated aliphatic hydrocarbon group which does not comprise any carbon-to-carbon double bond or any carbon-to-carbon triple bond. Preferably, the cycloalkyl has 3 to 7 carbon atoms. Non-limiting examples of cycloalkyl groups are cyclopropyl, cyclobutyl, cyclopentyl, cyclohexyl or cycloheptyl. Particularly preferred cycloalkyl groups are cyclopentyl or cyclohexyl.

As used herein, the term "cycloalkenyl" refers to a cyclic unsaturated aliphatic hydrocarbon group which comprises at least one carbon-to-carbon double bond and does not comprise any carbon-to-carbon triple bond. Preferably, the cycloalkenyl has 3 to 7 carbon atoms. Non-limiting examples of cycloalkenyl groups are cyclopropenyl, cyclobutenyl, cyclopentenyl, cyclohexenyl, cyclohexadienyl, or cycloheptenyl.

As used herein, the term "benzocycloalkyl" refers to a cycloalkyl as defined herein above, which cycloalkyl is fused to a phenyl ring (i.e., shares two adjacent ring carbon atoms with a phenyl ring). Non-limiting examples of benzocycloalkyls are indyl (i.e., 2,3-dihydro-1H-indenyl or benzocyclopentyl), 1,2,3,4-tetrahydronaphthyl (i.e., tetralinyl or benzocyclohexyl), or benzocycloheptyl. Preferred examples of benzocycloalkyls are indyl or 1,2,3,4-tetrahydronaphthyl. It is preferred that the benzocycloalkyl is attached to the remainder of the molecule via its cycloalkyl moiety (and not via its phenyl ring moiety).

As used herein, the term "heterocyclyl" or "heterocyclic" refers to ring or ring system having from 1 ring or 2 to 4 fused rings (preferably a known saturated or partially saturated 3-7 membered monocyclic ring, or known 7-10 membered bicyclic ring system) which consists of carbon atoms and from one to four heteroatoms independently selected from the group consisting of O, N, and S, wherein the nitrogen and sulfur heteroatoms can be optionally oxidized, and the nitrogen can be optionally quaternized (including e.g., any bicyclic group in which any of the above-defined heterocyclic rings is fused to a benzene ring). Non-limiting examples of saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups. Example of "heterocyclyls" or "heterocyclic" rings also include, but are not limited to, morpholino, piperidyl, piperazinyl, pyrrolidinyl, thiomorpholino, homopiperazinyl, imidazolyl, imidazolidinyl, pyrazolidinyl, dioxanyl and dioxolanyl. "Heterocyclyl" can include heteroaryls when the pi-electron system of a heterocyclyl is completely conjugated.

As used herein, the term "aryl" refers to a radical of a hydrocarbon ring (i.e., a monocyclic hydrocarbon ring) or of a hydrocarbon ring system having from 2 to 4 fused rings, wherein said monocyclic hydrocarbon ring has 5 or 6 carbon atoms and is aromatic, and further wherein each one of the rings forming said hydrocarbon ring system is aromatic and independently has 5 or 6 carbon atoms. Examples, without limitation, of aryl groups are phenyl, naphthalenyl (i.e., naphthyl) and anthracenyl. A particularly preferred aryl is phenyl.

As used herein, the term "aryloxy" refers to an —O-aryl, wherein "aryl" is as defined above.

As used herein, the term "heteroaryl" refers to a radical of a ring (i.e., a monocyclic ring) or of a ring system having from 2 to 4 fused rings, wherein said monocyclic ring has 5 or 6 members and is aromatic, and further wherein each one of the rings forming said ring system independently has 5 or 6 members and at least one of said rings forming said ring system is aromatic, wherein each of said members (i.e., ring atoms) is independently selected from C, CH, N, O, S, and at least one of the members of each ring is N, O, or S. Non-limiting examples of heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, isoxazolyl, furazanyl, phenoxazinyl, isocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2-oxobenzimidazolyl. When the heteroaryl group contains a nitrogen ring atom, such nitrogen ring atom may be in the form of an N-oxide, e.g., a pyridyl N-oxide, pyrazinyl N-oxide and pyrimidinyl N-oxide. Preferred heteroaryl groups are fully aromatic and include, but not limited to pyridyl, thienyl, and pyrimidinyl.

As used herein, the term "arylalkyl" refers to any of the $C_{1-10}$ alkyl groups substituted by any of the above-mentioned aryl groups as defined above.

Non-limiting examples of arylalkyl group include benzyl, phenethyl, and naphthylmethyl.

As used herein, the term "arylalkenyl" refers to a $C_{2-10}$ alkenyl group substituted by a $C_{6-14}$ aryl group (an aryl group having 6 to 14 carbon atoms), as defined herein above.

As used herein, the term "arylalkynyl" refers to a $C_{2-10}$ alkynyl group substituted by a $C_{6-14}$ aryl group (an aryl group having 6 to 14 carbon atoms), as defined herein above.

As used herein, the term "arylalkoxy" refers to any of the $C_{1-10}$ alkoxy groups substituted by any of the aryl groups as defined herein. Examples of arylalkoxy groups include benzyloxy and phenethyloxy.

As used herein, the term "aryloxy" refers to oxygen substituted by any of the aryl groups defined above.

As used herein, the term "arylthio" refers to a —S-aryl group, wherein the aryl group is as defined herein above.

As used herein, the term "heteroarylthio" refers to a —S-heteroaryl group, wherein the heteroaryl group is as defined herein above.

As used herein, the term "haloaryl" refers to an aryl group which is substituted with 1 to 6 halo groups, wherein the aryl group and the halo groups are as defined herein above, and further wherein the halo groups are independently selected.

As used herein, the term "acylamino" refers to a —N($R_{17}$)C(=O)$R_{18}$ group, wherein $R_{17}$ and $R_{18}$ are as defined herein above.

As used herein, the term "acyloxy" refers to an —O—C(=O)$R_{17}$ group, wherein $R_{17}$ is as defined herein above.

As used herein, the term "heteroaryloxy" refers to an —O-heteroaryl group, wherein the heteroaryl group is as defined herein above.

As used herein, the term "heteroarylalkoxy" refers to a $C_{1-10}$ alkoxy group, as defined herein above, substituted by a heteroaryl group, as defined herein above.

As used herein, the term "preventing an increase in a symptom" refers to both not allowing a symptom to increase or worsen, as well as reducing the rate of increase in the symptom. For example, a symptom can be measured as the amount of particular disease marker, i.e., a protein (e.g., cancer biomarker). In another example the symptom can be cognitive decline. Preventing an increase, according to the definition provided herein, means that the amount of symptom (e.g., protein or cognitive decline) does not increase or that the rate at which it increases is reduced.

As used herein, the term "treating a disease or disorder" refers to a slowing of or a reversal of the progress of the disease. Treating a disease or disorder includes treating a symptom and/or reducing the symptoms of the disease.

"Treatment of a disorder or disease" implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

"Treatment of a disorder or disease" may, for example, lead to a halt in the progression of the disorder or disease (e.g., no deterioration of symptoms) or a delay in the progression of the disorder or disease (in case the halt in progression is of a transient nature only). "Treatment of a disorder or disease" may also lead to a partial response (e.g., amelioration of symptoms) or complete response (e.g., disappearance of symptoms) of the subject/patient suffering from the disorder or disease. "Amelioration" of a disorder or disease may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g., the exemplary responses as described herein above).

Treatment of a disorder or disease may, inter alia, comprise curative treatment (preferably leading to a complete response and eventually to healing of the disorder or disease) and palliative treatment (including symptomatic relief).

As used herein, the term "preventing a disease or disorder" refers to a slowing of the disease or of the onset of the disease or the symptoms thereof. Preventing a disease or disorder can include stopping the onset of the disease or symptoms thereof.

For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

As used herein, the term "unit dosage form" refers to a physically discrete unit, such as a capsule or tablet suitable as a unitary dosage for a human patient. Each unit contains a predetermined quantity of a compound of Formula 1 or 2, which was discovered or believed to produce the desired pharmacokinetic profile which yields the desired therapeutic effect. The dosage unit is composed of a compound of Formula 1 in association with at least one pharmaceutically acceptable carrier, salt, excipient, or combination thereof.

As used herein, the term "dose" or "dosage" refers the amount of active ingredient that an individual takes or is administered at one time. For example, a 40 mg dose of a compound of Formula 1 or 2 refers to, in the case of a twice-daily dosage regimen, a situation where the individual takes 40 mg of a compound of Formula 1 or 2 twice a day, e.g., 40 mg in the morning and 40 mg in the evening. The 40 mg of a compound of Formula 1 or 2 dose can be divided into two or more dosage units, e.g., two 20 mg dosage units of a compound of Formula 1 or 2 in tablet form or two 20 mg dosage units of a compound of Formula 1 or 2 in capsule form.

As used herein, a "pharmaceutically acceptable prodrug" is a compound that may be converted under physiological conditions or by solvolysis to the specified compound or to a pharmaceutically acceptable salt of such compound.

The present invention also encompasses pharmaceutically acceptable prodrugs of the compounds described and defined herein, in particular prodrugs of the compounds of Formula 1 or 2. Prodrugs of the compounds of Formula 1 or 2 are derivatives which have chemically or metabolically cleavable groups and become, by solvolysis or under physiological conditions, the compounds of the present invention which are pharmaceutically active in vivo. Prodrugs of compounds of Formula 1 or 2 according to the present invention may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound employed in the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester, N,N-diethylglycolamidoester or α-acetoxyethyl ester. When a compound employed in the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)-(tert-Bu), —OC(=O)—C$_{15}$H$_{31}$, —OC(=O)-(m-COONa-Ph), —OC(=O)—CH$_2$CH$_2$COONa, —O(C=O)—CH(NH$_2$)CH$_3$ or —OC(=O)—CH$_2$—N(CH$_3$)$_2$. When a compound employed in the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

As used herein, a "pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

As used herein, a "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, and mandelates.

As used herein, a "pharmaceutically acceptable carrier" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency.

The present invention also embraces solid forms of the compounds of Formula 1 or 2 in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph.

As is understood by the skilled artisan, certain variables in the list of substituents are repetitive (different name for the same substituent), generic to other terms in the list, and/or partially overlap in content with other terms. In the compounds of the invention, the skilled artisan recognizes that substituents may be attached to the remainder of the molecule via a number of positions and the preferred positions are as illustrated in the Examples.

Additionally, the compounds of Formula 1 or 2 can contain asymmetric carbon atoms and can therefore exist in racemic and optically active forms. Thus, optical isomers or enantiomers, racemates, tautomers, and diastereomers of the compounds of Formula 1 or 2 are also encompassed in the present invention. The methods of the present invention include the use of all such isomers and mixtures thereof. Methods of separation of enantiomeric and diastereomeric mixtures are well known to one skilled in the art. Furthermore, racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active acid followed by crystallization. The present invention encompasses any isolated racemic or optically active form of compounds described in Formula 1 or 2, or any mixture thereof. In one aspect, the compounds of the invention have a trans configuration around the cyclopropyl ring as in trans-phenylcyclopropylamine. In one aspect, the compounds of the invention have a cis configuration around the cyclopropyl ring as in cis-phenylcyclopropylamine. In a preferred aspect, the compounds of Formula 1 or 2 have the trans configuration.

Typically, compounds according to Formula 1 or 2 can be effective at an amount of from about 0.01 µg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 µg to about 2000 mg, preferably from about 5 µg to about 1.000 mg.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Ailed.* 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al. (1984) *J. Pharmaceut. Sci.*, 73: 1718-1720.

Accordingly, the compounds of Formula 1 or 2 or the pharmaceutical compositions comprising a compound of Formula 1 or 2 and a pharmaceutically acceptable carrier may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e. g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal.

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham (1994) Am. J. Hosp. Pharm. 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

Examples of antineoplastic agents that can be used in combination with the compounds and methods of the present invention include, in general, and as appropriate, alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents and haematopoietic growth factors. Exemplary classes of antineoplastic include the anthracyclines, vinca drugs, mitomycins, bleomycins, cytotoxic nucleosides, epothilones, discodermolides, pteridines, diynenes and podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

Thus, in one embodiment the compound of the present invention, in particular the compound of Formula 1 or 2, can be used in combination with other therapeutic agents. When the compound is used in combination with a second therapeutic agent active against the same disease, the dose of each compound may differ from that when the compound is used alone. The combination of a compound of this invention with (an) other drug(s) may comprise the administration of the drug(s) with the compound of the invention. Such an administration may comprise simultaneous/concomitant administration. However, sequential/separate administration is also envisaged.

Preferably, the second therapeutic agent to be administered in combination with the compound of the present invention is an anticancer drug. The anticancer drug to be administered in combination with the compound of the invention may be: a tumor angiogenesis inhibitor (for example, a protease inhibitor, an epidermal growth factor receptor kinase inhibitor, or a vascular endothelial growth factor receptor kinase inhibitor); a cytotoxic drug (for example, an antimetabolite, such as purine and pyrimidine analogue antimetabolites); an antimitotic agent (for example, a microtubule stabilizing drug or an antimitotic alkaloid); a platinum coordination complex; an anti-tumor antibiotic; an alkylating agent (for example, a nitrogen mustard or a nitrosourea); an endocrine agent (for example, an adrenocorticosteroid, an androgen, an anti-androgen, an estrogen, an anti-estrogen, an aromatase inhibitor, a gonadotropin-releasing hormone agonist, or a somatostatin analogue); or a compound that targets an enzyme or receptor that is overexpressed and/or otherwise involved in a specific metabolic pathway that is misregulated in the tumor cell (for example, ATP and GTP phosphodiesterase inhibitors, histone deacetylase inhibitors, protein kinase inhibitors (such as serine, threonine and tyrosine kinase inhibitors (for example, Abelson protein tyrosine kinase)) and the various growth factors, their receptors and kinase inhibitors therefor (such as epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors)); methionine; aminopeptidase inhibitors; proteasome inhibitors; cyclooxygenase inhibitors (for example, cyclooxygenase-1 or cyclooxygenase-2 inhibitors); or topoisomerase inhibitors (for example, topoisomerase I inhibitors or topoisomerase II inhibitors).

An alkylating agent which can be used as an anticancer drug in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazines (such as temozolomide).

A platinum coordination complex which can be used as an anticancer drug in combination with a compound of the present invention may be, for example, cisplatin, carboplatin, nedaplatin, oxaliplatin, satraplatin, or triplatin tetranitrate.

A cytotoxic drug which can be used as an anticancer drug in combination with a compound of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with a compound of the present invention may be, for example, a taxane (such as docetaxel, larotaxel, ortataxel, paclitaxel/taxol, or tesetaxel), a Vinca alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumor antibiotic which can be used as an anticancer drug in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from *Streptomyces* (such as actinomycin (including actinomycin D), bleomycin, mitomycin (including mitomycin C), or plicamycin).

A tyrosine kinase inhibitor which can be used as an anticancer drug in combination with a compound of the present invention may be, for example, axitinib, bosutinib, cediranib, dasatinib, erlotinib, gefitinib, imatinib, lapatinib, lestaurtinib, nilotinib, semaxanib, sorafenib, sunitinib, or vandetanib.

A topoisomerase-inhibitor which can be used as an anticancer drug in combination with a compound of the present invention may be, for example, a topoisomerase 1 inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

Further anticancer drugs may be used in combination with a compound of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, and vorinostat.

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in proliferative diseases can be employed in co-therapy approaches with the compounds of the invention. Examples of such biological molecules are anti-HER2 antibodies (e.g. trastuzumab, Herceptin®), anti-CD20 antibodies (e.g. Rituximab, Rituxan®, MabThera®, Reditux®), anti-CD19/CD3 constructs (see, e.g., EP-A-1 071 752) and anti-TNF antibodies (see, e.g., Taylor PC. Antibody therapy for rheumatoid arthritis. *Curr Opin Pharmacol.* 2003. 3(3): 323-328). Further antibodies, antibody fragments, antibody constructs and/or modified antibodies to be used in co-therapy approaches with the compounds of the invention can be found in Taylor PC. *Curr. Opin. Pharmacol.* 2003. 3(3):323-328; Roxana A. Maedica. 2006. 1(1):63-65.

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the present compound or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

In another embodiment, the compounds of the present invention, in particular the compounds of Formula 1 or 2, are administered in combination with physical therapy, such as radiotherapy. Radiotherapy may commence before, after, or simultaneously with administration of the compounds. For example, radiotherapy may commence 1 to 10 minutes, 1 to 10 hours or 24 to 72 hours after administration of the compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens. Without being bound by theory, the compounds of the present invention may be used to render cells, in particular undesired proliferative/hyperproliferative cells like cancer or tumor cells, more susceptible to such a physical therapy, e.g. radiotherapy.

Accordingly, the present invention relates to a compound of Formula 1 or a pharmaceutically acceptable salt or solvate thereof, or a pharmaceutical composition comprising any of the aforementioned entities in combination with a pharmaceutically acceptable carrier, for use in the treatment or prevention of cancer, whereby the compound or the pharmaceutical composition is to be administered in combination with an anti-proliferative drug, an anticancer drug, a cytostatic drug, a cytotoxic drug and/or radiotherapy.

In the context of the present invention, the "subject", "patient" or "individual", such as the subject in need of treatment or prevention, may be an animal, a vertebrate animal, a mammal, a rodent (e.g. a guinea pig, a hamster, a rat, a mouse), a murine (e.g. a mouse), a canine (e.g. a dog), a feline (e.g. a cat), an equine (e.g. a horse), a primate, a simian (e.g. a monkey or ape), a monkey (e.g. a marmoset, a baboon), an ape (e. g. gorilla, chimpanzee, orangutan, gibbon), or a human. The meaning of the terms "animal", "mammal", etc. is well known in the art and can, for example, be deduced from Wehner and Gehring (1995; Thieme Verlag). In the context of this invention, it is particularly envisaged that animals are to be treated which are economically, agronomically or scientifically important. Scientifically important organisms include, but are not limited to, mice, rats, and rabbits. Non-limiting examples of agronomically important animals are sheep, cattle and pig, while, for example, cats and dogs may be considered as economically important animals. Preferably, the subject/patient/individual is a mammal. More preferably, the subject/patient/individual is a human.

General Synthetic Route Description

The compounds of the invention can be synthesized by the general route described in Schemes 1, 2, 3, 4 and 5. Note that the compounds formula (I) and formula (II) as described below in the synthetic description and schemes are intended to be different than the compounds of Formula 1 and compounds of Formula 2 as described above in the embodiments/aspects of the invention (or in the claims).

Commercially available nitro derivatives of formula (I) are subjected to a cyclopropanation reaction using trimethylsulfoxonium iodide and potassium tert-butylate. The nitro group of the resulting nitrocyclopropyl derivatives of formula (II) are then reduced using zinc in hydrochloric acid to afford the cyclopropylamino derivatives of formula (III). These compounds of formula (III) can react with t-butyl dicarbonate at room temperature using triethylamine as a base and tetrahydrofuran as a solvent leading intermediate of formula (IV). Alkylation of the derivatives of formula (IV) with commercially available alkyl halide derivatives of formula (V), using NaH as a base and DMF as a solvent, leads to the intermediates of formula (VI). Deprotection of the Boc-group using HCl in diethyl ether leads to the formation of derivatives of formula (VII), which are subject of the present invention.

Alternatively, the reaction of the cyclopropylamino derivatives of formula (III) with commercially available aldehydes of formula (VIII), using sodium triacetoxyborohydride as reductive agent and dichloroethane as solvent also leads to the formation of derivatives of formula (VII), which are subject of the present invention.

Scheme 1: DMF (N,N-dimethylformamide), DMSO (Dimethyl sulfoxide), EDC (dichloroethane), THF (Tetrahydrofuran)

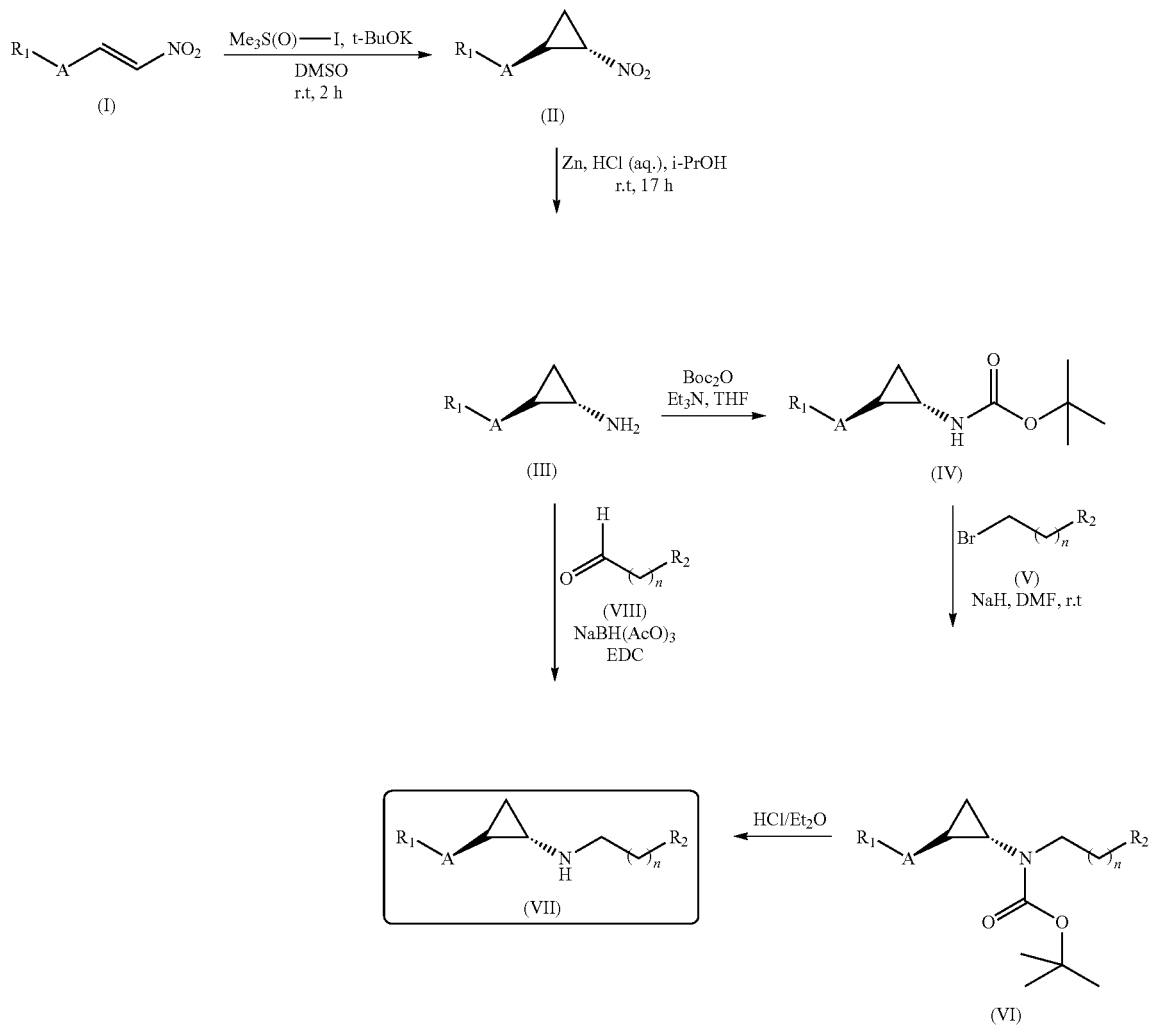

Scheme 2: ACN (Acetonitrile), DMF (N,N-dimethylformamide), EDC (dichloroethane)

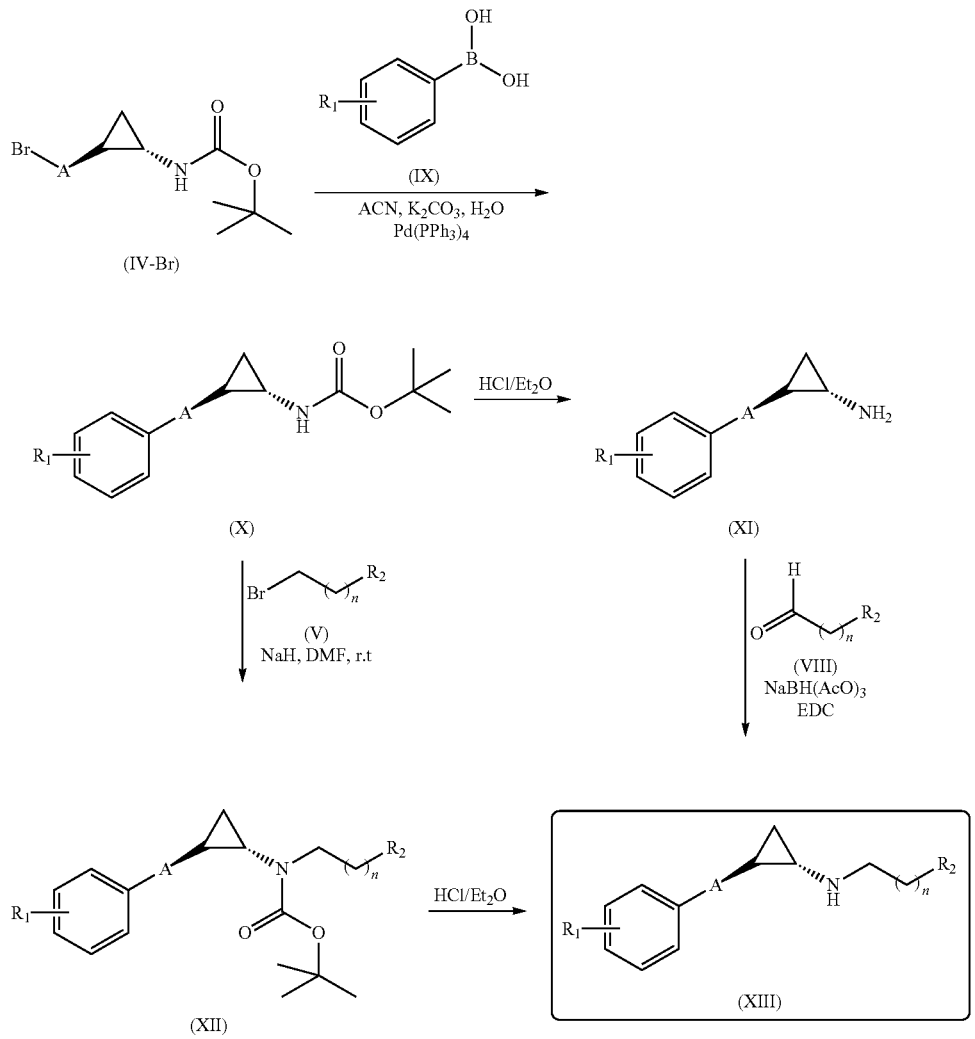

The reaction of the intermediate of formula (IV-Br) with commercially available boronic acid derivatives of formula (IX), using acetonitrile and water as a solvent, potassium carbonate as a base and Tetrakis(triphenylphospine) Palladium (0) as a catalyst leads to the formation of the compounds of formula (X). Deprotection of the Boc-group using HCl in Et$_2$O results in the formation of the derivatives of formula (XI). These compounds of formula (XI) react with commercially available aldehydes of formula (VIII), using sodium triacetoxyborohydride as reductive agent and dichloroethane as solvent leading to the formation of compounds of formula (XIII), also subjects of the present invention.

Alternatively, the alkylation of the derivatives of formula (X) with commercially available alkyl halide derivative compounds of formula (V), using NaH as a base and DMF as a solvent, leads to the intermediates of formula (XII). Later deprotection of the Boc-group using HCl in diethyl ether also allows the formation of derivatives of formula (XIII), which are also subject of the present invention.

Scheme 3: DMSO (Dimethyl sulfoxide), EDC (dichloroethane)

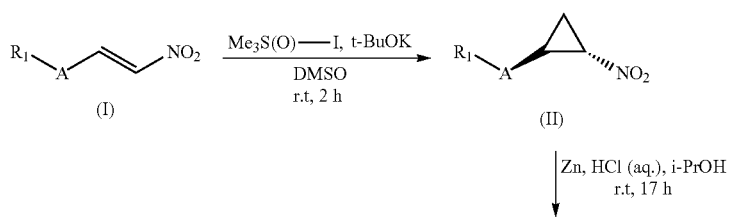

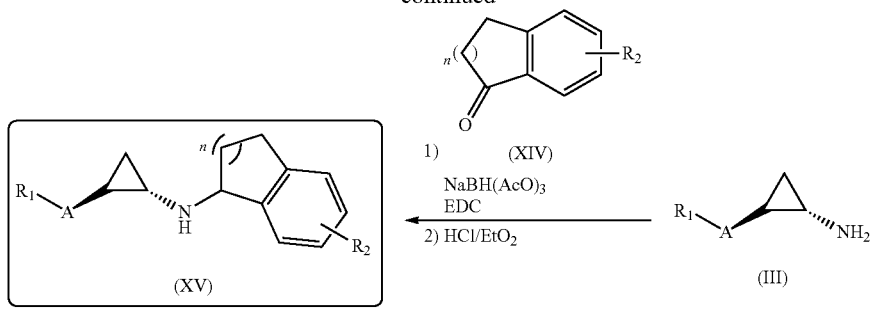

Commercially available nitro derivatives of formula (I) are subjected to a cyclopropanation reaction using trimethylsulfoxonium iodide and potassium tert-butylate. The nitro group of the resulting nitrocyclopropyl derivatives of formula (II) are then reduced using zinc in hydrochloric acid to afford the cyclopropylamino derivatives of formula (III). These compounds of formula (III) can react with commercially available ketones of formula (XIV), using sodium triacetoxyborohydride as reductive agent and dichloroethane as solvent to get derivatives of formula (XV), which are also subject of the present invention.

The reaction of compounds of formula (IV-Br) with commercially available boronic acid derivatives of formula (IX), using acetonitrile and water as a solvent, potassium carbonate as a base and Tetrakis(triphenylphospine) Palladium (0) as a catalyst leads to the formation of the compounds of formula (X). Deprotection of the Boc-group using HCl in Et$_2$O results in the formation of the derivatives of formula (XI). These derivatives (e.g., of formula (XI)) react with commercially available ketones of formula (XIV), using sodium triacetoxyborohydride as reductive agent and dichloroethane as solvent to give compounds of formula (XVI), which are also subject of the present invention.

Scheme 4: ACN (Acetonitrile), EDC (dichloroethane)

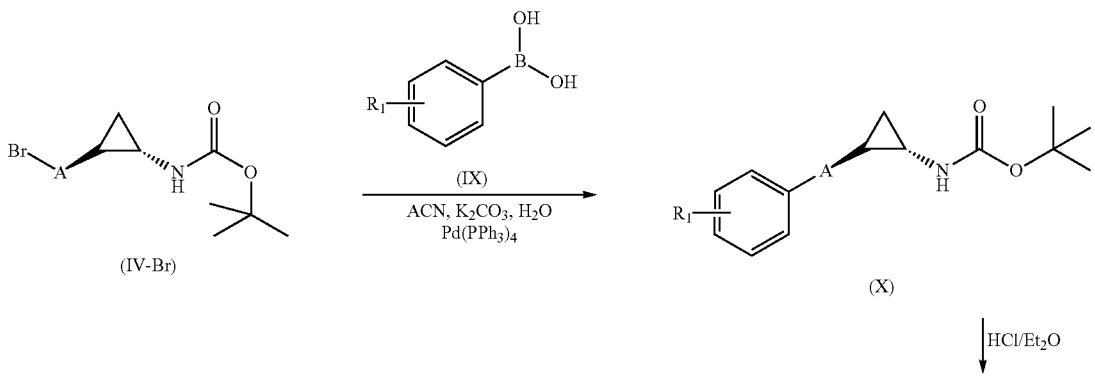

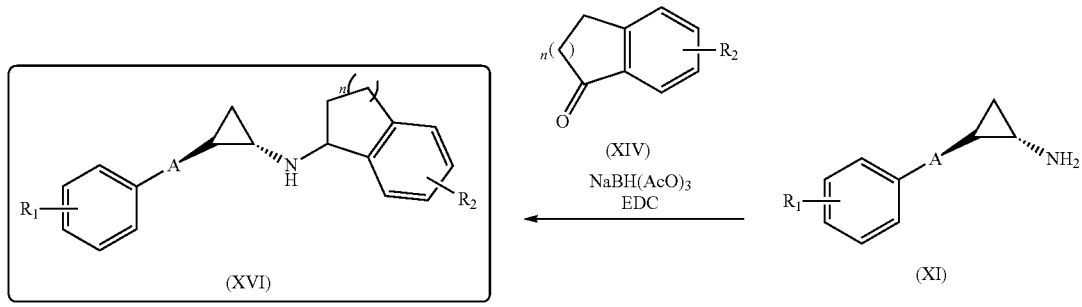

Scheme 5: EDC (dichloroethane), DMF (N,N-Dimethylformamide), DMSO (Dimethyl sulfoxide), MEM—Cl (methoxyethoxymethyl chloride), p-TsOH (p-Toluenesulfonic acid), THF (Tetrahydrofuran).
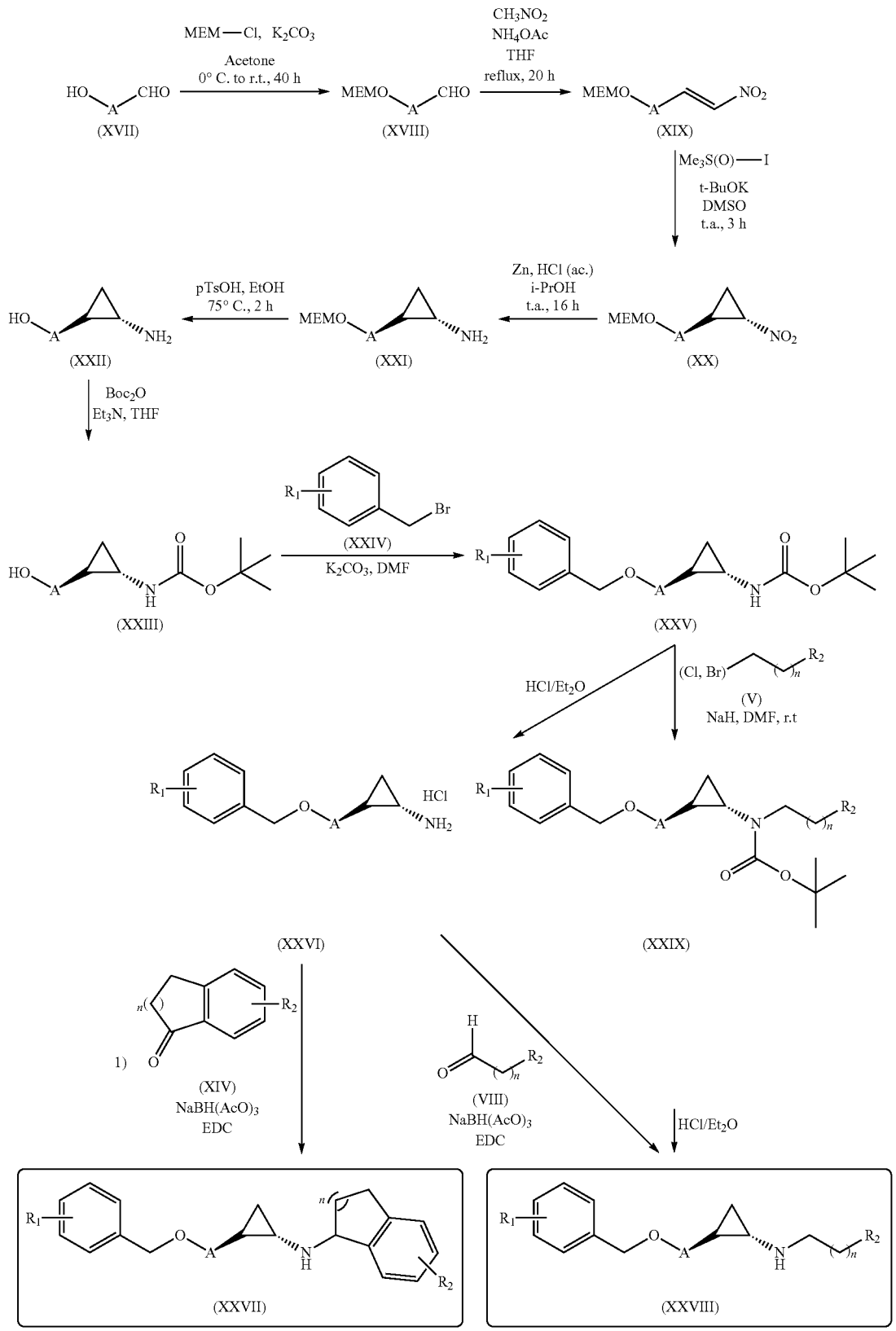

The reaction of commercially available aldehydes of formula (XVII) with methoxyethoxymethyl chloride in acetone using potassium carbonate as a base leads to the formation of aldehyde derivatives of formula (XVIII). These compounds react with nitromethane and ammonium acetate in tetrahydrofuran to get the nitrovinyl derivatives of formula (XIX). Cyclopropanation reaction using trimethylsulfoxonium iodide and sodium hydride in dimethyl sulfoxide as a solvent leads to the formation of (trans)-nitrocyclopropane derivatives of formula (XX). The nitro group has been then reduced using zinc in hydrochloric acid to afford the (trans)-cyclopropylamino derivatives of formula (XXI). The deprotection using p-toluenesulfonic acid in ethanol leads to the formation of derivatives of formula (XXII). Reaction with t-butyl dicarbonate in tetrahydrofuran using triethylamine as a base leads to tert-butyl (trans)-cyclopropylcarbamate derivatives of formula (XXIII). Alkylation with commercially available benzyl bromide derivatives of formula (XXIV) using potassium carbonate as a base and N,N-dimethylformamide as a solvent results in the formation of derivatives of formula (XXV). Boc-deprotection of these derivatives using HCl 2M in diethyl ether using diethyl ether as a solvent leads to the formation of the corresponding hydrochloride salt of the (trans)-cyclopropylamino derivatives of formula (XXVI). These amine derivatives could be alkylated in two ways:
1) With commercially available ketones of formula (XIV), using sodium triacetoxyborohydride as reductive agent and dichloroethane as solvent to get compounds of formula (XXVII), which are also subject of the present invention. 2) With commercially available aldehydes of formula (VIII), using sodium triacetoxyborohydride as reductive agent and dichloroethane as solvent to get compounds of formula (XXVIII), which are also subject of the present invention.

Alternatively, the alkylation of the cyclopropylcarbamate derivatives of formula (XXV) with commercially available alkyl halides of formula (V), using NaH as a base and DMF as a solvent, leads to intermediates of formula (XXIX). Later deprotection of the Boc-group using HCl in diethyl ether also allows the formation of compounds of formula (XXVIII), which are also subject of the present invention.

The skilled artisan is capable of selecting or synthesizing other alkylating reagents in place of those of Formula (V), (VIII), (XIV), and (XXIV) to synthesize the compounds of the invention.

In the above described schemes, the A-group can be an aryl group, which is exemplified in the Examples as a phenyl group and the A-group can also be for example a heteroaryl group (e.g., pyridyl or other heteroaryl). The skilled artisan can readily modify the synthetic schemes described herein to make compounds which have heteroaryl groups in the A-position.

EXAMPLES

The program used to generate the names corresponding to the structures in the Example compounds below was ChemBioDraw Ultra version 11.0.1 by CambridgeSoft. In the case of conflict between a name and a drawn structure, the drawing controls the definition. This program named the molecules as the (1S,2R) configuration due to the configuration of the input structure and the "trans" term has been substituted in the place of the (1S,2R) term specified by the program. The structures depicted below are shown as having one particular stereochemical configuration around the cyclopropyl carbon atoms of the phenylcyclopropylamine core (1S,2R). All the compounds synthesized in the Examples are mixtures having both configurations (1R,2S) and (1S,2R), that is to say they are "trans" in respect to the cyclopropyl ring of the cyclopropyl ring system. This is due to the fact the phenylcyclopropylamine starting material used is "trans". It is contemplated that the cis configuration starting material or the individual diastereomers could be used as starting material, all of which are either commercially or synthetically available. Thus, the invention relates to compounds that have specific stereochemical configurations around the cyclopropyl ring e.g., trans ((1R,2S) and (1S,2R)) and cis ((1R,2R) and (1S,2S)) or the individual diastereomers thereof. A preferred stereochemical configuration around the cyclopropyl ring of phenylcyclopropylamine is trans.

The compounds of the examples can also be synthesized or provided in a salt form. The skilled artisan is aware and capable of making salt forms and/or converting salt forms of the compounds of the invention including those of the Examples. In some cases the compounds of the invention, including those of the Examples can be more stable as salt forms as compared to free base.

In reference to the synthetic schemes described herein the following intermediates (and analogous intermediates or derivatives thereof) can be made using the following procedures. The ordinary skilled artisan is capable of making modifications to these schemes or use alternatives to arrive at the compounds of the invention.

Intermediate A: (Trans)-2-phenylcyclopropanamine

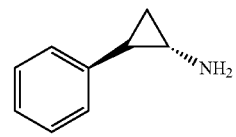

NaOMe (0.80 g, 11.8 mmol) was added over a solution of (trans)-2-phenylcyclopropanamine hydrochloride (2.00 g, 11.8 mmol) in MeOH (40 mL) and stirred 1 hour. The solvent was removed to dryness.

Intermediate B: tert-butyl (trans)-2-phenylcyclopropylcarbamate

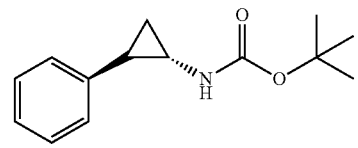

Over a solution of (trans)-2-phenylcyclopropanamine (intermediate A, 1.14 g, 1 eq) in 50 mL of THF, 1.25 g (1.05 eq) of $K_2CO_3$ was added and stirred 3 hours at room temperature. After removal of the solvent, $CH_2Cl_2$ was added, then washed with a saturated solution of $NaHCO_3$ and brine. The organic layer was extracted, dried with $MgSO_4$ and filtered. The crude was purified by silica gel chromatography (Hexane-MTBE 90:10) affording 1.89 g of tert-butyl (trans)-2-phenylcyclopropylcarbamate. Yield: 95%

Intermediate C: 1-(benzyloxy)-4-[(trans)-2-nitrocyclopropyl]benzene

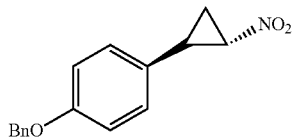

Trimethylsulfoxonium iodide (0.62 g, 2.82 mmol) was added in portions to a solution of t-BuOH (0.32 g, 2.82 mmol) in dry DMSO (5 mL). After 10 min a solution of 1-(benzyloxy)-4-[(E)-2-nitrovinyl]benzene (0.60 g, 2.35 mmol) in DMSO (5 mL) was transferred via canula and the mixture was stirred at room temperature for 6 h. The reaction was poured over water (10 mL) and extracted with Et₂O (3×10 mL); the organic layers were washed with brine (2×15 mL), dried over anhydrous Na₂SO₄ and filtered. After removal of the solvent, the residual orange oil was purified by column chromatography on silica gel (5% EtOAc/hexanes) affording 0.16 g of 1-(benzyloxy)-4-[(trans)-2-nitrocyclopropyl]benzene [Rf=0.5 (20% EtOAc/hexanes), white solid, 26% yield].

Intermediate D: (Trans)-2-[4-(benzyloxy)phenyl]cyclopropanamine

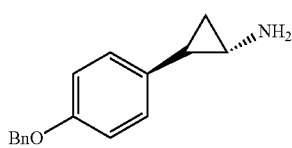

Zn dust (1.97 g, 30 mol) was added in small portions, over a period of 30 min, to a vigorously stirred solution of 1-(benzyloxy)-4-[(trans)-2-nitrocyclopropyl]benzene (Intermediate C, 0.81 g, 3.0 mmol) in i-PrOH (25 mL) and HCl (11 mL of aqueous solution 2.7 N, 30 mmol). After 17 h the mixture was filtered through a pad of celite that was washed with 10 mL of methanol. The filtrate was concentrated and 10 mL of water were added, washing with CH₂Cl₂ (3×15 mL). The organic layers were dried over anhydrous Na₂SO₄ and filtered. After removal of the solvent, the crude product was purified by column chromatography on silica gel (10% MeOH/CH₂Cl₂) affording 0.50 g of (trans)-2-[4-(benzyloxy)phenyl]cyclopropanamine [Rf=0.2 (10% MeOH/CH₂Cl₂), white solid, 70% yield]. ¹H NMR δ (ppm): MeOH 400 MHz: 7.45-7.27 (m, 5H, ArH); 6.96 (d, J=8.5 Hz, 2H, ArH); 6.86 (d, 8.5 Hz, 2H, ArH); 5.03 (s, 2H, CH2); 2.41-2.34 (m, 1H, CH); 1.86-1.76 (m, 1H, CH); 0.98-0.85 (m, 2H, CH2).

Intermediate E: Tert-butyl (trans)-2-[4-(benzyloxy)phenyl]cyclopropylcarbamate

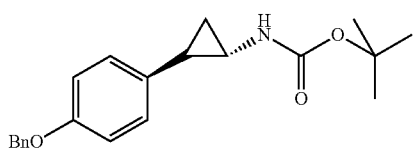

Boc₂O (1.65 equiv) was added to a solution of (Trans)-2-[4-(benzyloxy)phenyl]cyclopropanamine (Intermediate D; 1 equiv.) and Et₃N (1.65 equiv) in THF and stirred for 3 h. After removal of the solvent, the crude residue was dissolved in EtOAc and consecutively washed with water and HCl (10% aqueous solution) and brine. The organic layer was dried over anhydrous Na₂SO₄ and filtered; after removal of the solvent, the residue was purified by column chromatography on silica gel (10-20% EtOAc/Hexanes), affording the target compound (Yield 78%). ¹H NMR δ (ppm):MeOH 400 MHz: 7.45-7.27 (m, 5H, ArH); 6.93 (d, J=8.5 Hz, 2H, ArH); 6.86 (d, J=8.5 Hz, 2H, ArH); 5.03 (s, 2H, CH2); 2.41-2.34 (m, 1H, CH); 1.86-1.76 (m, 10H, CH; tBu); 0.98-0.85 (m, 2H, CH2).

Intermediate F: 1-bromo-4-[(trans)-2-nitrocyclopropyl]benzene

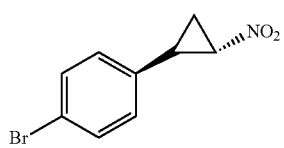

This compound was synthesized using the same methodology described in Intermediate C, using the commercially available (E)-1-bromo-4-(2-nitrovinyl)benzene as starting material. Yield: 27%.

Intermediate G: (trans)-2-(4-bromophenyl)cyclopropanamine

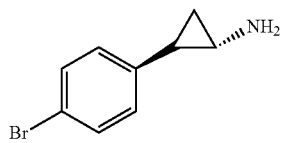

This compound was synthesized using the same methodology described in Intermediate D, using as starting material 1-bromo-4-[(trans)-2-nitrocyclopropyl]benzene (intermediate F). Yield: 10%. ¹HNMR (CD₃OD): 1.45 (m, 2H), 2.61 (m, 1H), 2.86 (m, 1H), 6.98 (d, 2H), 7.11 (d, 2H). MS (M+H): 211.9.

Intermediate H: Tert-butyl (trans)-2-(4-bromophenyl)cyclopropylcarbamate

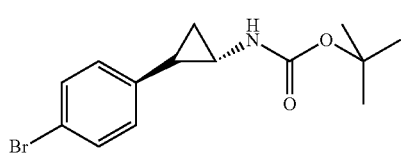

Boc₂O (1.65 equiv) was added to a solution of (trans)-2-(4-bromophenyl)cyclopropanamine (Intermediate G; 1 equiv.) and Et₃N (1.65 equiv) in THF and stirred for 3 h. After removal of the solvent, the crude residue was dissolved in EtOAc and consecutively washed with water and HCl (10% aqueous solution) and brine. The organic layer was dried over anhydrous Na$_2$SO$_4$ and filtered; after removal of the solvent, the residue was purified by column chromatography on silica gel (10-20% EtOAc/Hexanes), affording tert-butyl (trans)-2-(4-bromophenyl)cyclopropylcarbamate (Yield 85%).

Intermediate I: 4-((2-methoxyethoxy)methoxy)benzaldehyde

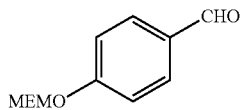

2-Methoxyethoxymethyl chloride (5.10 mL, 45.0 mmol) was slowly added to a mixture of 4-hydroxybenzaldehyde (5.00 g, 40.9 mmol) and K$_2$CO$_3$ (6.20 g, 45.0 mmol) in acetone (70 mL) cooled at 0° C. The mixture was allowed to reach room temperature and stirred for 40 h. After removal of the solvent, the crude residue was dissolved in EtOAc (50 mL) and consecutively washed with water (50 mL) and NaOH (10% aqueous solution, 2×20 mL). The organic layer was dried over anhydrous Na$_2$SO$_4$ and filtered. After removal of the solvent, 6.85 g of 4-((2-methoxyethoxy)methoxy)benzaldehyde were obtained [Rf=0.6 (50% AcOEt/Hexanes), colorless oil, 80% yield], that were used without further purification.

Intermediate J: (E)-1-((2-methoxyethoxy)methoxy)-4-(2-nitrovinyl)benzene

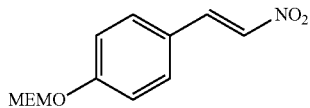

A mixture of 4-((2-methoxyethoxy)methoxy)benzaldehyde (Intermediate I, 1.86 g, 8.85 mmol) and NH$_4$OAc (0.75 g, 9.73 mmol) in dry THF (15 mL) and CH$_3$NO$_2$ (15 mL) was refluxed for 20 h and allowed to reach room temperature. The volume of the reaction was reduced to approx. ⅓, by rotatory evaporation; the resulting solution was poured into water (15 mL) and extracted with AcOEt (2×15 mL). The organic layers were washed with brine (20 mL), dried over anhydrous Na$_2$SO$_4$ and filtered. After removal of the solvent, the residual brown oil was purified by column chromatography on silica gel (15-30% EtOAc/Hexanes) affording 1.77 g of (E)-1-((2-methoxyethoxy)methoxy)-4-(2-nitrovinyl)benzene [Rf=0.7 (50% AcOEt/Hexanes), yellow solid, 79% yield].

Intermediate K: 1-((2-methoxyethoxy)methoxy)-4-((trans)-2-nitrocyclopropyl)benzene

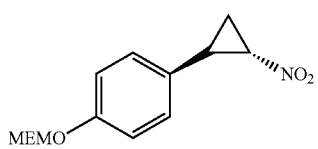

Trimethylsulfoxonium iodide (0.76 g, 3.44 mmol) was added in small portions to a suspension of NaH 0.14 g (60% in mineral oil), 3.44 mmol] in dry DMSO (5 mL). The mixture was stirred until gas evolution ceased and a clear solution was formed (45 min). Then, a solution of (E)-1-((2-methoxyethoxy)methoxy)-4-(2-nitrovinyl)benzene (Intermediate J, 0.73 g, 2.86 mmol) in DMSO (5 mL) was transferred via cannula and the reaction was stirred for additional 20 h. The mixture was poured into water (20 mL) and extracted with Et$_2$O (3×15 mL). The organic layers were washed with brine (20 mL), dried over anhydrous Na$_2$SO$_4$ and filtered; after removal of the solvent, the residual orange oil was purified by column chromatography on silica gel (10-20% EtOAc/Hexanes) affording 0.44 g of 1-((2-methoxyethoxy)methoxy)-4-((trans)-2-nitrocyclopropyl)benzene [Rf=0.4 (50% AcOEt/Hexanes), colorless oil, 36% yield].

Intermediate L: (trans)-2-(4-((2-methoxyethoxy)methoxy)phenyl)cyclopropanamine

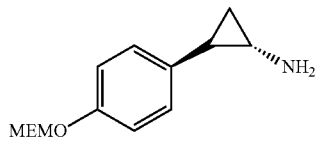

Zn dust (0.99 g, 15.1 mol) was added in small portions, over a period of 20 min, to a vigorously stirred solution of 1-((2-methoxyethoxy)methoxy)-4-((trans)-2-nitrocyclopropyl)benzene (Intermediate K, 0.40 g, 1.51 mmol) in i-PrOH (15 mL) and HCl (5.6 mL of 2.7 N aqueous solution, 15.1 mmol). After 16 h, the mixture was basified with NaOH (10% aqueous solution, 10 mL) and filtered through a pad of celite, that was washed with 10 mL of methanol. The filtrate was concentrated and 15 mL of water were added, extracting with CH$_2$Cl$_2$ (3×15 mL); the organic layers were washed with brine (25 mL), dried over anhydrous Na$_2$SO$_4$ and filtered. After removal of the solvent, the crude product was purified by column chromatography on silica gel (2-5% MeOH/CH$_2$Cl$_2$) affording 0.26 g of (trans)-2-(4-((2-methoxyethoxy)methoxy)phenyl)cyclopropanamine [Rf=0.1 (5% MeOH/CH$_2$Cl$_2$), white solid, 73% yield].

Intermediate M: 4-((trans)-2-aminocyclopropyl)phenol

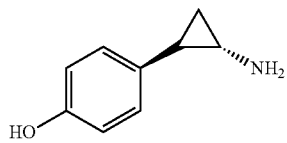

A solution of (trans)-2-(4-((2-methoxyethoxy)methoxy)phenyl)cyclopropanamine (Intermediate L, 62 mg, 0.26 mmol) and p-TsOH.H$_2$O (60 mg, 0.31 mmol) in EtOH (5 mL) was heated at 75° C. for 2 h. The pH of the reaction was adjusted to 7 with NaOH (10% aqueous solution), the mixture was poured into water (10 mL) and extracted with EtOAc (4×10 mL). The organic layer was washed with brine (10 mL), dried over anhydrous Na$_2$SO$_4$ and filtered. After removal of the solvent a brownish residue was obtained (44 mg, 4-((trans)-2-aminocyclopropyl)phenol contaminated with p-TsOH) that was used in the next step without further purification.

Intermediate N: tert-butyl (trans)-2-(4-hydroxyphenyl)cyclopropylcarbamate

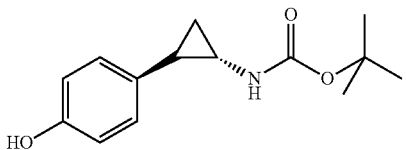

Boc₂O (94 mg, 0.43 mmol) was added to a solution of 4-((trans)-2-aminocyclopropyl)phenol (Intermediate M, 0.26 mmol) and Et₃N (59 µL, 0.43 mmol) in THF (4 mL) and stirred for 3 h. After removal of the solvent, the crude residue was dissolved in EtOAc (10 mL) and consecutively washed with [water (5 mL) and HCl (10% aqueous solution, 1 mL)] and brine (5 mL). The organic layer was dried over anhydrous Na₂SO₄ and filtered; after removal of the solvent, the residue was purified by column chromatography on silica gel (10-20% EtOAc/Hexanes), affording 26 mg of tert-butyl (trans)-2-(4-hydroxyphenyl)cyclopropylcarbamate [Rf=0.7 (50% AcOEt/Hexanes), colorless oil, 40% yield].

¹H-NMR (CDCl₃, 250 MHz, δ): 1.10-1.02 (m, 2H), 1.46 (s, 9H), 1.99-1.94 (m, 1H), 2.66 (br, 1H), 4.90 (br, 1H), 6.46 (br, 1H), 6.69 (d, 2H), 6.93 (d, 2H).

Example 1: N-((trans)-2-(4-(benzyloxy)phenyl)cyclopropyl)-6-methoxy-2,3-dihydro-1H-inden-1-amine hydrochloride

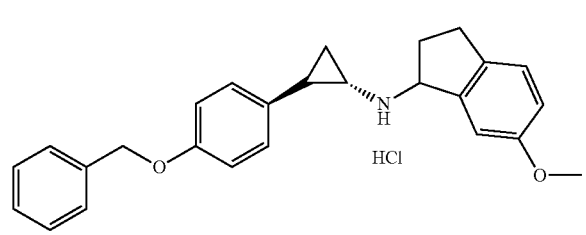

To a solution of (trans)-2-(4-(benzyloxy)phenyl)cyclopropanamine (Intermediate D, 150 mg, 0.627 mmol) and 2,3-dihydro-6-methoxyinden-1-one (132 mg, 0.815 mmol) in DCE (10 mL) sodium triacetoxy borohydrate (159.5, 0.752 mmol) was added slowly at 0° C. and stirred at room temperature for 5 h. The reaction mixture was evaporated under reduced pressure. The residue was dissolved in methanol (15 mL) and NaBH₄ (47.5 mg, 1.25 mmol) was added slowly to the reaction mixture at 0° C. and stirred for 3 h. After completion of reaction, the reaction mixture was poured into water (100 mL) and extracted with EtOAc (2×100 mL). The combined organic layers were washed with brine (100 mL) and dried over anhydrous Na₂SO₄, filtered and evaporated under reduced pressure. The crude was purified by prep HPLC to give (70 mg, 29.1%) of N-((trans)-2-(4-(benzyloxy)phenyl)cyclopropyl)-6-methoxy-2,3-dihydro-1H-inden-1-amine. HCl in dioxane (20 mL) was added and stirred at room temperature for 30 min. The solvent was evaporated to give N-((trans)-2-(4-(benzyloxy)phenyl)cyclopropyl)-6-methoxy-2,3-dihydro-1H-indane-1-amine hydrochloride (72 mg. Yield=94%) as a pale yellow solid. ¹H-NMR (DMSO-d6) δ (ppm): 1.26 (m, 1H), 1.51-1.59 (m, 1H), 2.29 (m, 1H), 2.45 (m, 1H), 2.80 (m, 2H), 3.02 (m, 1H), 3.64 (d, 3H), 4.85 (br, 1H), 5.09 (s, 2H), 6.92 (m, 3H), 7.09 (t, 2H), 7.25 (m, 2H), 7.37 (m, 1H), 7.42 (m, 5H), 9.70 (br, 1H), 9.90 (br, 1H). MS (M+H): 386.1.

The following compounds can be synthesized following the method described for Example 1 using the corresponding trans-cyclopropylamine derivative and the commercially available cyclic ketones.

Example 2: N-((trans)-2-(4-(benzyloxy)phenyl)cyclopropyl)-5,6-dimethoxy-2,3-dihydro-1H-inden-1-amine hydrochloride

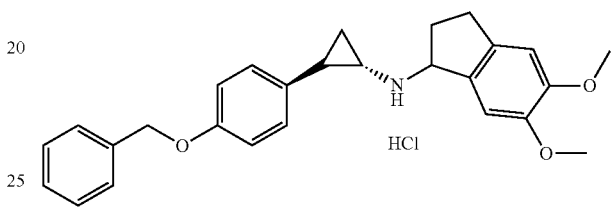

¹H-NMR (DMSO-d6) δ (ppm): 1.25 (m, 1H), 1.50 (m, 1H), 2.29 (m, 1H), 2.42 (m, 1H), 2.78 (m, 1H), 2.89 (br, 1H), 3.03 (m, 1H), 3.54-3.59 (s, 3H), 3.74 (d, 3H), 4.80 (br, 1H), 5.09 (s, 2H), 6.92 (m, 3H), 7.09 (m, 3H), 7.41 (m, 5H), 9.49 (br, 1H), 9.58 (br, 1H). MS (M+H): 416.3.

Example 3: N-((trans)-2-(4-(benzyloxy)phenyl)cyclopropyl)-4,5-dimethoxy-2,3-dihydro-1H-inden-1-amine hydrochloride

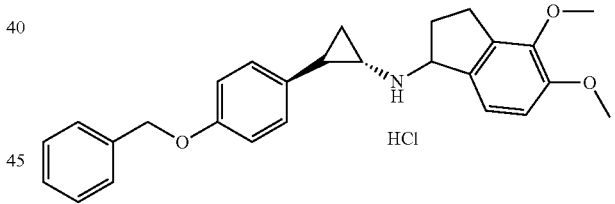

¹H-NMR (DMSO-d6) δ (ppm): 1.24 (m, 1H), 1.42-1.52 (m, 1H), 2.33 (m, 1H), 2.42 (m, 2H), 2.81 (m, 2H), 3.04 (m, 1H), 3.65-3.70 (s, 3H), 3.79 (s, 3H), 4.81 (br, 1H), 5.08 (s, 2H), 6.95 (m, 3H), 7.03 (d, 1H), 7.09 (d, 1H), 7.27 (d, 1H), 7.33 (d, 1H), 7.42 (m, 4H), 9.48 (br, 1H), 9.58 (br, 1H). MS (M+H): 224.5.

Example 4: N-((trans)-2-phenylcyclopropyl)-2,3-dihydro-1H-inden-1-amine hydrochloride

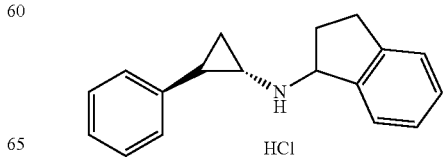

¹H-NMR (CD3OD) δ (ppm): 1.43 (qd, 1H), 1.50-1.59 (m, 1H), 2.40 (m, 1H), 2.47 (m, 1H), 2.59 (m, 1H), 2.99 (m, 2H), 3.17 (m, 1H), 4.98 (dd, 1H), 7.12 (q, 2H), 7.26 (t, 1H), 7.31 (m, 3H), 7.37 (m, 2H), 7.55 (t, 1H). MS (M+H): 249.9.

Example 5: 6-methoxy-N-((trans)-2-phenylcyclopropyl)-2,3-dihydro-1H-inden-1-amine

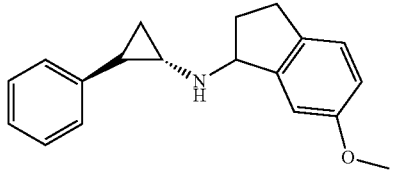

¹H-NMR (CDCl3) δ (ppm): 1.03 (m, 1H), 1.16 (m, 1H), 1.94-2.00 (m, 214), 2.47-2.50 (m, 2H), 2.74 (m, 1H), 2.90 (m, 1H), 3.69-3.76 (s, 314), 4.32 (m, 1H), 6.74 (d, 1H), 6.81 (s, 1H), 6.89 (s, 1H), 7.03 (d, 2H), 7.11 (d, 2H), 7.16 (d, 1H), 7.24 (m, 1H). MS (M+H): 280.0.

Example 6: 6-chloro-N-((trans)-2-phenylcyclopropyl)-2,3-dihydro-1H-inden-1-amine hydrochloride

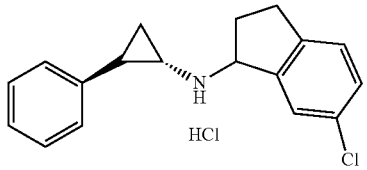

¹H-NMR (CD3OD) δ (ppm): 1.43 (qd, 1H), 1.56 (m, 1H), 2.45 (m, 2H), 2.61 (m, 1H), 2.98 (m, 2H), 3.15 (m, 1H), 4.98 (dd, 1H), 7.12 (q, 2H), 7.25 (m, 1H), 7.31 (m, 3H), 7.36 (m, 1H), 7.58 (s, 1H). MS (M+H): 284.0/286.0.

Example 7: N-((trans)-2-phenylcyclopropyl)-6-(trifluoromethyl)-2,3-dihydro-1H-inden-1-amine hydrochloride

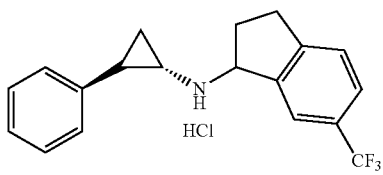

¹H-NMR (CD3OD) δ (ppm): 1.47 (m, 1H), 1.55 (m, 1H), 2.45 (m, 2H), 2.66 (m, 1H), 3.07 (m, 2H), 3.22 (m, 1H), 5.08 (td, 1H), 7.12 (dd, 2H), 7.26 (d, 1H), 7.31 (m, 2H), 7.56 (dd, 1H), 7.70 (t, 1H), 7.85 (d, 1H). MS (M+H): 318.0.

Example 8: 7-methoxy-N-((trans)-2-phenylcyclopropyl)-1,2,3,4-tetrahydronaphthalen-1-amine

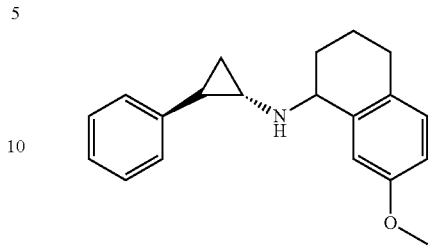

¹H-NMR (CDCl3) δ (ppm): 1.04 (m, 1H), 1.12-1.18 (m, 1H), 1.56 (m, 4H), 1.72 (m, 1H), 1.92 (m, 2H), 1.98 (m, 1H), 2.42-2.50 (m, 1H), 2.72 (m, 2H), 3.66-3.76 (s, 3H), 3.86 (m, 1H), 6.72 (m, 1H), 6.82 (s, 1H), 6.92 (s, 1H), 6.98 (d, 1H), 7.06 (t, 3H), 7.16 (t, 1H). MS (M+H): 294.0.

Example 9: N-((trans)-2-(3'-chlorobiphenyl-4-yl)cyclopropyl)-6-methoxy-2,3-dihydro-1H-inden-1-amine hydrochloride

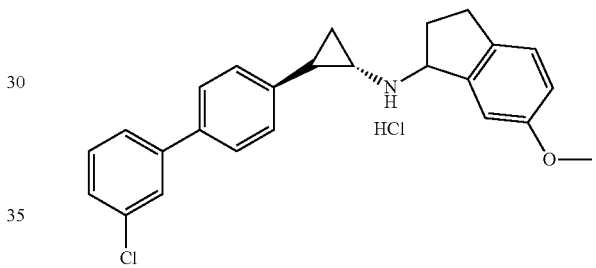

Step 1:
A solution of tert-butyl (trans)-2-(4-bromophenyl)cyclopropylcarbamate (Intermediate H, 3 g, 9.6 mmol), 3-chlorophenylboronic acid (1.8 g, 11.5 mmol) and $K_2CO_3$ (3.9 g, 28.8 mmol) in acetonitrile: water (4:1) was degassed for 20 min. Tetrakis triphenylphosphine palladium (300 mg) was added and heated at reflux for 18 h. After completion, the reaction mixture was poured into ice water (100 mL) and extracted with EtOAc (2×50 mL). The combined organic extracts were washed with water (50 mL), brine (50 mL) and dried over anhydrous $Na_2SO_4$ filtered and evaporated. The crude residue was purified by column chromatography ($SiO_2$) using EtOAc: Pet ether to give (3 g, 91%) tert-butyl (trans)-2-(3'-chlorobiphenyl-4-yl)cyclopropylcarbamate as a white solid.

Step 2:
To a cooled solution of tert-butyl (trans)-2-(3'-chlorobiphenyl-4-yl)cyclopropylcarbamate (3 g) in $Et_2O$ (15 mL) at 0° C. was added HCl in $Et_2O$ (15 mL), stirred for 16 h at RT. The progress of the reaction was monitored by TLC. After completion, the solvent was evaporated, residue was triturated with. $Et_2O$ to get (Trans)-2-(3'-chlorobiphenyl-4-yl)cyclopropanamine as HCl salt (2.3 g, 95.8%) as a white solid. The HCl salt was made free base by using $NaHCO_3$ solution and used in next reaction.

Step 3:
To a solution of (Trans)-2-(3'-chlorobiphenyl-4-yl)cyclopropanamine (520 mg, 2.1 mmol) and 6-methoxy-2,3-dihydro-1H-inden-1-one (381 mg, 2.3 mmol) in DCE (10 mL), sodium triacetoxy borohydrate (890 mg, 2 equiv) was added slowly at 0° C. and stirred for 20 h. After completion, the reaction mixture was evaporated. The residue was dissolved in Methanol (15 mL) and NaBH₄ (240 mg, 3 equiv) was added to the reaction mixture slowly at 0° C. and stirred for 3 h. After completion, the reaction mixture was poured into ice water (20 mL) and extracted with EtOAc (2×20 mL). The combined organic layers were washed with brine (20 mL) and dried over anhydrous Na₂SO₄, filtered and evaporated. The crude residue was purified by prep HPLC to give (110 mg, 13.2%) of free amine. Dioxane-HCl (20 mL) was added and stirred for 15 min at RT and evaporated to afford N-((trans)-2-(3'-chlorobiphenyl-4-yl)cyclopropyl)-6-methoxy-2,3-dihydro-1H-inden-1-amine hydrochloride (100 mg, 83%) as a pale brown solid. ¹H-NMR (DMSO-d6) δ (ppm): 1.41 (m, 1H), 1.61-1.69 (m, 1H), 2.33 (m, 1H), 2.44 (m, 1H), 2.64 (m, 1H), 2.81 (m, 1H), 3.03 (m, 2H), 3.65 (d, 3H), 4.88 (br, 1H), 6.92 (m, 1H), 7.23 (d, 1H), 7.29 (m, 2H), 7.42 (d, 1H), 7.50 (t, 2H), 7.63 (t, 3H), 7.71 (s, 1H), 9.71 (br, 1H), 9.88 (br, 1H). MS (M+H): 390.1.

The following compounds can be synthesized following the method described for Example 9, using the corresponding trans-cyclopropylamine derivative and the commercially available boronic acids.

Example 10: N-((trans)-2-(4'-chlorobiphenyl-4-yl)cyclopropyl)-6-methoxy-2,3-dihydro-1H-inden-1-amine hydrochloride

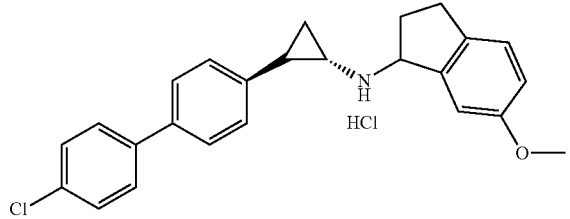

¹H-NMR (DMSO-d6) δ (ppm): 1.41 (m, 1H), 1.64-1.70 (m, 1H), 2.34 (m, 1H), 2.45 (m, 1H), 2.66 (m, 1H), 2.80 (m, 1H), 3.05 (m, 2H), 3.66 (d, 3H), 4.88 (br, 1H), 6.91 (m, 1H), 7.25 (m, 4H), 7.52 (d, 2H), 7.61 (d, 2H), 7.68 (d, 2H), 9.84 (br, 1H), 10.05 (br, 1H). MS (M+H): 390.1.

Example 11: 6-methoxy-N-((trans)-2-(3'-methoxybiphenyl-4-yl)cyclopropyl)-2,3-dihydro-1H-inden-1-amine hydrochloride

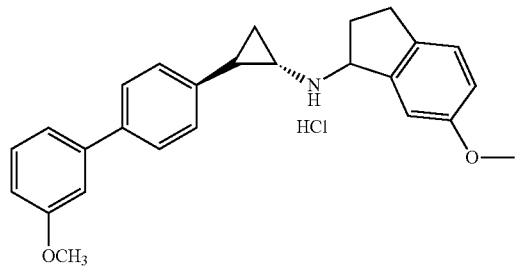

¹H-NMR (DMSO-d6) δ (ppm): 1.40 (m, 1H), 1.58-1.65 (m, 1H), 2.31 (m, 1H), 2.44 (m, 1H), 2.60 (m, 1H), 2.79 (m, 1H), 3.02 (m, 2H), 3.65 (d, 3H), 3.81 (s, 3H), 4.90 (br, 1H), 6.94 (m, 2H), 7.23 (m, 6H), 7.35 (t, 1H), 7.60 (d, 2H), 9.63 (br, 1H), 9.79 (br, 1H). MS (M+H): 386.1.

Example 12: N-trans-(2-cyclohexylethyl)-2-phenylcyclopropanamine hydrochloride

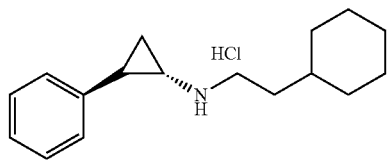

To a solution Intermediate B (1.5 g, 6.42 mmol) in Dimethylformamide (DMF, 30 mL) was added sodium hydride (0.38 mg, 9.64 mmol) and the suspension was stirred 30 min at room temperature. 1-Cyclohexylethyl bromide (1.2 mL, 7.71 mmol) was then added and the suspension stirred 12 h at room temperature. Solvents were evaporated and the residue was dissolved in dichloromethane (60 mL) and washed with water, brine and water, dried and concentrated. The obtained solid was purified by column chromatography to afford the Boc-protected product (1.4 g). This solid was dissolved in dichloromethane and HCl (15 mL) was added. The precipitate was filtered, washed with cold ether and dried to afford the desired product (1.56 g, 88%). ¹H-NMR (CDCl3) δ (ppm): 1.05 (m, 13H), 1.21 (m, 1H), 1.44 (m, 1H), 2.41 (m, 1H), 2.92 (m, 1H), 3.20 (m, 2H), 7.16-7.25 (m, 5H), 8.2 (bs, 2H). MS (M+H): 245.0.

The following compounds can be synthesized following the method described for Example 12 using the corresponding commercially available alkyl halides.

Example 13: (Trans)-N-(3-cyclohexylpropyl)-2-phenylcyclopropanamine hydrochloride

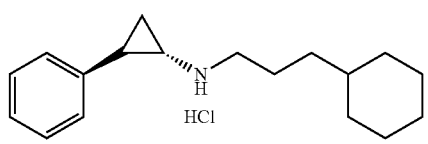

¹H-NMR (CD3OD) δ (ppm): 0.94 (m, 1H), 1.30 (m, 6H), 1.35 (q, 1H), 1.47 (m, 1H), 1.72 (m, 8H), 2.43 (m, 1H), 2.93 (quin, 1H), 3.14 (t, 2H), 7.17 (d, 2H), 7.22 (t, 1H), 7.30 (t, 2H). MS (M+H): 258.0.

Example 14: (Trans)-N-(2-cycloheptylethyl)-2-phenylcyclopropanamine hydrochloride

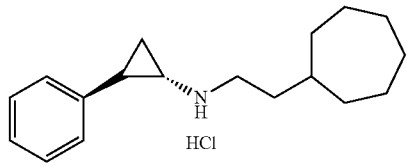

¹H-NMR (CD3OD) δ (ppm): 1.10 (m, 2H), 1.38 (m, 4H), 1.45 (m, 3H), 1.53 (m, 2H), 1.62 (m, 2H), 1.71 (t, 2H), 1.79

(m, 3H), 2.44 (m, 1H), 2.93 (quin, 1H), 3.16 (t, 2H), 7.16 (d, 2H), 7.23 (t, 1H), 7.31 (t, 2H). MS (M+H): 258.0.

Example 15: (Trans)-2-(4-(3-bromobenzyloxyl)phenyl)-N-(2-cyclohexylethyl)cyclopropanamine hydrochloride

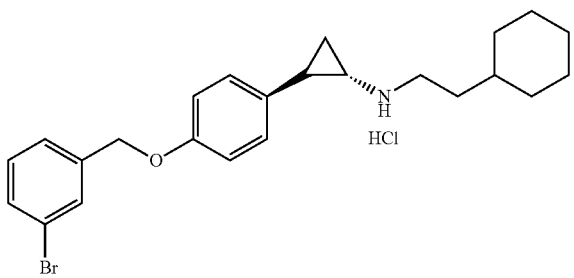

Step 1:
To a solution of tert-butyl-(trans)-2-(4-hydroxyphenyl)cyclopropylcarbamate (Intermediate N, 5 g, 20.0 mmol), K$_2$CO$_3$ (6.8 g, 50.0 mmol) in dry DMF (10 vols) was added 3-Bromo benzyl bromide (5 g, 20.0 mmol) and stirred at RT for 16 h. After completion, the reaction mixture was poured into ice water (150 mL) and extracted with EtOAc (2×75 mL). The combined extracts were washed with water (100 mL), brine (100 mL), dried over anhydrous Na$_2$SO$_4$, filtered and evaporated. The crude residue was purified by flash chromatography to give (tert-butyl (trans)-2-(4-(3-bromobenzyloxyl)phenyl)cyclopropylcarbamate (5.2 g, 62%) as a white solid. The crude was carried to next step without further purification.

Step 2:
To a cooled solution of (tert-butyl (trans)-2-(4-(3-bromobenzyloxy)phenyl)cyclopropyl carbamate (5.2 g) in Et$_2$O (50 mL) at 0° C., HCl in Et$_2$O (50 mL) was added, stirred for 16 h at RT. The solvent was evaporated, residue was triturated with Et$_2$O (2×20 mL) to get (Trans)-2-(4-(3-bromobenzyloxyl)phenyl)cyclopropanamine hydrochloride (3.3 g, 73%) as a white solid. The HCl salt was made free base by using NaHCO$_3$ solution and used in next reaction.

Step 3:
To a solution of (Trans)-2-(4-(3-bromobenzyloxy)phenyl)cyclopropanamine (2 g, 6.2 mmol) and 2-cyclohexylacetaldehyde (790 mg, 6.2 mmol) in DCE (20 mL) sodium triacetoxy borohydrate (2.3 g, 2 equiv) was added slowly at 0° C. and stirred for 20 h. After completion, the reaction mixture was evaporated. The residue was dissolved in Methanol (15 mL) and NaBH$_4$ (627 mg, 3 equiv) was added slowly at 0° C. to the reaction mixture and stirred for 3 h. After completion, the reaction mixture was poured into ice water (50 mL) and extracted with EtOAc (2×50 mL). The combined organic layers were washed with brine (50 mL) and dried over anhydrous Na$_2$SO$_4$, filtered and evaporated. The crude residue was purified by flash column chromatography by using EtOAc: Pet ether to get (Trans)-2-(4-(3-bromobenzyloxyl) phenyl)-N-(2-cyclohexylethyl)cyclopropane amine (500 mg, 21%) as a pale yellow liquid.

$^1$H-NMR (DMSO-d6) δ (ppm): 0.90 (q, 2H), 1.18 (m, 3H), 1.33 (m, 1H), 1.47 (m, 1H), 1.53 (q, 2H), 1.65 (br, 4H), 2.41 (m, 1H), 2.86 (m, 1H), 3.04 (m, 2H), 3.51 (br, 2H), 5.10 (s, 2H), 6.96 (d, 2H), 7.10 (d, 2H), 7.35 (t, 1H), 7.43 (d, 1H), 7.53 (d, 1H), 7.63 (s, 1H), 9.16 (br, 2H). MS (M+H): 428.2.

The following compounds can be synthesized following the method described for Example 15, using the corresponding trans-cyclopropylamine and the commercially available aldehydes or ketones.

Example 16: N-((trans)-2-(4-(3-bromobenzyloxyl)phenyl)cyclopropyl)-6-methoxy-2,3-dihydro-1H-inden-1-amine hydrochloride

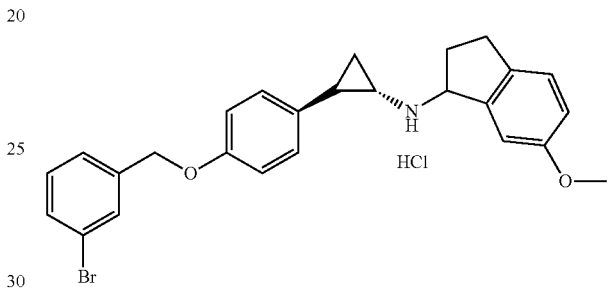

$^1$H-NMR (DMSO-d6) δ (ppm): 1.28 (m, 1H), 1.48-1.57 (m, 1H), 2.29 (m, 1H), 2.42 (m, 2H), 2.81 (m, 2H), 3.01 (m, 1H), 3.64 (d, 3H), 4.86 (br, 1H), 5.11 (s, 2H), 6.91 (d, 1H), 6.95 (d, 2H), 7.10 (t, 2H), 7.22 (m, 2H), 7.36 (m, 1H), 7.43 (d, 1H), 7.52 (d, 1H), 7.64 (s, 1H), 9.57 (br, 1H), 9.74 (br, 1H). MS (M+H): 464.1.

The following compounds can be prepared according to the synthetic schemes described or variations thereof by the ordinary skilled artisan using the appropriate starting materials and reagents.

Example 17: (Trans)-2-(3'-chlorobiphenyl-4-yl)-N-(2-cyclohexylethyl)cyclopropanamine

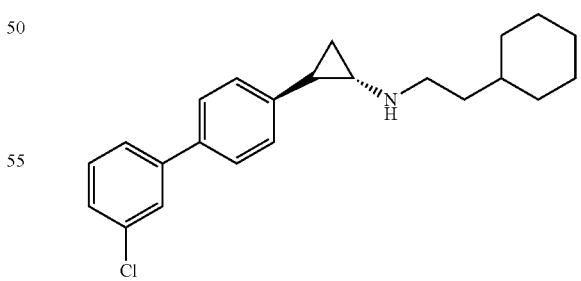

$^1$H-NMR (DMSO-d6) δ (ppm): 0.91 (q, J=12 Hz, 2H), 1.13-1.24 (m, 3H), 1.34 (q, J=7 Hz, 2H), 1.47-1.60 (m, 3H), 1.60-1.74 (m, 5H), 2.54 (brs, 1H), 3.01 (brs, 1H), 3.07 (brs, 2H), 7.28 (d, J=8 Hz, 2H), 7.41-7.43 (m, 1H), 7.48 (t, J=8 Hz, 1H), 7.64 (t, J=8 Hz, 3H), 7.71 (s, 1H), 9.21 (brs, 2H). MS (M+H): 354.1.

Example 18: (Trans)-2-(4'-chlorobiphenyl-4-yl)-N-(2-cyclohexylethyl)cyclopropanamine

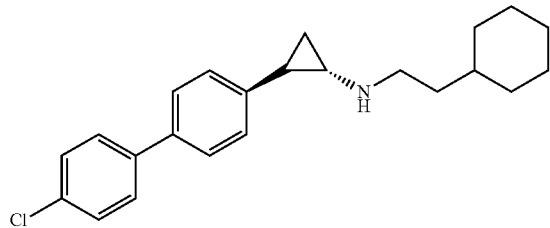

$^1$H-NMR (DMSO-d6) δ (ppm): 0.92 (q, J=12 Hz, 2H), 1.10-1.26 (m, 3H), 1.30-1.42 (m, 2H), 1.48-1.60 (m, 3H), 1.60-1.76 (m, 5H), 2.54 (brs, 1H), 3.02 (brs, 1H), 3.07 (brs, 2H), 7.28 (d, J=8 Hz, 2H), 7.51 (d, J=8 Hz, 2H), 7.62 (d, J=8 Hz, 2H), 7.68 (d, J=8 Hz, 2H), 9.18 (brs, 2H). MS (M+H): 354.1.

Example 19: (Trans)-N-(2-cyclohexylethyl)-2-(3'-methoxybiphenyl-4-yl)cyclopropanamine

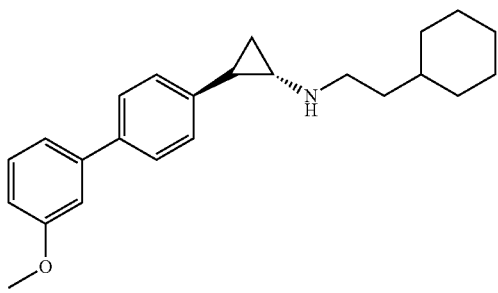

$^1$H-NMR (DMSO-d6) δ (ppm): 0.91 (q, J=12 Hz, 2H), 1.10-1.28 (m, 3H), 1.34-1.41 (m, 2H), 1.47-1.60 (m, 3H), 1.60-1.75 (m, 5H), 2.56 (brs, 1H), 3.00 (brs, 1H), 3.07 (brs, 2H), 3.82 (s, 3H), 6.88-6.96 (m, 1H), 7.16 (s, 1H), 7.21 (d, J=8 Hz, 1H), 7.26 (d, J=8 Hz, 2H), 7.37 (t, J=8 Hz, 1H), 7.61 (d, J=8 Hz, 2H), 9.24 (brs, 2H). MS (M+H): 350.2.

Example 20: N-((trans)-2-(4-(benzyloxy)phenyl)cyclopropyl)-7-methoxy-1,2,3,4-tetrahydronaphthalen-1-amine

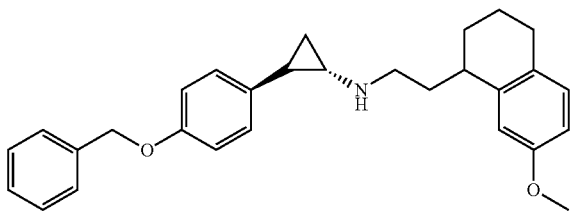

$^1$H-NMR (D$_2$O) δ (ppm): 1.30-1.52 (m, 2H), 1.80-1.98 (m, 2H), 2.02-2.17 (m, 2H), 2.21-2.30 (m, 1H), 2.43-2.54 (m, 1H), 2.64-2.92 (m, 2H), 3.01-3.08 (m, 1H), 3.38 and 3.46 (2s, 3H), 4.58-4.65 (m, 1H), 5.17 (s, 2H), 6.74-6.82 (m, 1H), 6.88-7.12 (m, 4H), 7.15-7.25 (m, 2H), 7.39-7.56 (m, 5H). MS (M+H): 400.2.

Without being bound by theory it is believed that the compounds described in the above examples are potent selective LSD1 inhibitors and can have use in treating or preventing disease were LSD1 inhibition is desirable.

Example 21: 1-((trans)-2-(4-(benzyloxy)phenyl)cyclopropylamino)cyclopropanecarboxamide

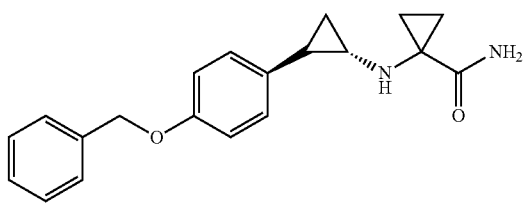

Example 22: Biological Assays

The compounds of the invention can be tested for their ability to inhibit LSD1. The ability of the compounds of the invention to inhibit LSD1 can be tested as follows. Human recombinant LSD1 protein was purchased from BPS Bioscience Inc. In order to monitor LSD1 enzymatic activity and/or its inhibition rate by our inhibitor(s) of interest, di-methylated H3-K4 peptide (Millipore) was chosen as a substrate. The demethylase activity was estimated, under aerobic conditions, by measuring the release of $H_2O_2$ produced during the catalytic process, using the Amplex® Red peroxide/peroxidase-coupled assay kit (Invitrogen).

Briefly, a fixed amount of LSD1 was incubated on ice for 15 minutes, in the absence and/or in the presence of various concentrations of inhibitor (e.g., from 0 to 75 µM, depending on the inhibitor strength). Tranylcypromine (Biomol International) was used as a control for inhibition. Within the experiment, each concentration of inhibitor was tested in triplicate. After leaving the enzyme interacting with the inhibitor, 12.5 µM of di-methylated H3-K4 peptide was added to each reaction and the experiment was left for 1 hour at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and left to incubate for 30 extra minutes at room temperature in the dark. A 1 µM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD1 was obtained in the absence of inhibitor and corrected for background fluorescence in the absence of LSD1. The Ki (IC50) of each inhibitor was estimated at half of the maximum activity.

The results presented in Table 1 below show the results of the LSD1 inhibition studies for a number of the Example compounds. Parnate (2-trans phenylcyclopropylamine) was found to have a Ki of from about 15 to 35 micromolar depending on the enzyme preparation. The studies show that the compounds of the invention have unexpectedly potent LSD1 inhibition.

Example 23: Biological Assays—Monoamine Oxidase Assays for Determining the Selectivity of the Compounds of the Invention for LSD1

Human recombinant monoamine oxidase proteins MAO-A and MAO-B were purchased from Sigma Aldrich. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay was set up. 3-(2-Aminophenyl)-3-oxopropanamine (kynuramine dihydrobromide, Sigma Aldrich), a non fluorescent compound was chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 µL. The assay buffer was 100 mM HEPES, pH 7.5. Each experiment was performed in triplicate within the same experiment.

Briefly, a fixed amount of MAO (0.25 µg for MAO-A and 0.5 µg for MAO-B) was incubated on ice for 15 minutes in the reaction buffer, in the absence and/or in the presence of various concentrations of inhibitor (e.g., from 0 to 50 µM, depending on the inhibitor strength). Tranylcypromine (Biomol International) was used as a control for inhibition.

After leaving the enzyme(s) interacting with the inhibitor, 60 to 90 µM of kynuramine was added to each reaction for MAO-B and MAO-A assay respectively, and the reaction was left for 1 hour at 37° C. in the dark. The oxidative deamination of the substrate was stopped by adding 50 µL (v/v) of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The Ki (IC50) of each inhibitor was determined at Vmax/2.

TABLE 1

Summary of Data from MAO-A, MAO-B, and LSD1 Inhibition Studies

| Example No. | MAO-A (Ki) | MAO-B (Ki) | LSD1 (Ki) |
|---|---|---|---|
| 1 | II | II, III | III |
| 2 | II | II | III |
| 3 | II | II | II, III |
| 4 | II | II | III |
| 5 | II | II | III |
| 6 | II | II | III |
| 7 | I | I | III |
| 8 | II | II | III |
| 9 | II | II | III |
| 10 | II | II | IV |
| 11 | II | II | IV |
| 12 | II | II | III |
| 13 | II | II | III |
| 14 | II | II | III |
| 15 | II | III | III |
| 16 | II | II | III |
| 18 | II | II | III, IV |
| 20 | II | II | III |

The ranges for the Ki value reported in Table 1 are for MAO-A-I=greater than 40 µM and II=between 1 µM and 40 µM; for MAO-B-I=greater than 40 µM, II=between 1 µM and 40 and III=between 0.1 µM and 1 µM; for LSD1-I=greater than 40 µM, II=between 1 µM and 40 µM, III=between 0.1 µM and 1 µM, and IV=between 0.001 µM and 0.1 µM. If two ranges are listed, this signifies that the value is near the boundary of the overlap e.g., II, III signifies about 1 µM.

Most of the compounds of Examples were found to have Ki (IC50) values for MAO-A and MAO-B of greater than 1 µM whereas LSD1 Ki values were in the nanomolar and low nanomolar range. Trans-2-phenylcyclopropylamine (tranylcypromine) was found to have a Ki for MAO-A of about 2 µM and a Ki of about 0.6 µM for MAO-B and from about 15-35 µM for LSD1 in these assays described herein.

The invention therefore provides inhibitors selective for LSD1. LSD1 selective inhibitors have Ki values for LSD1 which are at least 2-fold lower than the Ki value for MAO-A and/or MAO-B.

Thus the compounds of the invention are unexpectedly potent LSD1 inhibitors and unexpectedly selective for LSD1 as compared to MAO-A and MAO-B. There are compounds of the invention that inhibit both LSD1 and MAO-B to a greater extent than MAO-A and are therefore dual inhibitors of LSD1 and MAO-B.

Some compounds of the invention have MAO-B activity and may be useful for treating or preventing diseases treatable by MAO-B inhibition like depression and neurodegenerative diseases like Parkinson's disease, Alzheimer's disease, and Huntington's disease.

Example 24: Cancer Cell Line Study

The human colon cancer cell line HCT116 was obtained from the American Type Culture Collection (ATCC; CCL-247). The HCT116 cell line was maintained in DMEM GlutaMAX (Invitrogen) supplemented with 10% fetal calf serum.

Cells were grown in a humidified incubator at 37° C. in 5% $CO_2$.

AlamarBlue Assay

Cells were plated in 96-well plates at a density of 6000 cells/well in 100 µl medium 24 h before addition of drugs. They were then added in concentrations from 100 µM to 0.45 nM (each concentration in triplicate). To do so, a drugs-dilution plate at twice the screening concentrations was prepared. 72 hours later, alamarBlue (Biosource, Invitrogen) viability assay was performed following manufacturer's protocol. In brief, alamarBlue diluted in media was added to cells to have a 5% solution. Cells were incubated at 37° C., 3 hours and at room temperature, 30 min. Cells with no drug and, cells with no drug and lysed with triton X-100 were used as controls. Fluorescence was monitored at 530 nm excitation and 590 nm emission wavelengths. Results were quantified using Infinite F200 Microplate Reader (Tecan Group, Ltd.). EC50 were calculated as the dose of drugs required to inhibit cell growth by 50%, with Origin 7.0 computer program.

The EC50 value (µM) obtained for Example compound no. 1 was about 37.7 µM, for Example compound no. 2 about 50 µM, for Example compound no. 3 about 37 µM, for Example no. 9 about 35.1 µM, for Example 11 about 22.3 Example 12 about 63.8 µM, and for Example 15 about 13.3 µM.

Without being bound by theory, it is the inventor's belief that compounds of Formula 1 having for (A') an aromatic group like, arylalkyl, aryl, and arylalkoxy have excellent cell penetration and activity (or substituted versions thereof). These types of groups can be meta or para to the cyclopropyl ring of the compounds of Formula 1 and preferably are para. It was also unexpectedly found that compounds such as those in Examples 1, 2, 3, 4 & 5 and others in the Examples like these having carbocyclic groups directly attached to the amine group of the phenylcyclopropylamine core are potent and selective LSD1 inhibitors. Furthermore, it was unexpectedly found that phenylcyclopropylamine derivatives with alkyl groups substituting the amine wherein the alkyl groups are substituted with carbocycles and cycloalkyls are unexpectedly good inhibitors of LSD1. Furthermore the compounds of the invention have good activity in cell viability assays in cancer cell lines.

Previous reports of LSD1 have found that it is involved in cell proliferation and growth. Some studies have implicated LSD1 as a therapeutic target for cancer. Huang et al. (2007) *PNAS* 104:8023-8028 found that polyamine inhibitors of LSD1 modestly cause the reexpression of genes aberrantly silenced in cancer cells and particularly colorectal cancer (Huang et al. *Clin Cancer Res*. (2009) December 1; 15(23): 7217-28. Epub 2009 Nov. 24. PMID: 19934284). Scoumanne et al. ((2007) *J. Biol. Chem*. May 25; 282(21):15471-5) found that deficiency in LSD1 leads to a partial cell cycle arrest in G2/M and sensitizes cells to growth suppression induced by DNA damage. Kahl et al. ((2006) *Cancer Res*. 66(23):11341-7.) found that LSD1 expression is correlated with prostate cancer aggressiveness. Metzger et al. reported that LSD1 modulation by siRNA and pargyline regulates androgen receptor (AR) and may have therapeutic potential in cancers where AR plays a role, like prostate, testis, and brain cancers. Lee et al. ((2006) *Chem. Biol*. 13:563-567) reported that tranylcypromine derepresses Egr-1 gene expression in some cancer lines. A body of evidence is accumulating that Egr-1 is a tumor suppressor gene in many contexts (see e.g., Calogero et al. (2004) *Cancer Cell International* 4:1 exogenous expression of EGR-1 resulted in growth arrest and eventual cell death in primary cancer cell lines; Lucerna et al. (2006) *Cancer Research* 66, 6708-6713 show that sustained expression of Egr-1 causes antiangiogenic effects and inhibits tumor growth in some models; Ferraro et al. ((2005) *J. Clin. Oncol*. March 20; 23(9): 1921-6) reported that Egr-1 is downregulated in lung cancer patients with a higher risk of recurrence and may be more resistant to therapy. Thus, increasing Egr-1 expression via inhibition of LSD1 is a therapeutic approach for some cancers. Recent studies have also implicated LSD1 in brain cancer (Schulte et al. (2009) *Cancer Res*. March 1; 69(5): 2065-71). Other studies have implicated LSD1 in breast cancer (Lims et al. *Carcinogenesis*. 2009 Dec. 30. [Epub ahead of print] PMID: 20042638).

Thus, a body of evidence has implicated LSD1 in a number of cancers, which suggests that LSD1 is a therapeutic target for cancer. The instant inventors have discovered a class of LSD1 inhibitors that can be used to treat diseases where LSD1 is implicated as a therapeutic target like cancer. Accordingly, the phenylcyclopropylamine compounds of the invention can be used to treat such diseases.

Recent studies have also implicated LSD1 in viral infection and reactivation. In particular it was shown that pharmacological inhibitors of LSD1 like parnate and siRNA knock down of LSD1 caused reduced viral infectivity and reduced reactivation after latency (Liang et al. (2009) *Nat. Med*. 15:1312-1317). Therefore it is believed that the compounds of the invention can be used for treating or preventing viral infection. Furthermore, it is believed that the compounds of the invention can treat or prevent viral reactivation after latency.

Previous studies reported in the literature indicated that substitutions on the amine group of phenylcyclopropylamines reduced the ability of the compound to inhibit amine oxidases, which have significant structural homology to LSD1. For example, Zirkle et al. ((1962) *J. Med. Chem*. 1265-1284) found that a methyl substituent on the amine group decreased activity slightly whereas substitution with larger alkyl groups and groups bearing ring system like aralkyls reduced MAO activity substantially. The inventors of the instant invention have unexpectedly found that a variety of substitutions on the amine group of aryl cyclopropyl amine produce potent LSD1 inhibitors. Furthermore, compounds of Formula 1 with substituents in the para-position on the phenyl ring of the phenylcyclopropylamino core having an aromatic group result in highly active and selective compounds. The results of the instant invention show that further modifications to the aryl cyclopropylamine core as described herein can result in potent LSD1 inhibitors. Also contemplated as potent selective LSD1 inhibitors of the invention are heteroarylcyclopropyl amine derivatives (compounds of Formula 1 wherein (A) is a heteroaryl or of Formula 2 wherein (W) is a heteroaryl). The Examples show compounds which selectively inhibit LSD1 compared to MAO-A and MAO-B. Thus, the inventors have identified a new class of aryl- and heteroaryl cyclopropylamine containing LSD1 inhibitors with unexpected potency and selectivity for LSD1, a biologically relevant target in oncology.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

The invention claimed is:

1. A method of treating lung cancer, the method comprising administering, to a patient in need of treatment, a therapeutically effective amount of a compound of Formula 1

$$(A')_X\text{-}(A)\text{-}(B)\text{---}(Z)\text{-}(L)\text{-}(D) \qquad 1$$

wherein:
(A) is heteroaryl or aryl;
each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, haloalkoxy, aryl, arylalkoxy, alkyl, alkoxy, amido, —$CH_2C(=O)NH_2$, heteroaryl, cyano, sulfonyl, and sulfinyl;

X is 0, 1, 2, or 3;

(B) is a cyclopropyl ring, wherein (A) and (Z) are covalently bonded to different carbon atoms of (B);

(Z) is —NH—;

(L) is chosen from —$CH_2$—, —$CH_2CH_2$—, —$CH_2CH_2CH_2$—, and —$CH_2CH_2CH_2CH_2$—; and (D) is an aliphatic carbocyclic group or benzocycloalkyl, wherein said aliphatic carbocyclic group or said benzocycloalkyl has 0, 1, 2, or 3 substituents independently chosen from —$NH_2$, —$NH(C_1$-$C_6$ alkyl), —$N(C_1$-$C_6$ alkyl)($C_1$-$C_6$ alkyl), alkyl, halo, amido, cyano, alkoxy, haloalkyl, and haloalkoxy;

or an enantiomer, a diastereomer, or a mixture thereof, or a pharmaceutically acceptable salt or solvate thereof.

2. The method of claim 1, wherein said patient is a human.

\* \* \* \* \*